US007560108B2

(12) United States Patent
Evans et al.

(10) Patent No.: US 7,560,108 B2
(45) Date of Patent: Jul. 14, 2009

(54) ANTI-TNFα ANTIBODIES

(76) Inventors: Glen A. Evans, 1652 via Cancion, San Marcos, CA (US) 92069; Katya McLane, 1862 Falconer Ct., Vista, CA (US) 92083; Gopalan Raghunathan, 12620 Creekwood Ct., San Diego, CA (US) 92129

( * ) Notice: Subject to any disclaimer, the term of this patent is extended or adjusted under 35 U.S.C. 154(b) by 0 days.

(21) Appl. No.: 11/496,129

(22) Filed: Jul. 31, 2006

(65) Prior Publication Data

US 2007/0092518 A1    Apr. 26, 2007

Related U.S. Application Data

(60) Provisional application No. 60/705,427, filed on Aug. 4, 2005.

(51) Int. Cl.
*A61K 39/395* (2006.01)
*C07K 16/00* (2006.01)
*C07H 21/04* (2006.01)
*C12N 15/00* (2006.01)
*C12N 5/00* (2006.01)

(52) U.S. Cl. .............. 424/130.1; 530/387.1; 530/388.1; 536/23.5; 435/320.1; 435/325

(58) Field of Classification Search ........................ None
See application file for complete search history.

(56) References Cited

U.S. PATENT DOCUMENTS

| 5,656,272 | A | 8/1997 | Le et al. |
| 5,698,195 | A | 12/1997 | Le et al. |
| 5,919,452 | A | 7/1999 | Le et al. |
| 6,277,969 | B1 | 8/2001 | Le et al. |
| 6,284,471 | B1 | 9/2001 | Le et al. |
| 6,521,427 | B1 | 2/2003 | Evans |
| 6,790,444 | B2 | 9/2004 | Le et al. |
| 6,835,823 | B2 | 12/2004 | Le et al. |
| 2004/0131612 | A1* | 7/2004 | Watkins et al. ........... 424/145.1 |

OTHER PUBLICATIONS

Camussi, et al., "Tumor Necrosis Factor/Cachectin Stimulates Peritoneal Macrophages, Polymorphonuclear Neutrophils and Vascular Endothelial Cells to Synthesize and Release Platelet-Activating Factor," Journal of Experimental Medicine 166: 1390-1404 (1987).

Cerami, et al., "The role of cachectin/TNF in endotoxic shock and cachexia," Immunology Today, 9(1): 28-31 (1988).
Engelmann, et al., "Two Tumor Necrosis Factor-binding Proteins Purified from Human Urine," Journal of Biological Chemistry, 265(3): 1531-1536 (1990).
Hohmann, et al., "Two Different Cell Types Have Different Major Receptors for Human Tumor Necrosis Factor (TNFα)," Journal of Biological Chemistry, 264(25): 14927-14934.
Kohno, et al., "A second tumor necrosis factor receptor gene product can shed a naturally occurring tumor necrosis factor inhibitor," Proceedings of the National Academy of Science U.S.A., 87: 8331-8335 (1990).
Kriegler, et al., "A Novel Form of TNF/Cachectin Is a Cell Surface Cytotoxic Transmembrane Protein: Ramifications for the Complex Physiology of TNF," Cell 53: 45-53 (1988).
Maini, et al., "Therapeutic Efficacy of Multiple Intraveous Infusions of Anti-Tumor Necrosis Factor α Monoclonal Antibody Combined with Low-Dose Weekly Methotrexate in Rheumatoid Arthritis," Arthritis & Rheumatism, 41(9): 1552-1563 (1998).
Oliff, et al., "Tumors Secreting Human TNF/Cachectin Induce Cachexia in Mice," Cell, 50: 555-563 (1987).
Piguet, et al., "Tumor Necrosis Factor/Cachectin Is An Effector of Skin and Gut Lesions of the Acute Phase of Graft-vs.-Host Disease," Journal of Experimental Medicine, 166: 1280-1289 (1987).
Pober, et al., "Activation of Cultured Human Endothelial Cells by Recombinant Lymphotoxin: Comparison with Tumor Necrosis Factor and Interleukin 1 Species," Journal of Immunology, 138: 3319-3324 (1987).
Pober, et al., "Two Distinct Monokines, Interleukin 1 and Tumor Necrosis Factor, Each Independently Induce Biosynthesis and Transient Expression of the Same Antigen on the Surface of Cultured Human Vascular Endothelial Cells," Journal of Immunology, 136(5): 1680-1687 (1986).
Smith, et al., "The Active Form of Tumor Necrosis Factor Is a Trimer," Journal of Biological Chemistry, 262(15): 6951-6954 (1987).
Targan et al., "A Short-Term Study of Chimeric Monoclonal Antibody cA2 to Tumor Necrosis Factor α for Crohn's Disease," New England Journal of Medicine, 337(15): 1029-1035 (1997).
Tracey, et al., "Metabolic Responses to Cachectin/TNF," Annals of the New York Academy of Sciences, 587: 325-331 (1990).
Vassalli, "The Pathophysiology of Tumor Necrosis Factors," Annual Review of Immunology, 10: 411-452 (1992).
Zhang and Tracey, "Tumor Necrosis Factor," The Cytokine Handbook, Thomson AW (ed). 517-548 (1998).

* cited by examiner

*Primary Examiner*—Marianne P Allen
(74) *Attorney, Agent, or Firm*—Kirk Baumeister

(57) ABSTRACT

Novel TNFα antibody polypeptides and nucleic acids are disclosed. Methods of utilizing the polypeptides to treat TNFα-related diseases are also disclosed.

10 Claims, 3 Drawing Sheets

```
C7 V_H
EVQLVESGGGLVQPGGSLRLSCAASGFIFSNHWMNWVRQAPGKGLEWIGEIRSKSINSAT
Infliximab V_H  --K-E------------MK---V----------------S-E-----VA--------
---

C7 V_H
HYAESVKGRFIISRDDNKNSLYLEMNSLKTEDTAEYYCARNYYGSTYDYWGQGTLVTVS
Infliximab V_H  -----------T-----S-SAV---Q-TD-R----GV---S--------------
TL---
```

Figure 1

```
C7 V_L
EIVLTQSPDFQSVTPKEKVTITCRASQFVGSSIHWYQQKPDQSPKLLIKYASESMSGVPS
Infliximab V_L  D-L-----AIL---S-G-R-SFS----------------RTNG---R------------
I--

C7 V_L         RFSGSGSGTDFTFTISSLEAEDAATYYCQQSHSWPFTFGPGTKVDIK
Infliximab V_L ------------LS-NTV-S---I-D-------------S---NLEV-
```

Figure 2

SEQUENCE LISTING

```
<160> NUMBER OF SEQ ID NOS: 383

<210> SEQ ID NO 1
<211> LENGTH: 119
<212> TYPE: PRT
<213> ORGANISM: Mus musculus

<400> SEQUENCE: 1

Glu Val Lys Leu Glu Glu Ser Gly Gly Gly Leu Val Gln Pro Gly Gly
 1               5                  10                  15

Ser Met Lys Leu Ser Cys Val Ala Ser Gly Phe Ile Phe Ser Asn His
                20                  25                  30

Trp Met Asn Trp Val Arg Gln Ser Pro Glu Lys Gly Leu Glu Trp Val
            35                  40                  45

Ala Glu Ile Arg Ser Lys Ser Ile Asn Ser Ala Thr His Tyr Ala Glu
        50                  55                  60

Ser Val Lys Gly Arg Phe Thr Ile Ser Arg Asp Asp Ser Lys Ser Ala
65                  70                  75                  80

Val Tyr Leu Gln Met Asn Ser Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
                100                 105                 110

Gly Thr Thr Leu Thr Val Ser
        115

<210> SEQ ID NO 2
<211> LENGTH: 119
<212> TYPE: PRT
<213> ORGANISM: Artificial Sequence
<220> FEATURE:
<221> NAME/KEY: Mutagen
```

```
<222> LOCATION: (5)
<223> OTHER INFORMATION: Infliximab VH variant where Xaa can be V or T
<220> FEATURE:
<221> NAME/KEY: Mutagen
<222> LOCATION: (23)
<223> OTHER INFORMATION: Infliximab VH variant where Xaa can be A or R
<220> FEATURE:
<221> NAME/KEY: Mutagen
<222> LOCATION: (26)
<223> OTHER INFORMATION: Infliximab VH variant where Xaa can be G or Q
<220> FEATURE:
<221> NAME/KEY: Mutagen
<222> LOCATION: (27)
<223> OTHER INFORMATION: Infliximab VH variant where Xaa can be F or S
<220> FEATURE:
<221> NAME/KEY: Mutagen
<222> LOCATION: (28)
<223> OTHER INFORMATION: Infliximab VH variant where Xaa can be I or T
<220> FEATURE:
<221> NAME/KEY: Mutagen
<222> LOCATION: (33)
<223> OTHER INFORMATION: Infliximab VH variant where Xaa can be W or Y
<220> FEATURE:
<221> NAME/KEY: Mutagen
<222> LOCATION: (56)
<223> OTHER INFORMATION: Infliximab VH variant where Xaa can be I or S
<220> FEATURE:
<221> NAME/KEY: Mutagen
<222> LOCATION: (57)
<223> OTHER INFORMATION: Infliximab VH variant where Xaa can be N or Y
<220> FEATURE:
<221> NAME/KEY: Mutagen
<222> LOCATION: (58)
<223> OTHER INFORMATION: Infliximab VH variant where Xaa can be S or G
<220> FEATURE:
<221> NAME/KEY: Mutagen
<222> LOCATION: (61)
<223> OTHER INFORMATION: Infliximab VH variant where Xaa can be H or S
<220> FEATURE:
<221> NAME/KEY: Mutagen
<222> LOCATION: (76)
<223> OTHER INFORMATION: Infliximab VH variant where Xaa can be D or G
<220> FEATURE:
<221> NAME/KEY: Mutagen
<222> LOCATION: (78)
<223> OTHER INFORMATION: Infliximab VH variant where Xaa can be K or G
<220> FEATURE:
<221> NAME/KEY: Mutagen
<222> LOCATION: (79)
<223> OTHER INFORMATION: Infliximab VH variant where Xaa can be N or T
<220> FEATURE:
<221> NAME/KEY: Mutagen
<222> LOCATION: (80)
<223> OTHER INFORMATION: Infliximab VH variant where Xaa can be S or D
<220> FEATURE:
<221> NAME/KEY: Mutagen
<222> LOCATION: (82)
<223> OTHER INFORMATION: Infliximab VH variant where Xaa can be Y or T
<220> FEATURE:
<221> NAME/KEY: Mutagen
<222> LOCATION: (100)
<223> OTHER INFORMATION: Infliximab VH variant where Xaa can be R or Q
<220> FEATURE:
<221> NAME/KEY: Mutagen
<222> LOCATION: (107)
<223> OTHER INFORMATION: Infliximab VH variant where Xaa can be Y or P

<400> SEQUENCE: 2

Glu Val Gln Leu Xaa Glu Ser Gly Gly Gly Leu Val Gln Pro Gly Gly
 1               5                  10                  15

Ser Leu Arg Leu Ser Cys Xaa Ala Ser Xaa Xaa Xaa Phe Ser Asn His
            20                  25                  30

Xaa Met Asn Trp Val Arg Gln Ala Pro Gly Lys Gly Leu Glu Trp Ile
        35                  40                  45

Gly Glu Ile Arg Ser Lys Ser Xaa Xaa Xaa Ala Thr Xaa Tyr Ala Glu
```

```
                 50                  55                  60
Ser Val Lys Gly Arg Phe Ile Ile Ser Arg Asp Xaa Asn Xaa Xaa Xaa
 65                  70                  75                  80

Leu Xaa Leu Glu Met Asn Ser Leu Lys Thr Glu Asp Thr Ala Glu Tyr
                 85                  90                  95

Tyr Cys Ala Xaa Asn Tyr Tyr Gly Ser Thr Xaa Asp Tyr Trp Gly Gln
                100                 105                 110

Gly Thr Leu Val Thr Val Ser
            115

<210> SEQ ID NO 3
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 3

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ile Phe Ser Asn His
                20                  25                  30

Trp Met Asn Trp Val Arg Gln Ala Pro Gly Lys Gly Leu Glu Trp Ile
            35                  40                  45

Gly Glu Ile Arg Ser Lys Ser Ile Asn Ser Ala Thr His Tyr Ala Glu
        50                  55                  60

Ser Val Lys Gly Arg Phe Ile Ile Ser Arg Asp Asp Asn Lys Asn Ser
 65                  70                  75                  80

Leu Tyr Leu Glu Met Asn Ser Leu Lys Thr Glu Asp Thr Ala Glu Tyr
                 85                  90                  95

Tyr Cys Ala Arg Asn Tyr Tyr Gly Ser Thr Tyr Asp Tyr Trp Gly Gln
                100                 105                 110

Gly Thr Leu Val Thr Val Ser
            115

<210> SEQ ID NO 4
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 4

Glu Val Gln Leu Thr Glu Ser Gly Gly Gly Leu Val Gln Pro Gly Gly
 1               5                  10                  15

Ser Leu Arg Leu Ser Cys Arg Ala Ser Gly Phe Ile Phe Ser Asn His
                20                  25                  30

Trp Met Asn Trp Val Arg Gln Ala Pro Gly Lys Gly Leu Glu Trp Ile
            35                  40                  45

Gly Glu Ile Arg Ser Lys Ser Tyr Ser Ala Thr Ser Tyr Ala Glu
        50                  55                  60

Ser Val Lys Gly Arg Phe Ile Ile Ser Arg Asp Asp Asn Lys Thr Ser
 65                  70                  75                  80

Leu Tyr Leu Glu Met Asn Ser Leu Lys Thr Glu Asp Thr Ala Glu Tyr
                 85                  90                  95

Tyr Cys Ala Gln Asn Tyr Tyr Gly Ser Thr Tyr Asp Tyr Trp Gly Gln
                100                 105                 110
```

```
Gly Thr Leu Val Thr Val Ser
        115

<210> SEQ ID NO 5
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 5

Glu Val Gln Leu Thr Glu Ser Gly Gly Leu Val Gln Pro Gly Gly
 1               5                  10                  15

Ser Leu Arg Leu Ser Cys Ala Ala Ser Gln Phe Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Asn Ser Ala Thr His Tyr Ala Glu
    50                  55                  60

Ser Val Lys Gly Arg Phe Ile Ile Ser Arg Asp Asp Asn Lys Asn Ser
65                  70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 6
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 6

Glu Val Gln Leu Val Glu Ser Gly Gly Gly Leu Val Gln Pro Gly Gly
 1               5                  10                  15

Ser Leu Arg Leu Ser Cys Ala Ala Ser Gln Phe Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Tyr Ser Ala Thr His Tyr Ala Glu
    50                  55                  60

Ser Val Lys Gly Arg Phe Ile Ile Ser Arg Asp Gly Asn Lys Thr Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 7
<211> LENGTH: 119
<212> TYPE: PRT
<213> ORGANISM: Artificial Sequence
<220> FEATURE:
<223> OTHER INFORMATION: Infliximab VH variant
```

-continued

```
<400> SEQUENCE: 7

Glu Val Gln Leu Thr Glu Ser Gly Gly Gly Leu Val Gln Pro Gly Gly
1               5                   10                  15

Ser Leu Arg Leu Ser Cys Ala Ala Ser Gln Phe Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ser Asn Ser Ala Thr His Tyr Ala Glu
    50                  55                  60

Ser Val Lys Gly Arg Phe Ile Ile Ser Arg Asp Asp Asn Lys Thr Asp
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 8
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 8

Glu Val Gln Leu Thr Glu Ser Gly Gly Gly Leu Val Gln Pro Gly Gly
1               5                   10                  15

Ser Leu Arg Leu Ser Cys Arg Ala Ser Gly Ser Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Asn Gly Ala Thr His Tyr Ala Glu
    50                  55                  60

Ser Val Lys Gly Arg Phe Ile Ile Ser Arg Asp Gly Asn Gly Asn Asp
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 9
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 9

Glu Val Gln Leu Thr Glu Ser Gly Gly Gly Leu Val Gln Pro Gly Gly
1               5                   10                  15

Ser Leu Arg Leu Ser Cys Arg Ala Ser Gln Ser Ile Phe Ser Asn His
            20                  25                  30

Tyr Met Asn Trp Val Arg Gln Ala Pro Gly Lys Gly Leu Glu Trp Ile
        35                  40                  45
```

```
Gly Glu Ile Arg Ser Lys Ser Ile Asn Ser Ala Thr Ser Tyr Ala Glu
    50                  55                  60

Ser Val Lys Gly Arg Phe Ile Ile Ser Arg Asp Asp Asn Gly Asn Asp
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115
```

<210> SEQ ID NO 10
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 10

```
Glu Val Gln Leu Thr Glu Ser Gly Gly Gly Leu Val Gln Pro Gly Gly
1               5                   10                  15

Ser Leu Arg Leu Ser Cys Arg Ala Ser Gly Phe Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Asn Ser Ala Thr Ser Tyr Ala Glu
    50                  55                  60

Ser Val Lys Gly Arg Phe Ile Ile Ser Arg Asp Asp Asn Lys Asn Asp
65                  70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115
```

<210> SEQ ID NO 11
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 11

```
Glu Val Gln Leu Thr Glu Ser Gly Gly Gly Leu Val Gln Pro Gly Gly
1               5                   10                  15

Ser Leu Arg Leu Ser Cys Ala Ala Ser Gly Phe Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Asn Gly Ala Thr Ser Tyr Ala Glu
    50                  55                  60

Ser Val Lys Gly Arg Phe Ile Ile Ser Arg Asp Asp Asn Lys Asn Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110
```

```
Gly Thr Leu Val Thr Val Ser
        115

<210> SEQ ID NO 12
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 12

Glu Val Gln Leu Thr Glu Ser Gly Gly Gly Leu Val Gln Pro Gly Gly
  1               5                  10                  15

Ser Leu Arg Leu Ser Cys Arg Ala Ser Gln Ser Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ser Asn Ser Ala Thr Ser Tyr Ala Glu
    50                  55                  60

Ser Val Lys Gly Arg Phe Ile Ile Ser Arg Asp Gly Asn Lys Asn Asp
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 13
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 13

Glu Val Gln Leu Thr Glu Ser Gly Gly Gly Leu Val Gln Pro Gly Gly
  1               5                  10                  15

Ser Leu Arg Leu Ser Cys Ala Ala Ser Gly Ser Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Asn Ser Ala Thr His Tyr Ala Glu
    50                  55                  60

Ser Val Lys Gly Arg Phe Ile Ile Ser Arg Asp Asp Asn Lys Thr Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 14
<211> LENGTH: 119
<212> TYPE: PRT
<213> ORGANISM: Artificial Sequence
<220> FEATURE:
<223> OTHER INFORMATION: Infliximab VH variant
```

<400> SEQUENCE: 14

Glu Val Gln Leu Thr Glu Ser Gly Gly Gly Leu Val Gln Pro Gly Gly
1               5                   10                  15

Ser Leu Arg Leu Ser Cys Ala Ala Ser Gln Phe Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Tyr Gly Ala Thr His Tyr Ala Glu
    50                  55                  60

Ser Val Lys Gly Arg Phe Ile Ile Ser Arg Asp Gly Asn Gly Asn Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 15
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 15

Glu Val Gln Leu Thr Glu Ser Gly Gly Gly Leu Val Gln Pro Gly Gly
1               5                   10                  15

Ser Leu Arg Leu Ser Cys Arg Ala Ser Gln Ser Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ser Tyr Ser Ala Thr His Tyr Ala Glu
    50                  55                  60

Ser Val Lys Gly Arg Phe Ile Ile Ser Arg Asp Asp Asn Lys Asn Asp
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 16
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 16

Glu Val Gln Leu Thr Glu Ser Gly Gly Gly Leu Val Gln Pro Gly Gly
1               5                   10                  15

Ser Leu Arg Leu Ser Cys Ala Ala Ser Gln Ser Ile Phe Ser Asn His
            20                  25                  30

Tyr Met Asn Trp Val Arg Gln Ala Pro Gly Lys Gly Leu Glu Trp Ile
        35                  40                  45

```
Gly Glu Ile Arg Ser Lys Ser Ser Asn Ser Ala Thr His Tyr Ala Glu
        50                  55                  60
Ser Val Lys Gly Arg Phe Ile Ile Ser Arg Asp Gly Asn Gly Asn Asp
65                  70                  75                  80
Leu Thr Leu Glu Met Asn Ser Leu Lys Thr Glu Asp Thr Ala Glu Tyr
                85                  90                  95
Tyr Cys Ala Gln Asn Tyr Tyr Gly Ser Thr Pro Asp Tyr Trp Gly Gln
                100                 105                 110
Gly Thr Leu Val Thr Val Ser
        115
```

<210> SEQ ID NO 17
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 17

```
Glu Val Gln Leu Thr Glu Ser Gly Gly Gly Leu Val Gln Pro Gly Gly
1               5                   10                  15
Ser Leu Arg Leu Ser Cys Arg Ala Ser Gly Phe Thr Phe Ser Asn His
                20                  25                  30
Trp Met Asn Trp Val Arg Gln Ala Pro Gly Lys Gly Leu Glu Trp Ile
            35                  40                  45
Gly Glu Ile Arg Ser Lys Ser Ser Tyr Ser Ala Thr His Tyr Ala Glu
        50                  55                  60
Ser Val Lys Gly Arg Phe Ile Ile Ser Arg Asp Asp Asn Lys Thr Ser
65                  70                  75                  80
Leu Tyr Leu Glu Met Asn Ser Leu Lys Thr Glu Asp Thr Ala Glu Tyr
                85                  90                  95
Tyr Cys Ala Arg Asn Tyr Tyr Gly Ser Thr Pro Asp Tyr Trp Gly Gln
                100                 105                 110
Gly Thr Leu Val Thr Val Ser
        115
```

<210> SEQ ID NO 18
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 18

```
Glu Val Gln Leu Val Glu Ser Gly Gly Gly Leu Val Gln Pro Gly Gly
1               5                   10                  15
Ser Leu Arg Leu Ser Cys Arg Ala Ser Gln Phe Thr Phe Ser Asn His
                20                  25                  30
Tyr Met Asn Trp Val Arg Gln Ala Pro Gly Lys Gly Leu Glu Trp Ile
            35                  40                  45
Gly Glu Ile Arg Ser Lys Ser Ser Asn Gly Ala Thr Ser Tyr Ala Glu
        50                  55                  60
Ser Val Lys Gly Arg Phe Ile Ile Ser Arg Asp Gly Asn Gly Asn Ser
65                  70                  75                  80
Leu Thr Leu Glu Met Asn Ser Leu Lys Thr Glu Asp Thr Ala Glu Tyr
                85                  90                  95
Tyr Cys Ala Arg Asn Tyr Tyr Gly Ser Thr Tyr Asp Tyr Trp Gly Gln
```

```
                        100                 105                 110

Gly Thr Leu Val Thr Val Ser
        115

<210> SEQ ID NO 19
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 19

Glu Val Gln Leu Thr Glu Ser Gly Gly Gly Leu Val Gln Pro Gly Gly
 1               5                  10                  15

Ser Leu Arg Leu Ser Cys Arg Ala Ser Gln Phe Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Asn Ser Ala Thr Ser Tyr Ala Glu
    50                  55                  60

Ser Val Lys Gly Arg Phe Ile Ile Ser Arg Asp Asp Asn Lys Thr Ser
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 20
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 20

Glu Val Gln Leu Val Glu Ser Gly Gly Gly Leu Val Gln Pro Gly Gly
 1               5                  10                  15

Ser Leu Arg Leu Ser Cys Arg Ala Ser Gly Phe Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Asn Ser Ala Thr Ser Tyr Ala Glu
    50                  55                  60

Ser Val Lys Gly Arg Phe Ile Ile Ser Arg Asp Asn Gly Asn Asp
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 21
<211> LENGTH: 119
<212> TYPE: PRT
<213> ORGANISM: Artificial Sequence
<220> FEATURE:
```

<223> OTHER INFORMATION: Infliximab VH variant

<400> SEQUENCE: 21

Glu Val Gln Leu Thr Glu Ser Gly Gly Gly Leu Val Gln Pro Gly Gly
1               5                   10                  15
Ser Leu Arg Leu Ser Cys Ala Ala Ser Gln Phe Thr Phe Ser Asn His
            20                  25                  30
Trp Met Asn Trp Val Arg Gln Ala Pro Gly Lys Gly Leu Glu Trp Ile
        35                  40                  45
Gly Glu Ile Arg Ser Lys Ser Ile Tyr Gly Ala Thr His Tyr Ala Glu
    50                  55                  60
Ser Val Lys Gly Arg Phe Ile Ile Ser Arg Asp Asp Asn Gly Asn Asp
65                  70                  75                  80
Leu Tyr Leu Glu Met Asn Ser Leu Lys Thr Glu Asp Thr Ala Glu Tyr
                85                  90                  95
Tyr Cys Ala Arg Asn Tyr Tyr Gly Ser Thr Tyr Asp Tyr Trp Gly Gln
            100                 105                 110
Gly Thr Leu Val Thr Val Ser
        115

<210> SEQ ID NO 22
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 22

Glu Val Gln Leu Val Glu Ser Gly Gly Gly Leu Val Gln Pro Gly Gly
1               5                   10                  15
Ser Leu Arg Leu Ser Cys Arg Ala Ser Gly Ser Thr Phe Ser Asn His
            20                  25                  30
Trp Met Asn Trp Val Arg Gln Ala Pro Gly Lys Gly Leu Glu Trp Ile
        35                  40                  45
Gly Glu Ile Arg Ser Lys Ser Asn Ser Ala Thr His Tyr Ala Glu
    50                  55                  60
Ser Val Lys Gly Arg Phe Ile Ile Ser Arg Asp Asp Asn Gly Asn Ser
65                  70                  75                  80
Leu Thr Leu Glu Met Asn Ser Leu Lys Thr Glu Asp Thr Ala Glu Tyr
                85                  90                  95
Tyr Cys Ala Gln Asn Tyr Tyr Gly Ser Thr Tyr Asp Tyr Trp Gly Gln
            100                 105                 110
Gly Thr Leu Val Thr Val Ser
        115

<210> SEQ ID NO 23
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 23

Glu Val Gln Leu Thr Glu Ser Gly Gly Gly Leu Val Gln Pro Gly Gly
1               5                   10                  15
Ser Leu Arg Leu Ser Cys Ala Ala Ser Gly Ser Ile Phe Ser Asn His
            20                  25                  30
Trp Met Asn Trp Val Arg Gln Ala Pro Gly Lys Gly Leu Glu Trp Ile

```
                35                  40                  45
Gly Glu Ile Arg Ser Lys Ser Ile Tyr Gly Ala Thr His Tyr Ala Glu
        50                  55                  60

Ser Val Lys Gly Arg Phe Ile Ile Ser Arg Asp Asp Asn Gly Thr Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 24
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 24

Glu Val Gln Leu Thr Glu Ser Gly Gly Gly Leu Val Gln Pro Gly Gly
1               5                   10                  15

Ser Leu Arg Leu Ser Cys Ala Ala Ser Gly Ser Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Asn Gly Ala Thr Ser Tyr Ala Glu
        50                  55                  60

Ser Val Lys Gly Arg Phe Ile Ile Ser Arg Asp Asp Asn Gly Asn Ser
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 25
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Arg Ala Ser Gln Phe Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Asn Ser Ala Thr His Tyr Ala Glu
        50                  55                  60

Ser Val Lys Gly Arg Phe Ile Ile Ser Arg Asp Gly Asn Lys Thr Ser
65                  70                  75                  80

Leu Tyr Leu Glu Met Asn Ser Leu Lys Thr Glu Asp Thr Ala Glu Tyr
                85                  90                  95
```

```
Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 26
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 26

Glu Val Gln Leu Val Glu Ser Gly Gly Gly Leu Val Gln Pro Gly Gly
 1               5                  10                  15

Ser Leu Arg Leu Ser Cys Arg Ala Ser Gln Phe Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Tyr Ser Ala Thr His Tyr Ala Glu
    50                  55                  60

Ser Val Lys Gly Arg Phe Ile Ile Ser Arg Asp Asp Asn Lys Asn Asp
65                  70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 27
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 27

Glu Val Gln Leu Val Glu Ser Gly Gly Gly Leu Val Gln Pro Gly Gly
 1               5                  10                  15

Ser Leu Arg Leu Ser Cys Ala Ala Ser Gln Phe Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Asn Gly Ala Thr His Tyr Ala Glu
    50                  55                  60

Ser Val Lys Gly Arg Phe Ile Ile Ser Arg Asp Asp Asn Lys Asn Asp
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 28
<211> LENGTH: 119
<212> TYPE: PRT
<213> ORGANISM: Artificial Sequence
```

<220> FEATURE:
<223> OTHER INFORMATION: Infliximab VH variant

<400> SEQUENCE: 28

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Ser | Thr | Phe | Ser | Asn | His |
|---|---|---|---|---|---|---|---|---|---|---|---|---|---|---|---|
| | | | 20 | | | | | 25 | | | | | 30 | | |

| Trp | Met | Asn | Trp | Val | Arg | Gln | Ala | Pro | Gly | Lys | Gly | Leu | Glu | Trp | Ile |
|---|---|---|---|---|---|---|---|---|---|---|---|---|---|---|---|
| | | 35 | | | | | 40 | | | | | 45 | | | |

| Gly | Glu | Ile | Arg | Ser | Lys | Ser | Tyr | Gly | Ala | Thr | Ser | Tyr | Ala | Glu |
|---|---|---|---|---|---|---|---|---|---|---|---|---|---|---|
| 50 | | | | | 55 | | | | | 60 | | | | |

| Ser | Val | Lys | Gly | Arg | Phe | Ile | Ile | Ser | Arg | Asp | Gly | Asn | Gly | Asn | Ser |
|---|---|---|---|---|---|---|---|---|---|---|---|---|---|---|---|
| 65 | | | | | 70 | | | | | 75 | | | | | 80 |

| Leu | Thr | Leu | Glu | Met | Asn | Ser | Leu | Lys | Thr | Glu | Asp | Thr | Ala | Glu | Tyr |
|---|---|---|---|---|---|---|---|---|---|---|---|---|---|---|---|
| | | | | 85 | | | | | 90 | | | | | 95 | |

| Tyr | Cys | Ala | Gln | Asn | Tyr | Tyr | Gly | Ser | Thr | Pro | Asp | Tyr | Trp | Gly | Gln |
|---|---|---|---|---|---|---|---|---|---|---|---|---|---|---|---|
| | | | 100 | | | | | 105 | | | | | 110 | | |

| Gly | Thr | Leu | Val | Thr | Val | Ser |
|---|---|---|---|---|---|---|
| | | | 115 | | | |

<210> SEQ ID NO 29
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 29

| Glu | Val | Gln | Leu | Thr | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Arg | Ala | Ser | Gln | Ser | Ile | Phe | Ser | Asn | His |
|---|---|---|---|---|---|---|---|---|---|---|---|---|---|---|---|
| | | | 20 | | | | | 25 | | | | | 30 | | |

| Tyr | Met | Asn | Trp | Val | Arg | Gln | Ala | Pro | Gly | Lys | Gly | Leu | Glu | Trp | Ile |
|---|---|---|---|---|---|---|---|---|---|---|---|---|---|---|---|
| | | 35 | | | | | 40 | | | | | 45 | | | |

| Gly | Glu | Ile | Arg | Ser | Lys | Ser | Ser | Asn | Ser | Ala | Thr | Ser | Tyr | Ala | Glu |
|---|---|---|---|---|---|---|---|---|---|---|---|---|---|---|---|
| 50 | | | | | 55 | | | | | 60 | | | | | |

| Ser | Val | Lys | Gly | Arg | Phe | Ile | Ile | Ser | Arg | Asp | Asp | Asn | Lys | Thr | Ser |
|---|---|---|---|---|---|---|---|---|---|---|---|---|---|---|---|
| 65 | | | | | 70 | | | | | 75 | | | | | 80 |

| Leu | Tyr | Leu | Glu | Met | Asn | Ser | Leu | Lys | Thr | Glu | Asp | Thr | Ala | Glu | Tyr |
|---|---|---|---|---|---|---|---|---|---|---|---|---|---|---|---|
| | | | | 85 | | | | | 90 | | | | | 95 | |

| Tyr | Cys | Ala | Arg | Asn | Tyr | Tyr | Gly | Ser | Thr | Tyr | Asp | Tyr | Trp | Gly | Gln |
|---|---|---|---|---|---|---|---|---|---|---|---|---|---|---|---|
| | | | 100 | | | | | 105 | | | | | 110 | | |

| Gly | Thr | Leu | Val | Thr | Val | Ser |
|---|---|---|---|---|---|---|
| | | | 115 | | | |

<210> SEQ ID NO 30
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 30

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Arg | Ala | Ser | Gln | Ser | Thr | Phe | Ser | Asn | His |
|---|---|---|---|---|---|---|---|---|---|---|---|---|---|---|---|
| | | | 20 | | | | | 25 | | | | | 30 | | |

```
Trp Met Asn Trp Val Arg Gln Ala Pro Gly Lys Gly Leu Glu Trp Ile
            35                  40                  45

Gly Glu Ile Arg Ser Lys Ser Ile Tyr Ser Ala Thr Ser Tyr Ala Glu
 50                      55                  60

Ser Val Lys Gly Arg Phe Ile Ile Ser Arg Asp Gly Asn Lys Thr Ser
 65                  70                  75                  80

Leu Thr Leu Glu Met Asn Ser Leu Lys Thr Glu Asp Thr Ala Glu Tyr
                 85                  90                  95

Tyr Cys Ala Gln Asn Tyr Tyr Gly Ser Thr Pro Asp Tyr Trp Gly Gln
                100                 105                 110

Gly Thr Leu Val Thr Val Ser
            115

<210> SEQ ID NO 31
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 31

Glu Val Gln Leu Thr Glu Ser Gly Gly Gly Leu Val Gln Pro Gly Gly
  1               5                  10                  15

Ser Leu Arg Leu Ser Cys Ala Ala Ser Gln Phe Ile Phe Ser Asn His
             20                  25                  30

Tyr Met Asn Trp Val Arg Gln Ala Pro Gly Lys Gly Leu Glu Trp Ile
            35                  40                  45

Gly Glu Ile Arg Ser Lys Ser Ser Tyr Gly Ala Thr His Tyr Ala Glu
 50                      55                  60

Ser Val Lys Gly Arg Phe Ile Ile Ser Arg Asp Gly Asn Lys Thr Asp
 65                  70                  75                  80

Leu Thr Leu Glu Met Asn Ser Leu Lys Thr Glu Asp Thr Ala Glu Tyr
                 85                  90                  95

Tyr Cys Ala Gln Asn Tyr Tyr Gly Ser Thr Tyr Asp Tyr Trp Gly Gln
                100                 105                 110

Gly Thr Leu Val Thr Val Ser
            115

<210> SEQ ID NO 32
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 32

Glu Val Gln Leu Thr Glu Ser Gly Gly Gly Leu Val Gln Pro Gly Gly
  1               5                  10                  15

Ser Leu Arg Leu Ser Cys Arg Ala Ser Gln Phe Thr Phe Ser Asn His
             20                  25                  30

Tyr Met Asn Trp Val Arg Gln Ala Pro Gly Lys Gly Leu Glu Trp Ile
            35                  40                  45

Gly Glu Ile Arg Ser Lys Ser Ser Asn Gly Ala Thr Ser Tyr Ala Glu
 50                      55                  60

Ser Val Lys Gly Arg Phe Ile Ile Ser Arg Asp Gly Asn Gly Asn Ser
 65                  70                  75                  80

Leu Thr Leu Glu Met Asn Ser Leu Lys Thr Glu Asp Thr Ala Glu Tyr
                 85                  90                  95
```

```
Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 33
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 33

Glu Val Gln Leu Val Glu Ser Gly Gly Gly Leu Val Gln Pro Gly Gly
  1               5                  10                  15

Ser Leu Arg Leu Ser Cys Arg Ala Ser Gly Ser Ile Phe Ser Asn His
             20                  25                  30

Tyr Met Asn Trp Val Arg Gln Ala Pro Gly Lys Gly Leu Glu Trp Ile
         35                  40                  45

Gly Glu Ile Arg Ser Lys Ser Ser Asn Gly Ala Thr His Tyr Ala Glu
     50                  55                  60

Ser Val Lys Gly Arg Phe Ile Ile Ser Arg Asp Asp Asn Lys Asn Ser
 65                  70                  75                  80

Leu Tyr Leu Glu Met Asn Ser Leu Lys Thr Glu Asp Thr Ala Glu Tyr
                 85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 34
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 34

Glu Val Gln Leu Val Glu Ser Gly Gly Gly Leu Val Gln Pro Gly Gly
  1               5                  10                  15

Ser Leu Arg Leu Ser Cys Ala Ala Ser Gln Ser Ile Phe Ser Asn His
             20                  25                  30

Trp Met Asn Trp Val Arg Gln Ala Pro Gly Lys Gly Leu Glu Trp Ile
         35                  40                  45

Gly Glu Ile Arg Ser Lys Ser Ile Asn Gly Ala Thr Ser Tyr Ala Glu
     50                  55                  60

Ser Val Lys Gly Arg Phe Ile Ile Ser Arg Asp Gly Asn Gly Thr Ser
 65                  70                  75                  80

Leu Thr Leu Glu Met Asn Ser Leu Lys Thr Glu Asp Thr Ala Glu Tyr
                 85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 35
<211> LENGTH: 119
<212> TYPE: PRT
```

<213> ORGANISM: Artificial Sequence
<220> FEATURE:
<223> OTHER INFORMATION: Infliximab VH variant

<400> SEQUENCE: 35

Glu Val Gln Leu Thr Glu Ser Gly Gly Gly Leu Val Gln Pro Gly Gly
1               5                   10                  15

Ser Leu Arg Leu Ser Cys Arg Ala Ser Gln Ser Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Asn Ser Ala Thr Ser Tyr Ala Glu
    50                  55                  60

Ser Val Lys Gly Arg Phe Ile Ile Ser Arg Asp Gly Asn Gly Asn Asp
65                  70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
                100                 105                 110

Gly Thr Leu Val Thr Val Ser
        115

<210> SEQ ID NO 36
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gln Phe Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Tyr Gly Ala Thr Ser Tyr Ala Glu
    50                  55                  60

Ser Val Lys Gly Arg Phe Ile Ile Ser Arg Asp Asp Asn Gly Thr Ser
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
                100                 105                 110

Gly Thr Leu Val Thr Val Ser
        115

<210> SEQ ID NO 37
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 37

Glu Val Gln Leu Thr Glu Ser Gly Gly Gly Leu Val Gln Pro Gly Gly
1               5                   10                  15

Ser Leu Arg Leu Ser Cys Arg Ala Ser Gln Ser Thr Phe Ser Asn His
            20                  25                  30

Tyr Met Asn Trp Val Arg Gln Ala Pro Gly Lys Gly Leu Glu Trp Ile
            35                  40                  45

Gly Glu Ile Arg Ser Lys Ser Ser Asn Ser Ala Thr Ser Tyr Ala Glu
 50                  55                  60

Ser Val Lys Gly Arg Phe Ile Ile Ser Arg Asp Gly Asn Gly Asn Asp
 65                  70                  75                  80

Leu Tyr Leu Glu Met Asn Ser Leu Lys Thr Glu Asp Thr Ala Glu Tyr
                    85                  90                  95

Tyr Cys Ala Gln Asn Tyr Tyr Gly Ser Thr Tyr Asp Tyr Trp Gly Gln
                    100                 105                 110

Gly Thr Leu Val Thr Val Ser
            115

<210> SEQ ID NO 38
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 38

Glu Val Gln Leu Thr Glu Ser Gly Gly Gly Leu Val Gln Pro Gly Gly
 1               5                   10                  15

Ser Leu Arg Leu Ser Cys Arg Ala Ser Gln Ser Thr Phe Ser Asn His
            20                  25                  30

Trp Met Asn Trp Val Arg Gln Ala Pro Gly Lys Gly Leu Glu Trp Ile
            35                  40                  45

Gly Glu Ile Arg Ser Lys Ser Ser Tyr Gly Ala Thr Ser Tyr Ala Glu
 50                  55                  60

Ser Val Lys Gly Arg Phe Ile Ile Ser Arg Asp Gly Asn Gly Asn Ser
 65                  70                  75                  80

Leu Thr Leu Glu Met Asn Ser Leu Lys Thr Glu Asp Thr Ala Glu Tyr
                    85                  90                  95

Tyr Cys Ala Gln Asn Tyr Tyr Gly Ser Thr Tyr Asp Tyr Trp Gly Gln
                    100                 105                 110

Gly Thr Leu Val Thr Val Ser
            115

<210> SEQ ID NO 39
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 39

Glu Val Gln Leu Val Glu Ser Gly Gly Gly Leu Val Gln Pro Gly Gly
 1               5                   10                  15

Ser Leu Arg Leu Ser Cys Arg Ala Ser Gln Ser Thr Phe Ser Asn His
            20                  25                  30

Tyr Met Asn Trp Val Arg Gln Ala Pro Gly Lys Gly Leu Glu Trp Ile
            35                  40                  45

Gly Glu Ile Arg Ser Lys Ser Ile Asn Ser Ala Thr His Tyr Ala Glu
 50                  55                  60

Ser Val Lys Gly Arg Phe Ile Ile Ser Arg Asp Gly Asn Lys Asn Asp
 65                  70                  75                  80

Leu Thr Leu Glu Met Asn Ser Leu Lys Thr Glu Asp Thr Ala Glu Tyr

```
                            85                  90                  95
Tyr Cys Ala Arg Asn Tyr Tyr Gly Ser Thr Tyr Asp Tyr Trp Gly Gln
                100                 105                 110

Gly Thr Leu Val Thr Val Ser
        115

<210> SEQ ID NO 40
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 40

Glu Val Gln Leu Val Glu Ser Gly Gly Gly Leu Val Gln Pro Gly Gly
  1               5                  10                  15

Ser Leu Arg Leu Ser Cys Ala Ala Ser Gly Ser Thr Phe Ser Asn His
                20                  25                  30

Tyr Met Asn Trp Val Arg Gln Ala Pro Gly Lys Gly Leu Glu Trp Ile
            35                  40                  45

Gly Glu Ile Arg Ser Lys Ser Ile Asn Ser Ala Thr Ser Tyr Ala Glu
        50                  55                  60

Ser Val Lys Gly Arg Phe Ile Ile Ser Arg Asp Gly Asn Gly Thr Ser
 65                 70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
                100                 105                 110

Gly Thr Leu Val Thr Val Ser
        115

<210> SEQ ID NO 41
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 41

Glu Val Gln Leu Thr Glu Ser Gly Gly Gly Leu Val Gln Pro Gly Gly
  1               5                  10                  15

Ser Leu Arg Leu Ser Cys Arg Ala Ser Gln Ser Thr Phe Ser Asn His
                20                  25                  30

Tyr Met Asn Trp Val Arg Gln Ala Pro Gly Lys Gly Leu Glu Trp Ile
            35                  40                  45

Gly Glu Ile Arg Ser Lys Ser Ser Asn Gly Ala Thr Ser Tyr Ala Glu
        50                  55                  60

Ser Val Lys Gly Arg Phe Ile Ile Ser Arg Asp Asp Asn Gly Thr Asp
 65                 70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
                100                 105                 110

Gly Thr Leu Val Thr Val Ser
        115

<210> SEQ ID NO 42
<211> LENGTH: 119
```

```
<212> TYPE: PRT
<213> ORGANISM: Artificial Sequence
<220> FEATURE:
<223> OTHER INFORMATION: Infliximab VH variant

<400> SEQUENCE: 42

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Tyr Ser Ala Thr Ser Tyr Ala Glu
    50                  55                  60

Ser Val Lys Gly Arg Phe Ile Ile Ser Arg Asp Asp Asn Lys Asn Ser
65                  70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 43
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 43

Glu Val Gln Leu Val Glu Ser Gly Gly Gly Leu Val Gln Pro Gly Gly
 1               5                  10                  15

Ser Leu Arg Leu Ser Cys Arg Ala Ser Gly Ser Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Asn Gly Ala Thr Ser Tyr Ala Glu
    50                  55                  60

Ser Val Lys Gly Arg Phe Ile Ile Ser Arg Asp Asp Asn Gly Asn Ser
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 44
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 44

Glu Val Gln Leu Thr Glu Ser Gly Gly Gly Leu Val Gln Pro Gly Gly
 1               5                  10                  15

Ser Leu Arg Leu Ser Cys Ala Ala Ser Gly Phe Thr Phe Ser Asn His
```

```
                    20                  25                  30
Trp Met Asn Trp Val Arg Gln Ala Pro Gly Lys Gly Leu Glu Trp Ile
            35                  40                  45
Gly Glu Ile Arg Ser Lys Ser Ser Tyr Ser Ala Thr His Tyr Ala Glu
 50                  55                  60
Ser Val Lys Gly Arg Phe Ile Ile Ser Arg Asp Asp Asn Lys Thr Asp
 65                  70                  75                  80
Leu Thr Leu Glu Met Asn Ser Leu Lys Thr Glu Asp Thr Ala Glu Tyr
                85                  90                  95
Tyr Cys Ala Arg Asn Tyr Tyr Gly Ser Thr Tyr Asp Tyr Trp Gly Gln
            100                 105                 110
Gly Thr Leu Val Thr Val Ser
            115

<210> SEQ ID NO 45
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 45

Glu Val Gln Leu Val Glu Ser Gly Gly Gly Leu Val Gln Pro Gly Gly
  1               5                  10                  15
Ser Leu Arg Leu Ser Cys Arg Ala Ser Gly Phe Ile Phe Ser Asn His
            20                  25                  30
Trp Met Asn Trp Val Arg Gln Ala Pro Gly Lys Gly Leu Glu Trp Ile
            35                  40                  45
Gly Glu Ile Arg Ser Lys Ser Ile Tyr Ser Ala Thr His Tyr Ala Glu
 50                  55                  60
Ser Val Lys Gly Arg Phe Ile Ile Ser Arg Asp Gly Asn Gly Asn Asp
 65                  70                  75                  80
Leu Thr Leu Glu Met Asn Ser Leu Lys Thr Glu Asp Thr Ala Glu Tyr
                85                  90                  95
Tyr Cys Ala Arg Asn Tyr Tyr Gly Ser Thr Pro Asp Tyr Trp Gly Gln
            100                 105                 110
Gly Thr Leu Val Thr Val Ser
            115

<210> SEQ ID NO 46
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 46

Glu Val Gln Leu Val Glu Ser Gly Gly Gly Leu Val Gln Pro Gly Gly
  1               5                  10                  15
Ser Leu Arg Leu Ser Cys Arg Ala Ser Gly Ser Thr Phe Ser Asn His
            20                  25                  30
Tyr Met Asn Trp Val Arg Gln Ala Pro Gly Lys Gly Leu Glu Trp Ile
            35                  40                  45
Gly Glu Ile Arg Ser Lys Ser Ser Tyr Gly Ala Thr Ser Tyr Ala Glu
 50                  55                  60
Ser Val Lys Gly Arg Phe Ile Ile Ser Arg Asp Gly Asn Gly Asn Asp
 65                  70                  75                  80
```

```
Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 47
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 47

Glu Val Gln Leu Val Glu Ser Gly Gly Gly Leu Val Gln Pro Gly Gly
 1               5                  10                  15

Ser Leu Arg Leu Ser Cys Arg Ala Ser Gln Ser Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Asn Ser Ala Thr His Tyr Ala Glu
    50                  55                  60

Ser Val Lys Gly Arg Phe Ile Ile Ser Arg Asp Asp Asn Gly Thr Ser
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 48
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 48

Glu Val Gln Leu Thr Glu Ser Gly Gly Gly Leu Val Gln Pro Gly Gly
 1               5                  10                  15

Ser Leu Arg Leu Ser Cys Arg Ala Ser Gln Phe Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Tyr Gly Ala Thr His Tyr Ala Glu
    50                  55                  60

Ser Val Lys Gly Arg Phe Ile Ile Ser Arg Asp Asp Asn Lys Thr Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 49
```

```
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 49

Glu Val Gln Leu Thr Glu Ser Gly Gly Gly Leu Val Gln Pro Gly Gly
 1               5                  10                  15

Ser Leu Arg Leu Ser Cys Ala Ala Ser Gln Phe Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ser Tyr Gly Ala Thr His Tyr Ala Glu
    50                  55                  60

Ser Val Lys Gly Arg Phe Ile Ile Ser Arg Asp Gly Asn Gly Asn Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 50
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 50

Glu Val Gln Leu Thr Glu Ser Gly Gly Gly Leu Val Gln Pro Gly Gly
 1               5                  10                  15

Ser Leu Arg Leu Ser Cys Ala Ala Ser Gln Ser Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Tyr Ser Ala Thr Ser Tyr Ala Glu
    50                  55                  60

Ser Val Lys Gly Arg Phe Ile Ile Ser Arg Asp Asp Asn Gly Asn Asp
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 51
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 51

Glu Val Gln Leu Thr Glu Ser Gly Gly Gly Leu Val Gln Pro Gly Gly
 1               5                  10                  15
```

```
Ser Leu Arg Leu Ser Cys Arg Ala Ser Gly Phe Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Tyr Ser Ala Thr Ser Tyr Ala Glu
    50                  55                  60

Ser Val Lys Gly Arg Phe Ile Ile Ser Arg Asp Gly Asn Lys Asn Asp
65                  70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 52
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Arg Ala Ser Gly Ser Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ser Tyr Ser Ala Thr His Tyr Ala Glu
    50                  55                  60

Ser Val Lys Gly Arg Phe Ile Ile Ser Arg Asp Gly Asn Gly Asn Ser
65                  70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 53
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 53

Glu Val Gln Leu Thr Glu Ser Gly Gly Gly Leu Val Gln Pro Gly Gly
1               5                   10                  15

Ser Leu Arg Leu Ser Cys Arg Ala Ser Gln Ser Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ser Tyr Gly Ala Thr His Tyr Ala Glu
    50                  55                  60

Ser Val Lys Gly Arg Phe Ile Ile Ser Arg Asp Asp Asn Gly Thr Asp
65                  70                  75                  80
```

```
Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 54
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 54

Glu Val Gln Leu Thr Glu Ser Gly Gly Gly Leu Val Gln Pro Gly Gly
1               5                   10                  15

Ser Leu Arg Leu Ser Cys Ala Ala Ser Gly Ser Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Tyr Gly Ala Thr Ser Tyr Ala Glu
    50                  55                  60

Ser Val Lys Gly Arg Phe Ile Ile Ser Arg Asp Gly Asn Gly Asn Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 55
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 55

Glu Val Gln Leu Thr Glu Ser Gly Gly Gly Leu Val Gln Pro Gly Gly
1               5                   10                  15

Ser Leu Arg Leu Ser Cys Arg Ala Ser Gly Ser Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Tyr Gly Ala Thr His Tyr Ala Glu
    50                  55                  60

Ser Val Lys Gly Arg Phe Ile Ile Ser Arg Asp Gly Asn Gly Thr Asp
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115
```

<210> SEQ ID NO 56
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 56

Glu Val Gln Leu Thr Glu Ser Gly Gly Gly Leu Val Gln Pro Gly Gly
1               5                   10                  15

Ser Leu Arg Leu Ser Cys Arg Ala Ser Gly Ser Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Tyr Gly Ala Thr His Tyr Ala Glu
    50                  55                  60

Ser Val Lys Gly Arg Phe Ile Ile Ser Arg Asp Gly Asn Gly Thr Asp
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 57
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 57

Glu Val Gln Leu Thr Glu Ser Gly Gly Gly Leu Val Gln Pro Gly Gly
1               5                   10                  15

Ser Leu Arg Leu Ser Cys Ala Ala Ser Gly Phe Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ser Tyr Ser Ala Thr His Tyr Ala Glu
    50                  55                  60

Ser Val Lys Gly Arg Phe Ile Ile Ser Arg Asp Asp Asn Gly Thr Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 58
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 58

Glu Val Gln Leu Thr Glu Ser Gly Gly Gly Leu Val Gln Pro Gly Gly
1               5                   10                  15

```
Ser Leu Arg Leu Ser Cys Ala Ala Ser Gln Phe Ile Phe Ser Asn His
            20                  25                  30

Trp Met Asn Trp Val Arg Gln Ala Pro Gly Lys Gly Leu Glu Trp Ile
            35                  40                  45

Gly Glu Ile Arg Ser Lys Ser Ser Asn Ser Ala Thr Ser Tyr Ala Glu
    50                  55                  60

Ser Val Lys Gly Arg Phe Ile Ile Ser Arg Asp Asp Asn Gly Asn Asp
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
                100                 105                 110

Gly Thr Leu Val Thr Val Ser
            115

<210> SEQ ID NO 59
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Arg Ala Ser Gln Ser Ile Phe Ser Asn His
            20                  25                  30

Trp Met Asn Trp Val Arg Gln Ala Pro Gly Lys Gly Leu Glu Trp Ile
            35                  40                  45

Gly Glu Ile Arg Ser Lys Ser Ile Asn Ser Ala Thr Ser Tyr Ala Glu
    50                  55                  60

Ser Val Lys Gly Arg Phe Ile Ile Ser Arg Asp Asp Asn Gly Thr Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
                100                 105                 110

Gly Thr Leu Val Thr Val Ser
            115

<210> SEQ ID NO 60
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 60

Glu Val Gln Leu Thr Glu Ser Gly Gly Gly Leu Val Gln Pro Gly Gly
1               5                   10                  15

Ser Leu Arg Leu Ser Cys Arg Ala Ser Gln Ser Thr Phe Ser Asn His
            20                  25                  30

Trp Met Asn Trp Val Arg Gln Ala Pro Gly Lys Gly Leu Glu Trp Ile
            35                  40                  45

Gly Glu Ile Arg Ser Lys Ser Ile Asn Gly Ala Thr Ser Tyr Ala Glu
    50                  55                  60

Ser Val Lys Gly Arg Phe Ile Ile Ser Arg Asp Asp Asn Gly Asn Ser
```

```
               65                  70                  75                  80
Leu Thr Leu Glu Met Asn Ser Leu Lys Thr Glu Asp Thr Ala Glu Tyr
                    85                  90                  95

Tyr Cys Ala Gln Asn Tyr Tyr Gly Ser Thr Tyr Asp Tyr Trp Gly Gln
                100                 105                 110

Gly Thr Leu Val Thr Val Ser
        115

<210> SEQ ID NO 61
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 61

Glu Val Gln Leu Val Glu Ser Gly Gly Gly Leu Val Gln Pro Gly Gly
  1               5                  10                  15

Ser Leu Arg Leu Ser Cys Arg Ala Ser Gly Phe Ile Phe Ser Asn His
                 20                  25                  30

Tyr Met Asn Trp Val Arg Gln Ala Pro Gly Lys Gly Leu Glu Trp Ile
             35                  40                  45

Gly Glu Ile Arg Ser Lys Ser Ile Tyr Gly Ala Thr His Tyr Ala Glu
         50                  55                  60

Ser Val Lys Gly Arg Phe Ile Ile Ser Arg Asp Gly Asn Gly Asn Asp
 65                  70                  75                  80

Leu Tyr Leu Glu Met Asn Ser Leu Lys Thr Glu Asp Thr Ala Glu Tyr
                    85                  90                  95

Tyr Cys Ala Arg Asn Tyr Tyr Gly Ser Thr Tyr Asp Tyr Trp Gly Gln
                100                 105                 110

Gly Thr Leu Val Thr Val Ser
        115

<210> SEQ ID NO 62
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 62

Glu Val Gln Leu Thr Glu Ser Gly Gly Gly Leu Val Gln Pro Gly Gly
  1               5                  10                  15

Ser Leu Arg Leu Ser Cys Ala Ala Ser Gln Ser Thr Phe Ser Asn His
                 20                  25                  30

Trp Met Asn Trp Val Arg Gln Ala Pro Gly Lys Gly Leu Glu Trp Ile
             35                  40                  45

Gly Glu Ile Arg Ser Lys Ser Ser Asn Gly Ala Thr Ser Tyr Ala Glu
         50                  55                  60

Ser Val Lys Gly Arg Phe Ile Ile Ser Arg Asp Gly Asn Lys Asn Ser
 65                  70                  75                  80

Leu Thr Leu Glu Met Asn Ser Leu Lys Thr Glu Asp Thr Ala Glu Tyr
                    85                  90                  95

Tyr Cys Ala Arg Asn Tyr Tyr Gly Ser Thr Tyr Asp Tyr Trp Gly Gln
                100                 105                 110

Gly Thr Leu Val Thr Val Ser
        115
```

-continued

<210> SEQ ID NO 63
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 63

Glu Val Gln Leu Thr Glu Ser Gly Gly Gly Leu Val Gln Pro Gly Gly
 1               5                  10                  15

Ser Leu Arg Leu Ser Cys Arg Ala Ser Gly Phe Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Tyr Gly Ala Thr Ser Tyr Ala Glu
    50                  55                  60

Ser Val Lys Gly Arg Phe Ile Ile Ser Arg Asp Gly Asn Gly Thr Asp
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 64
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 64

Glu Val Gln Leu Thr Glu Ser Gly Gly Gly Leu Val Gln Pro Gly Gly
 1               5                  10                  15

Ser Leu Arg Leu Ser Cys Ala Ala Ser Gln Phe Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Tyr Gly Ala Thr His Tyr Ala Glu
    50                  55                  60

Ser Val Lys Gly Arg Phe Ile Ile Ser Arg Asp Asp Asn Lys Thr Ser
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 65
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 65

Glu Val Gln Leu Val Glu Ser Gly Gly Gly Leu Val Gln Pro Gly Gly

```
                1               5                  10                 15
Ser Leu Arg Leu Ser Cys Arg Ala Ser Gly Phe Ile Phe Ser Asn His
                20                 25                 30

Trp Met Asn Trp Val Arg Gln Ala Pro Gly Lys Gly Leu Glu Trp Ile
            35                 40                 45

Gly Glu Ile Arg Ser Lys Ser Ile Tyr Gly Ala Thr His Tyr Ala Glu
        50                 55                 60

Ser Val Lys Gly Arg Phe Ile Ile Ser Arg Asp Asp Asn Lys Asn Ser
65                 70                 75                 80

Leu Tyr Leu Glu Met Asn Ser Leu Lys Thr Glu Asp Thr Ala Glu Tyr
                85                 90                 95

Tyr Cys Ala Gln Asn Tyr Tyr Gly Ser Thr Tyr Asp Tyr Trp Gly Gln
            100                105                110

Gly Thr Leu Val Thr Val Ser
        115

<210> SEQ ID NO 66
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 66

Glu Val Gln Leu Thr Glu Ser Gly Gly Gly Leu Val Gln Pro Gly Gly
1               5                  10                 15

Ser Leu Arg Leu Ser Cys Arg Ala Ser Gly Phe Thr Phe Ser Asn His
                20                 25                 30

Tyr Met Asn Trp Val Arg Gln Ala Pro Gly Lys Gly Leu Glu Trp Ile
            35                 40                 45

Gly Glu Ile Arg Ser Lys Ser Ile Tyr Ser Ala Thr His Tyr Ala Glu
        50                 55                 60

Ser Val Lys Gly Arg Phe Ile Ile Ser Arg Asp Asp Asn Lys Thr Asp
65                 70                 75                 80

Leu Thr Leu Glu Met Asn Ser Leu Lys Thr Glu Asp Thr Ala Glu Tyr
                85                 90                 95

Tyr Cys Ala Arg Asn Tyr Tyr Gly Ser Thr Tyr Asp Tyr Trp Gly Gln
            100                105                110

Gly Thr Leu Val Thr Val Ser
        115

<210> SEQ ID NO 67
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 67

Glu Val Gln Leu Thr Glu Ser Gly Gly Gly Leu Val Gln Pro Gly Gly
1               5                  10                 15

Ser Leu Arg Leu Ser Cys Arg Ala Ser Gly Phe Thr Phe Ser Asn His
                20                 25                 30

Tyr Met Asn Trp Val Arg Gln Ala Pro Gly Lys Gly Leu Glu Trp Ile
            35                 40                 45

Gly Glu Ile Arg Ser Lys Ser Ile Tyr Ser Ala Thr His Tyr Ala Glu
        50                 55                 60
```

```
Ser Val Lys Gly Arg Phe Ile Ile Ser Arg Asp Gly Asn Lys Thr Asp
 65                  70                  75                  80

Leu Thr Leu Glu Met Asn Ser Leu Lys Thr Glu Asp Thr Ala Glu Tyr
                 85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115
```

<210> SEQ ID NO 68
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 68

```
Glu Val Gln Leu Thr Glu Ser Gly Gly Gly Leu Val Gln Pro Gly Gly
 1               5                  10                  15

Ser Leu Arg Leu Ser Cys Arg Ala Ser Gln Phe Ile Phe Ser Asn His
                20                  25                  30

Trp Met Asn Trp Val Arg Gln Ala Pro Gly Lys Gly Leu Glu Trp Ile
            35                  40                  45

Gly Glu Ile Arg Ser Lys Ser Asn Ser Ala Thr His Tyr Ala Glu
 50                  55                  60

Ser Val Lys Gly Arg Phe Ile Ile Ser Arg Asp Asp Asn Lys Asn Asp
 65                  70                  75                  80

Leu Thr Leu Glu Met Asn Ser Leu Lys Thr Glu Asp Thr Ala Glu Tyr
                 85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115
```

<210> SEQ ID NO 69
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 69

```
Glu Val Gln Leu Val Glu Ser Gly Gly Gly Leu Val Gln Pro Gly Gly
 1               5                  10                  15

Ser Leu Arg Leu Ser Cys Arg Ala Ser Gln Phe Thr Phe Ser Asn His
                20                  25                  30

Trp Met Asn Trp Val Arg Gln Ala Pro Gly Lys Gly Leu Glu Trp Ile
            35                  40                  45

Gly Glu Ile Arg Ser Lys Ser Asn Ser Ala Thr His Tyr Ala Glu
 50                  55                  60

Ser Val Lys Gly Arg Phe Ile Ile Ser Arg Asp Gly Asn Gly Asn Ser
 65                  70                  75                  80

Leu Tyr Leu Glu Met Asn Ser Leu Lys Thr Glu Asp Thr Ala Glu Tyr
                 85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115
```

<210> SEQ ID NO 70
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 70

Glu Val Gln Leu Thr Glu Ser Gly Gly Gly Leu Val Gln Pro Gly Gly
 1               5                  10                  15

Ser Leu Arg Leu Ser Cys Arg Ala Ser Gln Ser Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Asn Gly Ala Thr His Tyr Ala Glu
    50                  55                  60

Ser Val Lys Gly Arg Phe Ile Ile Ser Arg Asp Asp Asn Lys Asn Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 71
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 71

Glu Val Gln Leu Thr Glu Ser Gly Gly Gly Leu Val Gln Pro Gly Gly
 1               5                  10                  15

Ser Leu Arg Leu Ser Cys Arg Ala Ser Gly Ser Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Tyr Gly Ala Thr Ser Tyr Ala Glu
    50                  55                  60

Ser Val Lys Gly Arg Phe Ile Ile Ser Arg Asp Gly Asn Lys Thr Ser
65                  70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 72
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 72

Glu Val Gln Leu Thr Glu Ser Gly Gly Gly Leu Val Gln Pro Gly Gly
1               5                   10                  15

Ser Leu Arg Leu Ser Cys Arg Ala Ser Gly Ser Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Tyr Ser Ala Thr His Tyr Ala Glu
50                  55                  60

Ser Val Lys Gly Arg Phe Ile Ile Ser Arg Asp Gly Asn Gly Thr Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 73
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Arg Ala Ser Gly Ser Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Tyr Gly Ala Thr Ser Tyr Ala Glu
50                  55                  60

Ser Val Lys Gly Arg Phe Ile Ile Ser Arg Asp Asp Asn Lys Asn Asp
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 74
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 74

Glu Val Gln Leu Thr Glu Ser Gly Gly Gly Leu Val Gln Pro Gly Gly
1               5                   10                  15

Ser Leu Arg Leu Ser Cys Ala Ala Ser Gly Ser Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ser Tyr Ser Ala Thr Ser Tyr Ala Glu
50                  55                  60

```
Ser Val Lys Gly Arg Phe Ile Ile Ser Arg Asp Asp Asn Lys Asn Ser
 65                  70                  75                  80

Leu Thr Leu Glu Met Asn Ser Leu Lys Thr Glu Asp Thr Ala Glu Tyr
                 85                  90                  95

Tyr Cys Ala Arg Asn Tyr Tyr Gly Ser Thr Pro Asp Tyr Trp Gly Gln
             100                 105                 110

Gly Thr Leu Val Thr Val Ser
        115

<210> SEQ ID NO 75
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 75

Glu Val Gln Leu Val Glu Ser Gly Gly Gly Leu Val Gln Pro Gly Gly
 1               5                  10                  15

Ser Leu Arg Leu Ser Cys Arg Ala Ser Gly Phe Thr Phe Ser Asn His
             20                  25                  30

Trp Met Asn Trp Val Arg Gln Ala Pro Gly Lys Gly Leu Glu Trp Ile
         35                  40                  45

Gly Glu Ile Arg Ser Lys Ser Ile Tyr Ser Ala Thr His Tyr Ala Glu
     50                  55                  60

Ser Val Lys Gly Arg Phe Ile Ile Ser Arg Asp Asp Asn Lys Asn Ser
 65                  70                  75                  80

Leu Thr Leu Glu Met Asn Ser Leu Lys Thr Glu Asp Thr Ala Glu Tyr
                 85                  90                  95

Tyr Cys Ala Arg Asn Tyr Tyr Gly Ser Thr Pro Asp Tyr Trp Gly Gln
             100                 105                 110

Gly Thr Leu Val Thr Val Ser
        115

<210> SEQ ID NO 76
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 76

Glu Val Gln Leu Thr Glu Ser Gly Gly Gly Leu Val Gln Pro Gly Gly
 1               5                  10                  15

Ser Leu Arg Leu Ser Cys Arg Ala Ser Gly Phe Ile Phe Ser Asn His
             20                  25                  30

Tyr Met Asn Trp Val Arg Gln Ala Pro Gly Lys Gly Leu Glu Trp Ile
         35                  40                  45

Gly Glu Ile Arg Ser Lys Ser Ile Asn Gly Ala Thr His Tyr Ala Glu
     50                  55                  60

Ser Val Lys Gly Arg Phe Ile Ile Ser Arg Asp Asp Asn Gly Thr Ser
 65                  70                  75                  80

Leu Tyr Leu Glu Met Asn Ser Leu Lys Thr Glu Asp Thr Ala Glu Tyr
                 85                  90                  95

Tyr Cys Ala Arg Asn Tyr Tyr Gly Ser Thr Tyr Asp Tyr Trp Gly Gln
             100                 105                 110

Gly Thr Leu Val Thr Val Ser
```

-continued

```
          115

<210> SEQ ID NO 77
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 77

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Tyr Ser Ala Thr Ser Tyr Ala Glu
    50                  55                  60

Ser Val Lys Gly Arg Phe Ile Ile Ser Arg Asp Asp Asn Gly Asn Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 78
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 78

Glu Val Gln Leu Thr Glu Ser Gly Gly Gly Leu Val Gln Pro Gly Gly
 1               5                  10                  15

Ser Leu Arg Leu Ser Cys Arg Ala Ser Gln Ser Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Tyr Gly Ala Thr Ser Tyr Ala Glu
    50                  55                  60

Ser Val Lys Gly Arg Phe Ile Ile Ser Arg Asp Asp Asn Gly Thr Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 79
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 79
```

Glu Val Gln Leu Val Glu Ser Gly Gly Gly Leu Val Gln Pro Gly Gly
1               5                   10                  15

Ser Leu Arg Leu Ser Cys Ala Ala Ser Gln Ser Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Tyr Gly Ala Thr His Tyr Ala Glu
    50                  55                  60

Ser Val Lys Gly Arg Phe Ile Ile Ser Arg Asp Gly Asn Lys Asn Asp
65                  70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
                100                 105                 110

Gly Thr Leu Val Thr Val Ser
            115

<210> SEQ ID NO 80
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Arg Ala Ser Gln Phe Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Asn Gly Ala Thr His Tyr Ala Glu
    50                  55                  60

Ser Val Lys Gly Arg Phe Ile Ile Ser Arg Asp Gly Asn Gly Thr Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
                100                 105                 110

Gly Thr Leu Val Thr Val Ser
            115

<210> SEQ ID NO 81
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Arg Ala Ser Gly Ser Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Asn Ser Ala Thr Ser Tyr Ala Glu

```
                    50                  55                  60
Ser Val Lys Gly Arg Phe Ile Ile Ser Arg Asp Gly Asn Gly Thr Asp
 65                  70                  75                  80

Leu Thr Leu Glu Met Asn Ser Leu Lys Thr Glu Asp Thr Ala Glu Tyr
                 85                  90                  95

Tyr Cys Ala Gln Asn Tyr Tyr Gly Ser Thr Tyr Asp Tyr Trp Gly Gln
                100                 105                 110

Gly Thr Leu Val Thr Val Ser
        115

<210> SEQ ID NO 82
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 82

Glu Val Gln Leu Val Glu Ser Gly Gly Gly Leu Val Gln Pro Gly Gly
 1               5                  10                  15

Ser Leu Arg Leu Ser Cys Arg Ala Ser Gln Ser Ile Phe Ser Asn His
                 20                  25                  30

Tyr Met Asn Trp Val Arg Gln Ala Pro Gly Lys Gly Leu Glu Trp Ile
                 35                  40                  45

Gly Glu Ile Arg Ser Lys Ser Ile Tyr Ser Ala Thr His Tyr Ala Glu
             50                  55                  60

Ser Val Lys Gly Arg Phe Ile Ile Ser Arg Asp Gly Asn Gly Asn Asp
 65                  70                  75                  80

Leu Thr Leu Glu Met Asn Ser Leu Lys Thr Glu Asp Thr Ala Glu Tyr
                 85                  90                  95

Tyr Cys Ala Arg Asn Tyr Tyr Gly Ser Thr Pro Asp Tyr Trp Gly Gln
                100                 105                 110

Gly Thr Leu Val Thr Val Ser
        115

<210> SEQ ID NO 83
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 83

Glu Val Gln Leu Thr Glu Ser Gly Gly Gly Leu Val Gln Pro Gly Gly
 1               5                  10                  15

Ser Leu Arg Leu Ser Cys Arg Ala Ser Gly Phe Ile Phe Ser Asn His
                 20                  25                  30

Tyr Met Asn Trp Val Arg Gln Ala Pro Gly Lys Gly Leu Glu Trp Ile
                 35                  40                  45

Gly Glu Ile Arg Ser Lys Ser Ile Asn Gly Ala Thr Ser Tyr Ala Glu
             50                  55                  60

Ser Val Lys Gly Arg Phe Ile Ile Ser Arg Asp Asp Asn Gly Asn Ser
 65                  70                  75                  80

Leu Tyr Leu Glu Met Asn Ser Leu Lys Thr Glu Asp Thr Ala Glu Tyr
                 85                  90                  95

Tyr Cys Ala Arg Asn Tyr Tyr Gly Ser Thr Pro Asp Tyr Trp Gly Gln
                100                 105                 110
```

```
Gly Thr Leu Val Thr Val Ser
        115

<210> SEQ ID NO 84
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 84

Glu Val Gln Leu Val Glu Ser Gly Gly Leu Val Gln Pro Gly Gly
 1               5                  10                  15

Ser Leu Arg Leu Ser Cys Ala Ala Ser Gln Ser Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ser Tyr Ser Ala Thr His Tyr Ala Glu
    50                  55                  60

Ser Val Lys Gly Arg Phe Ile Ile Ser Arg Asp Gly Asn Lys Asn Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 85
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 85

Glu Val Gln Leu Thr Glu Ser Gly Gly Gly Leu Val Gln Pro Gly Gly
 1               5                  10                  15

Ser Leu Arg Leu Ser Cys Arg Ala Ser Gly Phe Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ser Asn Gly Ala Thr Ser Tyr Ala Glu
    50                  55                  60

Ser Val Lys Gly Arg Phe Ile Ile Ser Arg Asp Gly Asn Gly Thr Ser
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 86
<211> LENGTH: 119
<212> TYPE: PRT
<213> ORGANISM: Artificial Sequence
<220> FEATURE:
<223> OTHER INFORMATION: Infliximab VH variant
```

<400> SEQUENCE: 86

Glu Val Gln Leu Thr Glu Ser Gly Gly Gly Leu Val Gln Pro Gly Gly
1               5                   10                  15

Ser Leu Arg Leu Ser Cys Ala Ala Ser Gln Ser Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Tyr Gly Ala Thr His Tyr Ala Glu
    50                  55                  60

Ser Val Lys Gly Arg Phe Ile Ile Ser Arg Asp Asp Asn Gly Thr Asp
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 87
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Asn Ser Ala Thr His Tyr Ala Glu
    50                  55                  60

Ser Val Lys Gly Arg Phe Ile Ile Ser Arg Asp Gly Asn Lys Thr Ser
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 88
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Trp Met Asn Trp Val Arg Gln Ala Pro Gly Lys Gly Leu Glu Trp Ile
        35                  40                  45

```
Gly Glu Ile Arg Ser Lys Ser Ser Asn Ser Ala Thr Ser Tyr Ala Glu
        50                  55                  60

Ser Val Lys Gly Arg Phe Ile Ile Ser Arg Asp Gly Asn Lys Asn Asp
 65                  70                  75                  80

Leu Thr Leu Glu Met Asn Ser Leu Lys Thr Glu Asp Thr Ala Glu Tyr
                    85                  90                  95

Tyr Cys Ala Arg Asn Tyr Tyr Gly Ser Thr Tyr Asp Tyr Trp Gly Gln
                100                 105                 110

Gly Thr Leu Val Thr Val Ser
            115

<210> SEQ ID NO 89
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 89

Glu Val Gln Leu Val Glu Ser Gly Gly Gly Leu Val Gln Pro Gly Gly
 1               5                  10                  15

Ser Leu Arg Leu Ser Cys Arg Ala Ser Gln Phe Thr Phe Ser Asn His
                20                  25                  30

Tyr Met Asn Trp Val Arg Gln Ala Pro Gly Lys Gly Leu Glu Trp Ile
                35                  40                  45

Gly Glu Ile Arg Ser Lys Ser Ile Asn Gly Ala Thr Ser Tyr Ala Glu
        50                  55                  60

Ser Val Lys Gly Arg Phe Ile Ile Ser Arg Asp Asp Asn Gly Thr Asp
 65                  70                  75                  80

Leu Tyr Leu Glu Met Asn Ser Leu Lys Thr Glu Asp Thr Ala Glu Tyr
                    85                  90                  95

Tyr Cys Ala Arg Asn Tyr Tyr Gly Ser Thr Tyr Asp Tyr Trp Gly Gln
                100                 105                 110

Gly Thr Leu Val Thr Val Ser
            115

<210> SEQ ID NO 90
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 90

Glu Val Gln Leu Thr Glu Ser Gly Gly Gly Leu Val Gln Pro Gly Gly
 1               5                  10                  15

Ser Leu Arg Leu Ser Cys Arg Ala Ser Gln Phe Ile Phe Ser Asn His
                20                  25                  30

Tyr Met Asn Trp Val Arg Gln Ala Pro Gly Lys Gly Leu Glu Trp Ile
                35                  40                  45

Gly Glu Ile Arg Ser Lys Ser Ile Asn Gly Ala Thr His Tyr Ala Glu
        50                  55                  60

Ser Val Lys Gly Arg Phe Ile Ile Ser Arg Asp Asp Asn Gly Thr Asp
 65                  70                  75                  80

Leu Thr Leu Glu Met Asn Ser Leu Lys Thr Glu Asp Thr Ala Glu Tyr
                    85                  90                  95

Tyr Cys Ala Arg Asn Tyr Tyr Gly Ser Thr Pro Asp Tyr Trp Gly Gln
                100                 105                 110
```

Gly Thr Leu Val Thr Val Ser
        115

<210> SEQ ID NO 91
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 91

Glu Val Gln Leu Thr Glu Ser Gly Gly Gly Leu Val Gln Pro Gly Gly
  1               5                  10                  15

Ser Leu Arg Leu Ser Cys Ala Ala Ser Gln Ser Ile Phe Ser Asn His
             20                  25                  30

Tyr Met Asn Trp Val Arg Gln Ala Pro Gly Lys Gly Leu Glu Trp Ile
         35                  40                  45

Gly Glu Ile Arg Ser Lys Ser Ile Asn Ser Ala Thr His Tyr Ala Glu
     50                  55                  60

Ser Val Lys Gly Arg Phe Ile Ile Ser Arg Asp Gly Asn Lys Asn Asp
 65                  70                  75                  80

Leu Tyr Leu Glu Met Asn Ser Leu Lys Thr Glu Asp Thr Ala Glu Tyr
                 85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 92
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 92

Glu Val Gln Leu Val Glu Ser Gly Gly Gly Leu Val Gln Pro Gly Gly
  1               5                  10                  15

Ser Leu Arg Leu Ser Cys Ala Ala Ser Gly Ser Ile Phe Ser Asn His
             20                  25                  30

Trp Met Asn Trp Val Arg Gln Ala Pro Gly Lys Gly Leu Glu Trp Ile
         35                  40                  45

Gly Glu Ile Arg Ser Lys Ser Asn Ser Ala Thr His Tyr Ala Glu
     50                  55                  60

Ser Val Lys Gly Arg Phe Ile Ile Ser Arg Asp Gly Asn Lys Asn Asp
 65                  70                  75                  80

Leu Thr Leu Glu Met Asn Ser Leu Lys Thr Glu Asp Thr Ala Glu Tyr
                 85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 93
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 93

Glu Val Gln Leu Thr Glu Ser Gly Gly Gly Leu Val Gln Pro Gly Gly
1               5                   10                  15

Ser Leu Arg Leu Ser Cys Arg Ala Ser Gly Phe Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Tyr Gly Ala Thr His Tyr Ala Glu
    50                  55                  60

Ser Val Lys Gly Arg Phe Ile Ile Ser Arg Asp Asp Asn Gly Thr Asp
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 94
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Arg Ala Ser Gly Ser Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Asn Gly Ala Thr His Tyr Ala Glu
    50                  55                  60

Ser Val Lys Gly Arg Phe Ile Ile Ser Arg Asp Asp Asn Gly Thr Ser
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 95
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 95

Glu Val Gln Leu Thr Glu Ser Gly Gly Gly Leu Val Gln Pro Gly Gly
1               5                   10                  15

Ser Leu Arg Leu Ser Cys Arg Ala Ser Gly Ser Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Asn Ser Ala Thr Ser Tyr Ala Glu
            50                  55                  60

Ser Val Lys Gly Arg Phe Ile Ile Ser Arg Asp Asp Asn Lys Thr Ser
 65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 96
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 96

Glu Val Gln Leu Val Glu Ser Gly Gly Gly Leu Val Gln Pro Gly Gly
 1               5                   10                  15

Ser Leu Arg Leu Ser Cys Arg Ala Ser Gln Ser Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Asn Ser Ala Thr His Tyr Ala Glu
            50                  55                  60

Ser Val Lys Gly Arg Phe Ile Ile Ser Arg Asp Asp Asn Gly Asn Ser
 65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 97
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 97

Glu Val Gln Leu Thr Glu Ser Gly Gly Gly Leu Val Gln Pro Gly Gly
 1               5                   10                  15

Ser Leu Arg Leu Ser Cys Arg Ala Ser Gly Ser Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ser Asn Gly Ala Thr Ser Tyr Ala Glu
            50                  55                  60

Ser Val Lys Gly Arg Phe Ile Ile Ser Arg Asp Asp Asn Gly Thr Asp
 65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln

Gly Thr Leu Val Thr Val Ser
        115

<210> SEQ ID NO 98
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 98

Glu Val Gln Leu Thr Glu Ser Gly Gly Gly Leu Val Gln Pro Gly Gly
1               5                   10                  15

Ser Leu Arg Leu Ser Cys Arg Ala Ser Gly Phe Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ser Asn Gly Ala Thr His Tyr Ala Glu
    50                  55                  60

Ser Val Lys Gly Arg Phe Ile Ile Ser Arg Asp Gly Asn Lys Thr Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 99
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Asn Gly Ala Thr His Tyr Ala Glu
    50                  55                  60

Ser Val Lys Gly Arg Phe Ile Ile Ser Arg Asp Asp Asn Lys Asn Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 100
<211> LENGTH: 119
<212> TYPE: PRT
<213> ORGANISM: Artificial Sequence
<220> FEATURE:

<223> OTHER INFORMATION: Infliximab VH variant

<400> SEQUENCE: 100

Glu Val Gln Leu Thr Glu Ser Gly Gly Gly Leu Val Gln Pro Gly Gly
1               5                   10                  15

Ser Leu Arg Leu Ser Cys Arg Ala Ser Gln Phe Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Asn Gly Ala Thr His Tyr Ala Glu
    50                  55                  60

Ser Val Lys Gly Arg Phe Ile Ile Ser Arg Asp Asp Asn Lys Thr Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 101
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Arg Ala Ser Gly Phe Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Asn Ser Ala Thr Ser Tyr Ala Glu
    50                  55                  60

Ser Val Lys Gly Arg Phe Ile Ile Ser Arg Asp Asp Asn Gly Asn Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 102
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 102

Glu Val Gln Leu Val Glu Ser Gly Gly Gly Leu Val Gln Pro Gly Gly
1               5                   10                  15

Ser Leu Arg Leu Ser Cys Arg Ala Ser Gly Phe Ile Phe Ser Asn His
            20                  25                  30

Trp Met Asn Trp Val Arg Gln Ala Pro Gly Lys Gly Leu Glu Trp Ile

```
                35                  40                  45
Gly Glu Ile Arg Ser Lys Ser Ile Asn Gly Ala Thr His Tyr Ala Glu
        50                  55                  60
Ser Val Lys Gly Arg Phe Ile Ile Ser Arg Asp Asp Asn Lys Thr Ser
65                  70                  75                  80
Leu Tyr Leu Glu Met Asn Ser Leu Lys Thr Glu Asp Thr Ala Glu Tyr
                85                  90                  95
Tyr Cys Ala Arg Asn Tyr Tyr Gly Ser Thr Tyr Asp Tyr Trp Gly Gln
                100                 105                 110
Gly Thr Leu Val Thr Val Ser
            115

<210> SEQ ID NO 103
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 103

Glu Val Gln Leu Thr Glu Ser Gly Gly Gly Leu Val Gln Pro Gly Gly
1               5                   10                  15
Ser Leu Arg Leu Ser Cys Ala Ala Ser Gln Ser Thr Phe Ser Asn His
            20                  25                  30
Trp Met Asn Trp Val Arg Gln Ala Pro Gly Lys Gly Leu Glu Trp Ile
        35                  40                  45
Gly Glu Ile Arg Ser Lys Ser Ile Asn Gly Ala Thr Ser Tyr Ala Glu
        50                  55                  60
Ser Val Lys Gly Arg Phe Ile Ile Ser Arg Asp Asp Asn Gly Asn Ser
65                  70                  75                  80
Leu Thr Leu Glu Met Asn Ser Leu Lys Thr Glu Asp Thr Ala Glu Tyr
                85                  90                  95
Tyr Cys Ala Arg Asn Tyr Tyr Gly Ser Thr Pro Asp Tyr Trp Gly Gln
                100                 105                 110
Gly Thr Leu Val Thr Val Ser
            115

<210> SEQ ID NO 104
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 104

Glu Val Gln Leu Thr Glu Ser Gly Gly Gly Leu Val Gln Pro Gly Gly
1               5                   10                  15
Ser Leu Arg Leu Ser Cys Arg Ala Ser Gln Phe Ile Phe Ser Asn His
            20                  25                  30
Tyr Met Asn Trp Val Arg Gln Ala Pro Gly Lys Gly Leu Glu Trp Ile
        35                  40                  45
Gly Glu Ile Arg Ser Lys Ser Ile Asn Ser Ala Thr His Tyr Ala Glu
        50                  55                  60
Ser Val Lys Gly Arg Phe Ile Ile Ser Arg Asp Asp Asn Lys Asn Asp
65                  70                  75                  80
Leu Tyr Leu Glu Met Asn Ser Leu Lys Thr Glu Asp Thr Ala Glu Tyr
                85                  90                  95
```

-continued

Tyr Cys Ala Gln Asn Tyr Tyr Gly Ser Thr Pro Asp Tyr Trp Gly Gln
                100                 105                 110

Gly Thr Leu Val Thr Val Ser
        115

<210> SEQ ID NO 105
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 105

Glu Val Gln Leu Thr Glu Ser Gly Gly Gly Leu Val Gln Pro Gly Gly
1               5                   10                  15

Ser Leu Arg Leu Ser Cys Ala Ala Ser Gly Phe Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Asn Gly Ala Thr Ser Tyr Ala Glu
    50                  55                  60

Ser Val Lys Gly Arg Phe Ile Ile Ser Arg Asp Asp Asn Gly Asn Ser
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
                100                 105                 110

Gly Thr Leu Val Thr Val Ser
        115

<210> SEQ ID NO 106
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Gln Phe Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ser Asn Gly Ala Thr Ser Tyr Ala Glu
    50                  55                  60

Ser Val Lys Gly Arg Phe Ile Ile Ser Arg Asp Gly Asn Lys Thr Asp
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
                100                 105                 110

Gly Thr Leu Val Thr Val Ser
        115

<210> SEQ ID NO 107
<211> LENGTH: 119
<212> TYPE: PRT
<213> ORGANISM: Artificial Sequence

```
<220> FEATURE:
<223> OTHER INFORMATION: Infliximab VH variant

<400> SEQUENCE: 107

Glu Val Gln Leu Thr Glu Ser Gly Gly Gly Leu Val Gln Pro Gly Gly
 1               5                   10                  15

Ser Leu Arg Leu Ser Cys Arg Ala Ser Gln Ser Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Asn Ser Ala Thr His Tyr Ala Glu
    50                  55                  60

Ser Val Lys Gly Arg Phe Ile Ile Ser Arg Asp Gly Asn Lys Thr Asp
65                  70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 108
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 108

Glu Val Gln Leu Thr Glu Ser Gly Gly Gly Leu Val Gln Pro Gly Gly
 1               5                   10                  15

Ser Leu Arg Leu Ser Cys Ala Ala Ser Gln Phe Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Tyr Ser Ala Thr Ser Tyr Ala Glu
    50                  55                  60

Ser Val Lys Gly Arg Phe Ile Ile Ser Arg Asp Gly Asn Lys Asn Ser
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 109
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 109

Glu Val Gln Leu Val Glu Ser Gly Gly Gly Leu Val Gln Pro Gly Gly
 1               5                   10                  15

Ser Leu Arg Leu Ser Cys Arg Ala Ser Gly Ser Ile Phe Ser Asn His
            20                  25                  30
```

```
Trp Met Asn Trp Val Arg Gln Ala Pro Gly Lys Gly Leu Glu Trp Ile
        35                  40                  45

Gly Glu Ile Arg Ser Lys Ser Ser Asn Ser Ala Thr His Tyr Ala Glu
 50                  55                  60

Ser Val Lys Gly Arg Phe Ile Ile Ser Arg Asp Asp Asn Lys Asn Asp
 65                  70                  75                  80

Leu Thr Leu Glu Met Asn Ser Leu Lys Thr Glu Asp Thr Ala Glu Tyr
                 85                  90                  95

Tyr Cys Ala Arg Asn Tyr Tyr Gly Ser Thr Tyr Asp Tyr Trp Gly Gln
                100                 105                 110

Gly Thr Leu Val Thr Val Ser
        115
```

```
<210> SEQ ID NO 110
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 110

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Phe Ser Asn His
                 20                  25                  30

Trp Met Asn Trp Val Arg Gln Ala Pro Gly Lys Gly Leu Glu Trp Ile
        35                  40                  45

Gly Glu Ile Arg Ser Lys Ser Ile Asn Ser Ala Thr Ser Tyr Ala Glu
 50                  55                  60

Ser Val Lys Gly Arg Phe Ile Ile Ser Arg Asp Asp Asn Lys Thr Asp
 65                  70                  75                  80

Leu Tyr Leu Glu Met Asn Ser Leu Lys Thr Glu Asp Thr Ala Glu Tyr
                 85                  90                  95

Tyr Cys Ala Gln Asn Tyr Tyr Gly Ser Thr Pro Asp Tyr Trp Gly Gln
                100                 105                 110

Gly Thr Leu Val Thr Val Ser
        115
```

```
<210> SEQ ID NO 111
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 111

Glu Val Gln Leu Thr Glu Ser Gly Gly Gly Leu Val Gln Pro Gly Gly
 1               5                  10                  15

Ser Leu Arg Leu Ser Cys Arg Ala Ser Gly Phe Ile Phe Ser Asn His
                 20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Asn Ser Ala Thr His Tyr Ala Glu
 50                  55                  60

Ser Val Lys Gly Arg Phe Ile Ile Ser Arg Asp Asp Asn Gly Asn Ser
 65                  70                  75                  80

Leu Tyr Leu Glu Met Asn Ser Leu Lys Thr Glu Asp Thr Ala Glu Tyr
                 85                  90                  95
```

```
Tyr Cys Ala Arg Asn Tyr Tyr Gly Ser Thr Pro Asp Tyr Trp Gly Gln
            100                 105                 110

Gly Thr Leu Val Thr Val Ser
        115
```

<210> SEQ ID NO 112
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 112

```
Glu Val Gln Leu Val Glu Ser Gly Gly Gly Leu Val Gln Pro Gly Gly
 1               5                  10                  15

Ser Leu Arg Leu Ser Cys Arg Ala Ser Gly Phe Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Tyr Ser Ala Thr His Tyr Ala Glu
    50                  55                  60

Ser Val Lys Gly Arg Phe Ile Ile Ser Arg Asp Asp Asn Lys Thr Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115
```

<210> SEQ ID NO 113
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 113

```
Glu Val Gln Leu Val Glu Ser Gly Gly Gly Leu Val Gln Pro Gly Gly
 1               5                  10                  15

Ser Leu Arg Leu Ser Cys Arg Ala Ser Gln Phe Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Tyr Gly Ala Thr His Tyr Ala Glu
    50                  55                  60

Ser Val Lys Gly Arg Phe Ile Ile Ser Arg Asp Gly Asn Gly Thr Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115
```

<210> SEQ ID NO 114
<211> LENGTH: 119
<212> TYPE: PRT

<213> ORGANISM: Artificial Sequence
<220> FEATURE:
<223> OTHER INFORMATION: Infliximab VH variant

<400> SEQUENCE: 114

Glu Val Gln Leu Thr Glu Ser Gly Gly Gly Leu Val Gln Pro Gly Gly
1               5                   10                  15

Ser Leu Arg Leu Ser Cys Arg Ala Ser Gln Ser Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Asn Ser Ala Thr Ser Tyr Ala Glu
    50                  55                  60

Ser Val Lys Gly Arg Phe Ile Ile Ser Arg Asp Gly Asn Lys Asn Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 115
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Arg Ala Ser Gly Ser Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Asn Ser Ala Thr His Tyr Ala Glu
    50                  55                  60

Ser Val Lys Gly Arg Phe Ile Ile Ser Arg Asp Gly Asn Gly Thr Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 116
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 116

Glu Val Gln Leu Thr Glu Ser Gly Gly Gly Leu Val Gln Pro Gly Gly
1               5                   10                  15

Ser Leu Arg Leu Ser Cys Ala Ala Ser Gln Ser Thr Phe Ser Asn His
            20                  25                  30

```
Trp Met Asn Trp Val Arg Gln Ala Pro Gly Lys Gly Leu Glu Trp Ile
            35                  40                  45

Gly Glu Ile Arg Ser Lys Ser Ile Asn Gly Ala Thr His Tyr Ala Glu
 50                  55                  60

Ser Val Lys Gly Arg Phe Ile Ile Ser Arg Asp Asp Asn Gly Asn Asp
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
                100                 105                 110

Gly Thr Leu Val Thr Val Ser
            115

<210> SEQ ID NO 117
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 117

Glu Val Gln Leu Thr Glu Ser Gly Gly Gly Leu Val Gln Pro Gly Gly
 1               5                  10                  15

Ser Leu Arg Leu Ser Cys Ala Ala Ser Gln Phe Thr Phe Ser Asn His
            20                  25                  30

Trp Met Asn Trp Val Arg Gln Ala Pro Gly Lys Gly Leu Glu Trp Ile
            35                  40                  45

Gly Glu Ile Arg Ser Lys Ser Ser Asn Ser Ala Thr His Tyr Ala Glu
 50                  55                  60

Ser Val Lys Gly Arg Phe Ile Ile Ser Arg Asp Gly Asn Lys Thr Ser
65                  70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
                100                 105                 110

Gly Thr Leu Val Thr Val Ser
            115

<210> SEQ ID NO 118
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 118

Glu Val Gln Leu Val Glu Ser Gly Gly Gly Leu Val Gln Pro Gly Gly
 1               5                  10                  15

Ser Leu Arg Leu Ser Cys Ala Ala Ser Gln Phe Thr Phe Ser Asn His
            20                  25                  30

Trp Met Asn Trp Val Arg Gln Ala Pro Gly Lys Gly Leu Glu Trp Ile
            35                  40                  45

Gly Glu Ile Arg Ser Lys Ser Ile Asn Ser Ala Thr Ser Tyr Ala Glu
 50                  55                  60

Ser Val Lys Gly Arg Phe Ile Ile Ser Arg Asp Asp Asn Lys Asn Ser
65                  70                  75                  80

Leu Tyr Leu Glu Met Asn Ser Leu Lys Thr Glu Asp Thr Ala Glu Tyr
```

-continued

```
                85                  90                  95
Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 119
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 119

Glu Val Gln Leu Thr Glu Ser Gly Gly Gly Leu Val Gln Pro Gly Gly
1               5                   10                  15

Ser Leu Arg Leu Ser Cys Arg Ala Ser Gln Ser Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Tyr Gly Ala Thr Ser Tyr Ala Glu
    50                  55                  60

Ser Val Lys Gly Arg Phe Ile Ile Ser Arg Asp Gly Asn Lys Thr Asp
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 120
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 120

Glu Val Gln Leu Thr Glu Ser Gly Gly Gly Leu Val Gln Pro Gly Gly
1               5                   10                  15

Ser Leu Arg Leu Ser Cys Arg Ala Ser Gln Ser Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Tyr Ser Ala Thr His Tyr Ala Glu
    50                  55                  60

Ser Val Lys Gly Arg Phe Ile Ile Ser Arg Asp Gly Asn Gly Asn Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 121
<211> LENGTH: 119
```

```
<212> TYPE: PRT
<213> ORGANISM: Artificial Sequence
<220> FEATURE:
<223> OTHER INFORMATION: Infliximab VH variant

<400> SEQUENCE: 121

Glu Val Gln Leu Val Glu Ser Gly Gly Gly Leu Val Gln Pro Gly Gly
  1               5                  10                  15

Ser Leu Arg Leu Ser Cys Ala Ala Ser Gln Phe Thr Phe Ser Asn His
             20                  25                  30

Tyr Met Asn Trp Val Arg Gln Ala Pro Gly Lys Gly Leu Glu Trp Ile
         35                  40                  45

Gly Glu Ile Arg Ser Lys Ser Ile Asn Ser Ala Thr His Tyr Ala Glu
     50                  55                  60

Ser Val Lys Gly Arg Phe Ile Ile Ser Arg Asp Asp Asn Gly Asn Asp
 65                  70                  75                  80

Leu Tyr Leu Glu Met Asn Ser Leu Lys Thr Glu Asp Thr Ala Glu Tyr
                 85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
            115

<210> SEQ ID NO 122
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 122

Glu Val Gln Leu Thr Glu Ser Gly Gly Gly Leu Val Gln Pro Gly Gly
  1               5                  10                  15

Ser Leu Arg Leu Ser Cys Arg Ala Ser Gln Phe Ile Phe Ser Asn His
             20                  25                  30

Tyr Met Asn Trp Val Arg Gln Ala Pro Gly Lys Gly Leu Glu Trp Ile
         35                  40                  45

Gly Glu Ile Arg Ser Lys Ser Ile Asn Ser Ala Thr Ser Tyr Ala Glu
     50                  55                  60

Ser Val Lys Gly Arg Phe Ile Ile Ser Arg Asp Gly Asn Gly Asn Asp
 65                  70                  75                  80

Leu Thr Leu Glu Met Asn Ser Leu Lys Thr Glu Asp Thr Ala Glu Tyr
                 85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
            115

<210> SEQ ID NO 123
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 123

Glu Val Gln Leu Thr Glu Ser Gly Gly Gly Leu Val Gln Pro Gly Gly
  1               5                  10                  15

Ser Leu Arg Leu Ser Cys Arg Ala Ser Gln Phe Thr Phe Ser Asn His
```

```
                    20                  25                  30
Tyr Met Asn Trp Val Arg Gln Ala Pro Gly Lys Gly Leu Glu Trp Ile
            35                  40                  45

Gly Glu Ile Arg Ser Lys Ser Ser Tyr Gly Ala Thr Ser Tyr Ala Glu
 50                  55                  60

Ser Val Lys Gly Arg Phe Ile Ile Ser Arg Asp Asp Asn Gly Asn Asp
 65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
                100                 105                 110

Gly Thr Leu Val Thr Val Ser
        115

<210> SEQ ID NO 124
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 124

Glu Val Gln Leu Val Glu Ser Gly Gly Gly Leu Val Gln Pro Gly Gly
 1               5                  10                  15

Ser Leu Arg Leu Ser Cys Ala Ala Ser Gln Ser Thr Phe Ser Asn His
            20                  25                  30

Tyr Met Asn Trp Val Arg Gln Ala Pro Gly Lys Gly Leu Glu Trp Ile
            35                  40                  45

Gly Glu Ile Arg Ser Lys Ser Ser Asn Ser Ala Thr His Tyr Ala Glu
 50                  55                  60

Ser Val Lys Gly Arg Phe Ile Ile Ser Arg Asp Gly Asn Lys Asn Asp
 65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
                100                 105                 110

Gly Thr Leu Val Thr Val Ser
        115

<210> SEQ ID NO 125
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 125

Glu Val Gln Leu Thr Glu Ser Gly Gly Gly Leu Val Gln Pro Gly Gly
 1               5                  10                  15

Ser Leu Arg Leu Ser Cys Ala Ala Ser Gln Phe Thr Phe Ser Asn His
            20                  25                  30

Tyr Met Asn Trp Val Arg Gln Ala Pro Gly Lys Gly Leu Glu Trp Ile
            35                  40                  45

Gly Glu Ile Arg Ser Lys Ser Ile Asn Gly Ala Thr Ser Tyr Ala Glu
 50                  55                  60

Ser Val Lys Gly Arg Phe Ile Ile Ser Arg Asp Asp Asn Gly Thr Ser
 65                  70                  75                  80
```

Leu Thr Leu Glu Met Asn Ser Leu Lys Thr Glu Asp Thr Ala Glu Tyr
            85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 126
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Arg Ala Ser Gly Ser Thr Phe Ser Asn His
            20                  25                  30

Tyr Met Asn Trp Val Arg Gln Ala Pro Gly Lys Gly Leu Glu Trp Ile
            35                  40                  45

Gly Glu Ile Arg Ser Lys Ser Ile Tyr Ser Ala Thr His Tyr Ala Glu
        50                  55                  60

Ser Val Lys Gly Arg Phe Ile Ile Ser Arg Asp Gly Asn Lys Asn Ser
65                  70                  75                  80

Leu Tyr Leu Glu Met Asn Ser Leu Lys Thr Glu Asp Thr Ala Glu Tyr
            85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 127
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 127

Glu Val Gln Leu Thr Glu Ser Gly Gly Gly Leu Val Gln Pro Gly Gly
1               5                   10                  15

Ser Leu Arg Leu Ser Cys Ala Ala Ser Gln Phe Ile Phe Ser Asn His
            20                  25                  30

Trp Met Asn Trp Val Arg Gln Ala Pro Gly Lys Gly Leu Glu Trp Ile
            35                  40                  45

Gly Glu Ile Arg Ser Lys Ser Tyr Gly Ala Thr Ser Tyr Ala Glu
        50                  55                  60

Ser Val Lys Gly Arg Phe Ile Ile Ser Arg Asp Asp Asn Gly Asn Ser
65                  70                  75                  80

Leu Thr Leu Glu Met Asn Ser Leu Lys Thr Glu Asp Thr Ala Glu Tyr
            85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 128

```
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 128

Glu Val Gln Leu Val Glu Ser Gly Gly Gly Leu Val Gln Pro Gly Gly
 1               5                  10                  15

Ser Leu Arg Leu Ser Cys Arg Ala Ser Gln Ser Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Asn Ser Ala Thr Ser Tyr Ala Glu
    50                  55                  60

Ser Val Lys Gly Arg Phe Ile Ile Ser Arg Asp Asp Asn Gly Asn Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 129
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 129

Glu Val Gln Leu Val Glu Ser Gly Gly Gly Leu Val Gln Pro Gly Gly
 1               5                  10                  15

Ser Leu Arg Leu Ser Cys Ala Ala Ser Gln Ser Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ser Tyr Gly Ala Thr His Tyr Ala Glu
    50                  55                  60

Ser Val Lys Gly Arg Phe Ile Ile Ser Arg Asp Gly Asn Gly Thr Ser
65                  70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 130
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 130

Glu Val Gln Leu Val Glu Ser Gly Gly Gly Leu Val Gln Pro Gly Gly
 1               5                  10                  15
```

```
Ser Leu Arg Leu Ser Cys Arg Ala Ser Gly Phe Ile Phe Ser Asn His
            20                  25                  30

Tyr Met Asn Trp Val Arg Gln Ala Pro Gly Lys Gly Leu Glu Trp Ile
            35                  40                  45

Gly Glu Ile Arg Ser Lys Ser Ile Tyr Ser Ala Thr His Tyr Ala Glu
        50                  55                  60

Ser Val Lys Gly Arg Phe Ile Ile Ser Arg Asp Asp Asn Gly Asn Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 131
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 131

Glu Val Gln Leu Thr Glu Ser Gly Gly Gly Leu Val Gln Pro Gly Gly
1               5                   10                  15

Ser Leu Arg Leu Ser Cys Ala Ala Ser Gln Phe Thr Phe Ser Asn His
            20                  25                  30

Tyr Met Asn Trp Val Arg Gln Ala Pro Gly Lys Gly Leu Glu Trp Ile
            35                  40                  45

Gly Glu Ile Arg Ser Lys Ser Ser Asn Ser Ala Thr Ser Tyr Ala Glu
        50                  55                  60

Ser Val Lys Gly Arg Phe Ile Ile Ser Arg Asp Gly Asn Gly Thr Ser
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 132
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Ala Ser Gln Ser Ile Phe Ser Asn His
            20                  25                  30

Tyr Met Asn Trp Val Arg Gln Ala Pro Gly Lys Gly Leu Glu Trp Ile
            35                  40                  45

Gly Glu Ile Arg Ser Lys Ser Ile Tyr Gly Ala Thr Ser Tyr Ala Glu
        50                  55                  60

Ser Val Lys Gly Arg Phe Ile Ile Ser Arg Asp Asp Asn Lys Asn Ser
65                  70                  75                  80
```

```
Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 133
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 133

Glu Val Gln Leu Val Glu Ser Gly Gly Gly Leu Val Gln Pro Gly Gly
  1               5                  10                  15

Ser Leu Arg Leu Ser Cys Ala Ala Ser Gln Ser Thr Phe Ser Asn His
             20                  25                  30

Tyr Met Asn Trp Val Arg Gln Ala Pro Gly Lys Gly Leu Glu Trp Ile
         35                  40                  45

Gly Glu Ile Arg Ser Lys Ser Ser Tyr Gly Ala Thr His Tyr Ala Glu
     50                  55                  60

Ser Val Lys Gly Arg Phe Ile Ile Ser Arg Asp Asp Asn Lys Asn Asp
 65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 134
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 134

Glu Val Gln Leu Thr Glu Ser Gly Gly Gly Leu Val Gln Pro Gly Gly
  1               5                  10                  15

Ser Leu Arg Leu Ser Cys Ala Ala Ser Gly Ser Ile Phe Ser Asn His
             20                  25                  30

Trp Met Asn Trp Val Arg Gln Ala Pro Gly Lys Gly Leu Glu Trp Ile
         35                  40                  45

Gly Glu Ile Arg Ser Lys Ser Ile Asn Gly Ala Thr His Tyr Ala Glu
     50                  55                  60

Ser Val Lys Gly Arg Phe Ile Ile Ser Arg Asp Gly Asn Gly Thr Ser
 65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115
```

```
<210> SEQ ID NO 135
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 135

Glu Val Gln Leu Val Glu Ser Gly Gly Gly Leu Val Gln Pro Gly Gly
 1               5                  10                  15

Ser Leu Arg Leu Ser Cys Ala Ala Ser Gln Ser Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ser Asn Ser Ala Thr Ser Tyr Ala Glu
    50                  55                  60

Ser Val Lys Gly Arg Phe Ile Ile Ser Arg Asp Gly Asn Lys Thr Asp
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 136
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 136

Glu Val Gln Leu Thr Glu Ser Gly Gly Gly Leu Val Gln Pro Gly Gly
 1               5                  10                  15

Ser Leu Arg Leu Ser Cys Ala Ala Ser Gln Ser Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Tyr Ser Ala Thr His Tyr Ala Glu
    50                  55                  60

Ser Val Lys Gly Arg Phe Ile Ile Ser Arg Asp Asp Asn Gly Thr Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 137
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 137

Glu Val Gln Leu Val Glu Ser Gly Gly Gly Leu Val Gln Pro Gly Gly
 1               5                  10                  15
```

Ser Leu Arg Leu Ser Cys Ala Ala Ser Gly Ser Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Tyr Ser Ala Thr Ser Tyr Ala Glu
    50                  55                  60

Ser Val Lys Gly Arg Phe Ile Ile Ser Arg Asp Gly Asn Gly Thr Asp
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
            115

<210> SEQ ID NO 138
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 138

Glu Val Gln Leu Thr Glu Ser Gly Gly Gly Leu Val Gln Pro Gly Gly
1               5                   10                  15

Ser Leu Arg Leu Ser Cys Arg Ala Ser Gly Phe Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Asn Ser Ala Thr Ser Tyr Ala Glu
    50                  55                  60

Ser Val Lys Gly Arg Phe Ile Ile Ser Arg Asp Gly Asn Lys Asn Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
            115

<210> SEQ ID NO 139
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 139

Glu Val Gln Leu Thr Glu Ser Gly Gly Gly Leu Val Gln Pro Gly Gly
1               5                   10                  15

Ser Leu Arg Leu Ser Cys Arg Ala Ser Gln Ser Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Tyr Gly Ala Thr Ser Tyr Ala Glu
    50                  55                  60

Ser Val Lys Gly Arg Phe Ile Ile Ser Arg Asp Asp Asn Lys Asn Ser

```
              65                  70                  75                  80
Leu Thr Leu Glu Met Asn Ser Leu Lys Thr Glu Asp Thr Ala Glu Tyr
                    85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 140
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 140

Glu Val Gln Leu Thr Glu Ser Gly Gly Gly Leu Val Gln Pro Gly Gly
 1               5                  10                  15

Ser Leu Arg Leu Ser Cys Ala Ala Ser Gly Ser Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Asn Ser Ala Thr His Tyr Ala Glu
    50                  55                  60

Ser Val Lys Gly Arg Phe Ile Ile Ser Arg Asp Asp Asn Gly Thr Ser
65                  70                  75                  80

Leu Tyr Leu Glu Met Asn Ser Leu Lys Thr Glu Asp Thr Ala Glu Tyr
                    85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 141
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 141

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Tyr Gly Ala Thr Ser Tyr Ala Glu
    50                  55                  60

Ser Val Lys Gly Arg Phe Ile Ile Ser Arg Asp Gly Asn Lys Asn Ser
65                  70                  75                  80

Leu Tyr Leu Glu Met Asn Ser Leu Lys Thr Glu Asp Thr Ala Glu Tyr
                    85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115
```

```
<210> SEQ ID NO 142
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 142

Glu Val Gln Leu Val Glu Ser Gly Gly Gly Leu Val Gln Pro Gly Gly
 1               5                  10                  15

Ser Leu Arg Leu Ser Cys Arg Ala Ser Gln Phe Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Tyr Ser Ala Thr Ser Tyr Ala Glu
    50                  55                  60

Ser Val Lys Gly Arg Phe Ile Ile Ser Arg Asp Asp Asn Gly Thr Ser
65                  70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 143
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 143

Glu Val Gln Leu Val Glu Ser Gly Gly Gly Leu Val Gln Pro Gly Gly
 1               5                  10                  15

Ser Leu Arg Leu Ser Cys Ala Ala Ser Gln Ser Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Asn Ser Ala Thr Ser Tyr Ala Glu
    50                  55                  60

Ser Val Lys Gly Arg Phe Ile Ile Ser Arg Asp Gly Asn Gly Asn Asp
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 144
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 144

Glu Val Gln Leu Val Glu Ser Gly Gly Gly Leu Val Gln Pro Gly Gly
```

```
                1               5                   10                  15
Ser Leu Arg Leu Ser Cys Arg Ala Ser Gly Ser Ile Phe Ser Asn His
                20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Asn Ser Ala Thr Ser Tyr Ala Glu
        50                  55                  60

Ser Val Lys Gly Arg Phe Ile Ile Ser Arg Asp Gly Asn Lys Asn Asp
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
                100                 105                 110

Gly Thr Leu Val Thr Val Ser
        115

<210> SEQ ID NO 145
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 145

Glu Val Gln Leu Thr Glu Ser Gly Gly Gly Leu Val Gln Pro Gly Gly
1               5                   10                  15

Ser Leu Arg Leu Ser Cys Arg Ala Ser Gln Ser Thr Phe Ser Asn His
                20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Asn Gly Ala Thr Ser Tyr Ala Glu
        50                  55                  60

Ser Val Lys Gly Arg Phe Ile Ile Ser Arg Asp Asp Asn Gly Asn Asp
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
                100                 105                 110

Gly Thr Leu Val Thr Val Ser
        115

<210> SEQ ID NO 146
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Asn His
                20                  25                  30

Trp Met Asn Trp Val Arg Gln Ala Pro Gly Lys Gly Leu Glu Trp Ile
        35                  40                  45

Gly Glu Ile Arg Ser Lys Ser Ile Asn Gly Ala Thr His Tyr Ala Glu
        50                  55                  60
```

```
Ser Val Lys Gly Arg Phe Ile Ile Ser Arg Asp Gly Asn Lys Asn Asp
 65                  70                  75                  80

Leu Thr Leu Glu Met Asn Ser Leu Lys Thr Glu Asp Thr Ala Glu Tyr
                 85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 147
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 147

Glu Val Gln Leu Val Glu Ser Gly Gly Gly Leu Val Gln Pro Gly Gly
  1               5                  10                  15

Ser Leu Arg Leu Ser Cys Ala Ala Ser Gln Ser Ile Phe Ser Asn His
                20                  25                  30

Trp Met Asn Trp Val Arg Gln Ala Pro Gly Lys Gly Leu Glu Trp Ile
             35                  40                  45

Gly Glu Ile Arg Ser Lys Ser Ile Asn Ser Ala Thr His Tyr Ala Glu
 50                  55                  60

Ser Val Lys Gly Arg Phe Ile Ile Ser Arg Asp Gly Asn Gly Thr Asp
 65                  70                  75                  80

Leu Thr Leu Glu Met Asn Ser Leu Lys Thr Glu Asp Thr Ala Glu Tyr
                 85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 148
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 148

Glu Val Gln Leu Val Glu Ser Gly Gly Gly Leu Val Gln Pro Gly Gly
  1               5                  10                  15

Ser Leu Arg Leu Ser Cys Arg Ala Ser Gln Phe Ile Phe Ser Asn His
                20                  25                  30

Tyr Met Asn Trp Val Arg Gln Ala Pro Gly Lys Gly Leu Glu Trp Ile
             35                  40                  45

Gly Glu Ile Arg Ser Lys Ser Ile Tyr Gly Ala Thr Ser Tyr Ala Glu
 50                  55                  60

Ser Val Lys Gly Arg Phe Ile Ile Ser Arg Asp Gly Asn Gly Asn Asp
 65                  70                  75                  80

Leu Tyr Leu Glu Met Asn Ser Leu Lys Thr Glu Asp Thr Ala Glu Tyr
                 85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115
```

```
<210> SEQ ID NO 149
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 149

Glu Val Gln Leu Thr Glu Ser Gly Gly Gly Leu Val Gln Pro Gly Gly
 1               5                  10                  15

Ser Leu Arg Leu Ser Cys Arg Ala Ser Gln Phe Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Tyr Ser Ala Thr His Tyr Ala Glu
    50                  55                  60

Ser Val Lys Gly Arg Phe Ile Ile Ser Arg Asp Asp Asn Gly Asn Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 150
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 150

Glu Val Gln Leu Val Glu Ser Gly Gly Gly Leu Val Gln Pro Gly Gly
 1               5                  10                  15

Ser Leu Arg Leu Ser Cys Ala Ala Ser Gln Phe Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Asn Gly Ala Thr Ser Tyr Ala Glu
    50                  55                  60

Ser Val Lys Gly Arg Phe Ile Ile Ser Arg Asp Asp Asn Gly Thr Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 151
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 151
```

-continued

```
Glu Val Gln Leu Val Glu Ser Gly Gly Gly Leu Val Gln Pro Gly Gly
  1               5                   10                  15

Ser Leu Arg Leu Ser Cys Ala Ala Ser Gln Phe Ile Phe Ser Asn His
             20                  25                  30

Tyr Met Asn Trp Val Arg Gln Ala Pro Gly Lys Gly Leu Glu Trp Ile
         35                  40                  45

Gly Glu Ile Arg Ser Lys Ser Ile Tyr Gly Ala Thr His Tyr Ala Glu
     50                  55                  60

Ser Val Lys Gly Arg Phe Ile Ile Ser Arg Asp Gly Asn Gly Asn Ser
 65                  70                  75                  80

Leu Thr Leu Glu Met Asn Ser Leu Lys Thr Glu Asp Thr Ala Glu Tyr
                 85                  90                  95

Tyr Cys Ala Arg Asn Tyr Tyr Gly Ser Thr Pro Asp Tyr Trp Gly Gln
             100                 105                 110

Gly Thr Leu Val Thr Val Ser
         115

<210> SEQ ID NO 152
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 152

Glu Val Gln Leu Val Glu Ser Gly Gly Gly Leu Val Gln Pro Gly Gly
  1               5                   10                  15

Ser Leu Arg Leu Ser Cys Ala Ala Ser Gln Phe Thr Phe Ser Asn His
             20                  25                  30

Tyr Met Asn Trp Val Arg Gln Ala Pro Gly Lys Gly Leu Glu Trp Ile
         35                  40                  45

Gly Glu Ile Arg Ser Lys Ser Ile Asn Gly Ala Thr His Tyr Ala Glu
     50                  55                  60

Ser Val Lys Gly Arg Phe Ile Ile Ser Arg Asp Asp Asn Gly Thr Ser
 65                  70                  75                  80

Leu Thr Leu Glu Met Asn Ser Leu Lys Thr Glu Asp Thr Ala Glu Tyr
                 85                  90                  95

Tyr Cys Ala Gln Asn Tyr Tyr Gly Ser Thr Tyr Asp Tyr Trp Gly Gln
             100                 105                 110

Gly Thr Leu Val Thr Val Ser
         115

<210> SEQ ID NO 153
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 153

Glu Val Gln Leu Val Glu Ser Gly Gly Gly Leu Val Gln Pro Gly Gly
  1               5                   10                  15

Ser Leu Arg Leu Ser Cys Arg Ala Ser Gln Phe Thr Phe Ser Asn His
             20                  25                  30

Tyr Met Asn Trp Val Arg Gln Ala Pro Gly Lys Gly Leu Glu Trp Ile
         35                  40                  45

Gly Glu Ile Arg Ser Lys Ser Ser Asn Gly Ala Thr Ser Tyr Ala Glu
     50                  55                  60
```

```
Ser Val Lys Gly Arg Phe Ile Ile Ser Arg Asp Gly Asn Gly Asn Asp
 65                  70                  75                  80

Leu Thr Leu Glu Met Asn Ser Leu Lys Thr Glu Asp Thr Ala Glu Tyr
                 85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 154
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 154

Glu Val Gln Leu Thr Glu Ser Gly Gly Gly Leu Val Gln Pro Gly Gly
  1               5                  10                  15

Ser Leu Arg Leu Ser Cys Arg Ala Ser Gln Ser Thr Phe Ser Asn His
                 20                  25                  30

Tyr Met Asn Trp Val Arg Gln Ala Pro Gly Lys Gly Leu Glu Trp Ile
             35                  40                  45

Gly Glu Ile Arg Ser Lys Ser Ser Asn Gly Ala Thr Ser Tyr Ala Glu
 50                  55                  60

Ser Val Lys Gly Arg Phe Ile Ile Ser Arg Asp Asp Asn Gly Asn Ser
 65                  70                  75                  80

Leu Thr Leu Glu Met Asn Ser Leu Lys Thr Glu Asp Thr Ala Glu Tyr
                 85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 155
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 155

Glu Val Gln Leu Thr Glu Ser Gly Gly Gly Leu Val Gln Pro Gly Gly
  1               5                  10                  15

Ser Leu Arg Leu Ser Cys Ala Ala Ser Gln Ser Thr Phe Ser Asn His
                 20                  25                  30

Trp Met Asn Trp Val Arg Gln Ala Pro Gly Lys Gly Leu Glu Trp Ile
             35                  40                  45

Gly Glu Ile Arg Ser Lys Ser Ser Tyr Ser Ala Thr Ser Tyr Ala Glu
 50                  55                  60

Ser Val Lys Gly Arg Phe Ile Ile Ser Arg Asp Asp Asn Lys Asn Ser
 65                  70                  75                  80

Leu Tyr Leu Glu Met Asn Ser Leu Lys Thr Glu Asp Thr Ala Glu Tyr
                 85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
```

-continued

```
        115

<210> SEQ ID NO 156
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 156

Glu Val Gln Leu Thr Glu Ser Gly Gly Gly Leu Val Gln Pro Gly Gly
 1               5                  10                  15

Ser Leu Arg Leu Ser Cys Ala Ala Ser Gln Ser Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Asn Ser Ala Thr Ser Tyr Ala Glu
    50                  55                  60

Ser Val Lys Gly Arg Phe Ile Ile Ser Arg Asp Asp Asn Lys Asn Asp
65                  70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 157
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 157

Glu Val Gln Leu Thr Glu Ser Gly Gly Gly Leu Val Gln Pro Gly Gly
 1               5                  10                  15

Ser Leu Arg Leu Ser Cys Arg Ala Ser Gly Ser Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Tyr Ser Ala Thr Ser Tyr Ala Glu
    50                  55                  60

Ser Val Lys Gly Arg Phe Ile Ile Ser Arg Asp Asp Asn Gly Thr Ser
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 158
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 158
```

Glu Val Gln Leu Val Glu Ser Gly Gly Gly Leu Val Gln Pro Gly Gly
1               5                   10                  15

Ser Leu Arg Leu Ser Cys Arg Ala Ser Gln Phe Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Tyr Gly Ala Thr His Tyr Ala Glu
    50                  55                  60

Ser Val Lys Gly Arg Phe Ile Ile Ser Arg Asp Asp Asn Lys Asn Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
                100                 105                 110

Gly Thr Leu Val Thr Val Ser
        115

<210> SEQ ID NO 159
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 159

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Tyr Ser Ala Thr Ser Tyr Ala Glu
    50                  55                  60

Ser Val Lys Gly Arg Phe Ile Ile Ser Arg Asp Gly Asn Gly Thr Ser
65                  70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
                100                 105                 110

Gly Thr Leu Val Thr Val Ser
        115

<210> SEQ ID NO 160
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 160

Glu Val Gln Leu Val Glu Ser Gly Gly Gly Leu Val Gln Pro Gly Gly
1               5                   10                  15

Ser Leu Arg Leu Ser Cys Arg Ala Ser Gln Phe Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Tyr Ser Ala Thr Ser Tyr Ala Glu

```
                 50                  55                  60
Ser Val Lys Gly Arg Phe Ile Ile Ser Arg Asp Gly Asn Lys Asn Asp
 65                  70                  75                  80

Leu Tyr Leu Glu Met Asn Ser Leu Lys Thr Glu Asp Thr Ala Glu Tyr
                 85                  90                  95

Tyr Cys Ala Gln Asn Tyr Tyr Gly Ser Thr Tyr Asp Tyr Trp Gly Gln
                100                 105                 110

Gly Thr Leu Val Thr Val Ser
            115

<210> SEQ ID NO 161
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 161

Glu Val Gln Leu Thr Glu Ser Gly Gly Gly Leu Val Gln Pro Gly Gly
  1               5                  10                  15

Ser Leu Arg Leu Ser Cys Arg Ala Ser Gly Phe Ile Phe Ser Asn His
                 20                  25                  30

Trp Met Asn Trp Val Arg Gln Ala Pro Gly Lys Gly Leu Glu Trp Ile
             35                  40                  45

Gly Glu Ile Arg Ser Lys Ser Ile Tyr Ser Ala Thr His Tyr Ala Glu
         50                  55                  60

Ser Val Lys Gly Arg Phe Ile Ile Ser Arg Asp Asp Asn Gly Asn Asp
 65                  70                  75                  80

Leu Tyr Leu Glu Met Asn Ser Leu Lys Thr Glu Asp Thr Ala Glu Tyr
                 85                  90                  95

Tyr Cys Ala Gln Asn Tyr Tyr Gly Ser Thr Pro Asp Tyr Trp Gly Gln
                100                 105                 110

Gly Thr Leu Val Thr Val Ser
            115

<210> SEQ ID NO 162
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 162

Glu Val Gln Leu Val Glu Ser Gly Gly Gly Leu Val Gln Pro Gly Gly
  1               5                  10                  15

Ser Leu Arg Leu Ser Cys Ala Ala Ser Gln Phe Ile Phe Ser Asn His
                 20                  25                  30

Tyr Met Asn Trp Val Arg Gln Ala Pro Gly Lys Gly Leu Glu Trp Ile
             35                  40                  45

Gly Glu Ile Arg Ser Lys Ser Ser Tyr Ser Ala Thr His Tyr Ala Glu
         50                  55                  60

Ser Val Lys Gly Arg Phe Ile Ile Ser Arg Asp Gly Asn Lys Asn Asp
 65                  70                  75                  80

Leu Thr Leu Glu Met Asn Ser Leu Lys Thr Glu Asp Thr Ala Glu Tyr
                 85                  90                  95

Tyr Cys Ala Arg Asn Tyr Tyr Gly Ser Thr Tyr Asp Tyr Trp Gly Gln
                100                 105                 110
```

```
Gly Thr Leu Val Thr Val Ser
        115

<210> SEQ ID NO 163
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 163

Glu Val Gln Leu Val Glu Ser Gly Gly Leu Val Gln Pro Gly Gly
  1               5                  10                  15

Ser Leu Arg Leu Ser Cys Ala Ala Ser Gln Phe Ile Phe Ser Asn His
           20                  25                  30

Trp Met Asn Trp Val Arg Gln Ala Pro Gly Lys Gly Leu Glu Trp Ile
           35                  40                  45

Gly Glu Ile Arg Ser Lys Ser Ile Tyr Ser Ala Thr His Tyr Ala Glu
       50                  55                  60

Ser Val Lys Gly Arg Phe Ile Ile Ser Arg Asp Asp Asn Lys Thr Asp
 65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
           100                 105                 110

Gly Thr Leu Val Thr Val Ser
        115

<210> SEQ ID NO 164
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 164

Glu Val Gln Leu Thr Glu Ser Gly Gly Gly Leu Val Gln Pro Gly Gly
  1               5                  10                  15

Ser Leu Arg Leu Ser Cys Ala Ala Ser Gly Ser Ile Phe Ser Asn His
           20                  25                  30

Tyr Met Asn Trp Val Arg Gln Ala Pro Gly Lys Gly Leu Glu Trp Ile
           35                  40                  45

Gly Glu Ile Arg Ser Lys Ser Ile Tyr Ser Ala Thr His Tyr Ala Glu
       50                  55                  60

Ser Val Lys Gly Arg Phe Ile Ile Ser Arg Asp Gly Asn Gly Thr Asp
 65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Tyr Asp Tyr Trp Gly Gln
           100                 105                 110

Gly Thr Leu Val Thr Val Ser
        115

<210> SEQ ID NO 165
<211> LENGTH: 119
<212> TYPE: PRT
<213> ORGANISM: Artificial Sequence
<220> FEATURE:
<223> OTHER INFORMATION: Infliximab VH variant
```

```
<400> SEQUENCE: 165

Glu Val Gln Leu Val Glu Ser Gly Gly Gly Leu Val Gln Pro Gly Gly
1               5                   10                  15

Ser Leu Arg Leu Ser Cys Ala Ala Ser Gln Phe Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Tyr Gly Ala Thr His Tyr Ala Glu
    50                  55                  60

Ser Val Lys Gly Arg Phe Ile Ile Ser Arg Asp Gly Asn Lys Thr Asp
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 166
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 166

Glu Val Gln Leu Val Glu Ser Gly Gly Gly Leu Val Gln Pro Gly Gly
1               5                   10                  15

Ser Leu Arg Leu Ser Cys Ala Ala Ser Gln Phe Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Asn Ser Ala Thr Ser Tyr Ala Glu
    50                  55                  60

Ser Val Lys Gly Arg Phe Ile Ile Ser Arg Asp Gly Asn Lys Thr Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
        115

<210> SEQ ID NO 167
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 167

Glu Val Gln Leu Val Glu Ser Gly Gly Gly Leu Val Gln Pro Gly Gly
1               5                   10                  15

Ser Leu Arg Leu Ser Cys Ala Ala Ser Gln Phe Thr Phe Ser Asn His
            20                  25                  30

Trp Met Asn Trp Val Arg Gln Ala Pro Gly Lys Gly Leu Glu Trp Ile
        35                  40                  45
```

```
Gly Glu Ile Arg Ser Lys Ser Ser Tyr Gly Ala Thr His Tyr Ala Glu
    50                  55                  60

Ser Val Lys Gly Arg Phe Ile Ile Ser Arg Asp Asp Asn Lys Thr Asp
 65                  70                  75                  80

Leu Thr Leu Glu Met Asn Ser Leu Lys Thr Glu Asp Thr Ala Glu Tyr
                 85                  90                  95

Tyr Cys Ala Arg Asn Tyr Tyr Gly Ser Thr Tyr Asp Tyr Trp Gly Gln
                100                 105                 110

Gly Thr Leu Val Thr Val Ser
        115

<210> SEQ ID NO 168
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 168

Glu Val Gln Leu Thr Glu Ser Gly Gly Gly Leu Val Gln Pro Gly Gly
  1               5                  10                  15

Ser Leu Arg Leu Ser Cys Ala Ala Ser Gln Ser Thr Phe Ser Asn His
                 20                  25                  30

Trp Met Asn Trp Val Arg Gln Ala Pro Gly Lys Gly Leu Glu Trp Ile
             35                  40                  45

Gly Glu Ile Arg Ser Lys Ser Ile Asn Gly Ala Thr Ser Tyr Ala Glu
    50                  55                  60

Ser Val Lys Gly Arg Phe Ile Ile Ser Arg Asp Gly Asn Lys Thr Ser
 65                  70                  75                  80

Leu Tyr Leu Glu Met Asn Ser Leu Lys Thr Glu Asp Thr Ala Glu Tyr
                 85                  90                  95

Tyr Cys Ala Arg Asn Tyr Tyr Gly Ser Thr Pro Asp Tyr Trp Gly Gln
                100                 105                 110

Gly Thr Leu Val Thr Val Ser
        115

<210> SEQ ID NO 169
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 169

Glu Val Gln Leu Thr Glu Ser Gly Gly Gly Leu Val Gln Pro Gly Gly
  1               5                  10                  15

Ser Leu Arg Leu Ser Cys Ala Ala Ser Gly Phe Ile Phe Ser Asn His
                 20                  25                  30

Tyr Met Asn Trp Val Arg Gln Ala Pro Gly Lys Gly Leu Glu Trp Ile
             35                  40                  45

Gly Glu Ile Arg Ser Lys Ser Ile Asn Gly Ala Thr Ser Tyr Ala Glu
    50                  55                  60

Ser Val Lys Gly Arg Phe Ile Ile Ser Arg Asp Asp Asn Gly Asn Asp
 65                  70                  75                  80

Leu Thr Leu Glu Met Asn Ser Leu Lys Thr Glu Asp Thr Ala Glu Tyr
                 85                  90                  95

Tyr Cys Ala Gln Asn Tyr Tyr Gly Ser Thr Pro Asp Tyr Trp Gly Gln
                100                 105                 110
```

Gly Thr Leu Val Thr Val Ser
        115

<210> SEQ ID NO 170
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 170

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Asn Ser Ala Thr His Tyr Ala Glu
    50                  55                  60

Ser Val Lys Gly Arg Phe Ile Ile Ser Arg Asp Asp Asn Gly Thr Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 171
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 171

Glu Val Gln Leu Val Glu Ser Gly Gly Gly Leu Val Gln Pro Gly Gly
 1               5                  10                  15

Ser Leu Arg Leu Ser Cys Ala Ala Ser Gln Ser Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Tyr Ser Ala Thr Ser Tyr Ala Glu
    50                  55                  60

Ser Val Lys Gly Arg Phe Ile Ile Ser Arg Asp Asp Asn Gly Asn Ser
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
        115

<210> SEQ ID NO 172
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 172

```
Glu Val Gln Leu Thr Glu Ser Gly Gly Gly Leu Val Gln Pro Gly Gly
1               5                   10                  15
Ser Leu Arg Leu Ser Cys Ala Ala Ser Gly Phe Thr Phe Ser Asn His
            20                  25                  30
Trp Met Asn Trp Val Arg Gln Ala Pro Gly Lys Gly Leu Glu Trp Ile
        35                  40                  45
Gly Glu Ile Arg Ser Lys Ser Ile Tyr Gly Ala Thr His Tyr Ala Glu
    50                  55                  60
Ser Val Lys Gly Arg Phe Ile Ile Ser Arg Asp Gly Asn Lys Asn Asp
65                  70                  75                  80
Leu Thr Leu Glu Met Asn Ser Leu Lys Thr Glu Asp Thr Ala Glu Tyr
                85                  90                  95
Tyr Cys Ala Gln Asn Tyr Tyr Gly Ser Thr Pro Asp Tyr Trp Gly Gln
            100                 105                 110
Gly Thr Leu Val Thr Val Ser
        115
```

<210> SEQ ID NO 173
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 173

```
Glu Val Gln Leu Thr Glu Ser Gly Gly Gly Leu Val Gln Pro Gly Gly
1               5                   10                  15
Ser Leu Arg Leu Ser Cys Arg Ala Ser Gln Ser Thr Phe Ser Asn His
            20                  25                  30
Tyr Met Asn Trp Val Arg Gln Ala Pro Gly Lys Gly Leu Glu Trp Ile
        35                  40                  45
Gly Glu Ile Arg Ser Lys Ser Asn Ser Ala Thr Ser Tyr Ala Glu
    50                  55                  60
Ser Val Lys Gly Arg Phe Ile Ile Ser Arg Asp Gly Asn Lys Thr Asp
65                  70                  75                  80
Leu Thr Leu Glu Met Asn Ser Leu Lys Thr Glu Asp Thr Ala Glu Tyr
                85                  90                  95
Tyr Cys Ala Arg Asn Tyr Tyr Gly Ser Thr Pro Asp Tyr Trp Gly Gln
            100                 105                 110
Gly Thr Leu Val Thr Val Ser
        115
```

<210> SEQ ID NO 174
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 174

```
Glu Val Gln Leu Val Glu Ser Gly Gly Gly Leu Val Gln Pro Gly Gly
1               5                   10                  15
Ser Leu Arg Leu Ser Cys Arg Ala Ser Gly Ser Thr Phe Ser Asn His
            20                  25                  30
Tyr Met Asn Trp Val Arg Gln Ala Pro Gly Lys Gly Leu Glu Trp Ile
        35                  40                  45
```

Gly Glu Ile Arg Ser Lys Ser Ser Tyr Ser Ala Thr Ser Tyr Ala Glu
          50                  55                  60

Ser Val Lys Gly Arg Phe Ile Ile Ser Arg Asp Asp Asn Lys Thr Asp
65                  70                  75                  80

Leu Thr Leu Glu Met Asn Ser Leu Lys Thr Glu Asp Thr Ala Glu Tyr
                    85                  90                  95

Tyr Cys Ala Gln Asn Tyr Tyr Gly Ser Thr Pro Asp Tyr Trp Gly Gln
                100                 105                 110

Gly Thr Leu Val Thr Val Ser
            115

<210> SEQ ID NO 175
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 175

Glu Val Gln Leu Val Glu Ser Gly Gly Gly Leu Val Gln Pro Gly Gly
1               5                   10                  15

Ser Leu Arg Leu Ser Cys Arg Ala Ser Gly Phe Ile Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Asn Gly Ala Thr His Tyr Ala Glu
        50                  55                  60

Ser Val Lys Gly Arg Phe Ile Ile Ser Arg Asp Asp Asn Lys Thr Ser
65                  70                  75                  80

Leu Thr Leu Glu Met Asn Ser Leu Lys Thr Glu Asp Thr Ala Glu Tyr
                    85                  90                  95

Tyr Cys Ala Gln Asn Tyr Tyr Gly Ser Thr Tyr Asp Tyr Trp Gly Gln
                100                 105                 110

Gly Thr Leu Val Thr Val Ser
            115

<210> SEQ ID NO 176
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 176

Glu Val Gln Leu Thr Glu Ser Gly Gly Gly Leu Val Gln Pro Gly Gly
1               5                   10                  15

Ser Leu Arg Leu Ser Cys Arg Ala Ser Gln Ser Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Tyr Ser Ala Thr His Tyr Ala Glu
        50                  55                  60

Ser Val Lys Gly Arg Phe Ile Ile Ser Arg Asp Gly Asn Gly Asn Asp
65                  70                  75                  80

Leu Tyr Leu Glu Met Asn Ser Leu Lys Thr Glu Asp Thr Ala Glu Tyr
                    85                  90                  95

Tyr Cys Ala Gln Asn Tyr Tyr Gly Ser Thr Pro Asp Tyr Trp Gly Gln

```
                    100                 105                 110

Gly Thr Leu Val Thr Val Ser
        115

<210> SEQ ID NO 177
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 177

Glu Val Gln Leu Thr Glu Ser Gly Gly Gly Leu Val Gln Pro Gly Gly
1               5                   10                  15

Ser Leu Arg Leu Ser Cys Ala Ala Ser Gln Ser Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Asn Gly Ala Thr Ser Tyr Ala Glu
    50                  55                  60

Ser Val Lys Gly Arg Phe Ile Ile Ser Arg Asp Asp Asn Lys Asn Asp
65                  70                  75                  80

Leu Thr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 178
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 178

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Tyr Ser Ala Thr His Tyr Ala Glu
    50                  55                  60

Ser Val Lys Gly Arg Phe Ile Ile Ser Arg Asp Gly Asn Gly Asn Ser
65                  70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 179
<211> LENGTH: 119
<212> TYPE: PRT
<213> ORGANISM: Artificial Sequence
<220> FEATURE:
```

<223> OTHER INFORMATION: Infliximab VH variant

<400> SEQUENCE: 179

```
Glu Val Gln Leu Thr Glu Ser Gly Gly Gly Leu Val Gln Pro Gly Gly
 1               5                  10                  15
Ser Leu Arg Leu Ser Cys Ala Ala Ser Gln Phe Thr Phe Ser Asn His
            20                  25                  30
Trp Met Asn Trp Val Arg Gln Ala Pro Gly Lys Gly Leu Glu Trp Ile
        35                  40                  45
Gly Glu Ile Arg Ser Lys Ser Ser Asn Gly Ala Thr His Tyr Ala Glu
    50                  55                  60
Ser Val Lys Gly Arg Phe Ile Ile Ser Arg Asp Asp Asn Gly Thr Ser
65                  70                  75                  80
Leu Thr Leu Glu Met Asn Ser Leu Lys Thr Glu Asp Thr Ala Glu Tyr
                85                  90                  95
Tyr Cys Ala Arg Asn Tyr Tyr Gly Ser Thr Pro Asp Tyr Trp Gly Gln
            100                 105                 110
Gly Thr Leu Val Thr Val Ser
        115
```

<210> SEQ ID NO 180
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 180

```
Glu Val Gln Leu Val Glu Ser Gly Gly Gly Leu Val Gln Pro Gly Gly
 1               5                  10                  15
Ser Leu Arg Leu Ser Cys Arg Ala Ser Gly Phe Ile Phe Ser Asn His
            20                  25                  30
Tyr Met Asn Trp Val Arg Gln Ala Pro Gly Lys Gly Leu Glu Trp Ile
        35                  40                  45
Gly Glu Ile Arg Ser Lys Ser Ser Asn Ser Ala Thr His Tyr Ala Glu
    50                  55                  60
Ser Val Lys Gly Arg Phe Ile Ile Ser Arg Asp Asp Asn Lys Thr Ser
65                  70                  75                  80
Leu Thr Leu Glu Met Asn Ser Leu Lys Thr Glu Asp Thr Ala Glu Tyr
                85                  90                  95
Tyr Cys Ala Gln Asn Tyr Tyr Gly Ser Thr Pro Asp Tyr Trp Gly Gln
            100                 105                 110
Gly Thr Leu Val Thr Val Ser
        115
```

<210> SEQ ID NO 181
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 181

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Asn His
            20                  25                  30
Trp Met Asn Trp Val Arg Gln Ala Pro Gly Lys Gly Leu Glu Trp Ile
```

```
                        35                  40                  45
Gly Glu Ile Arg Ser Lys Ser Ser Tyr Ser Ala Thr His Tyr Ala Glu
        50                  55                  60
Ser Val Lys Gly Arg Phe Ile Ile Ser Arg Asp Asp Asn Lys Asn Ser
 65                  70                  75                  80
Leu Thr Leu Glu Met Asn Ser Leu Lys Thr Glu Asp Thr Ala Glu Tyr
                85                  90                  95
Tyr Cys Ala Gln Asn Tyr Tyr Gly Ser Thr Pro Asp Tyr Trp Gly Gln
                    100                 105                 110
Gly Thr Leu Val Thr Val Ser
            115

<210> SEQ ID NO 182
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 182

Glu Val Gln Leu Thr Glu Ser Gly Gly Gly Leu Val Gln Pro Gly Gly
  1               5                  10                  15
Ser Leu Arg Leu Ser Cys Ala Ala Ser Gly Phe Thr Phe Ser Asn His
                20                  25                  30
Tyr Met Asn Trp Val Arg Gln Ala Pro Gly Lys Gly Leu Glu Trp Ile
            35                  40                  45
Gly Glu Ile Arg Ser Lys Ser Ile Tyr Ser Ala Thr His Tyr Ala Glu
        50                  55                  60
Ser Val Lys Gly Arg Phe Ile Ile Ser Arg Asp Gly Asn Gly Thr Asp
 65                  70                  75                  80
Leu Tyr Leu Glu Met Asn Ser Leu Lys Thr Glu Asp Thr Ala Glu Tyr
                85                  90                  95
Tyr Cys Ala Gln Asn Tyr Tyr Gly Ser Thr Pro Asp Tyr Trp Gly Gln
                    100                 105                 110
Gly Thr Leu Val Thr Val Ser
            115

<210> SEQ ID NO 183
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 183

Glu Val Gln Leu Thr Glu Ser Gly Gly Gly Leu Val Gln Pro Gly Gly
  1               5                  10                  15
Ser Leu Arg Leu Ser Cys Ala Ala Ser Gln Ser Thr Phe Ser Asn His
                20                  25                  30
Tyr Met Asn Trp Val Arg Gln Ala Pro Gly Lys Gly Leu Glu Trp Ile
            35                  40                  45
Gly Glu Ile Arg Ser Lys Ser Tyr Gly Ala Thr Ser Tyr Ala Glu
        50                  55                  60
Ser Val Lys Gly Arg Phe Ile Ile Ser Arg Asp Gly Asn Gly Thr Ser
 65                  70                  75                  80
Leu Tyr Leu Glu Met Asn Ser Leu Lys Thr Glu Asp Thr Ala Glu Tyr
                85                  90                  95
```

```
Tyr Cys Ala Arg Asn Tyr Tyr Gly Ser Thr Tyr Asp Tyr Trp Gly Gln
            100                 105                 110

Gly Thr Leu Val Thr Val Ser
            115

<210> SEQ ID NO 184
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 184

Glu Val Gln Leu Val Glu Ser Gly Gly Gly Leu Val Gln Pro Gly Gly
 1               5                  10                  15

Ser Leu Arg Leu Ser Cys Ala Ala Ser Gln Phe Ile Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Asn Ser Ala Thr His Tyr Ala Glu
    50                  55                  60

Ser Val Lys Gly Arg Phe Ile Ile Ser Arg Asp Gly Asn Gly Thr Asp
65                  70                  75                  80

Leu Tyr Leu Glu Met Asn Ser Leu Lys Thr Glu Asp Thr Ala Glu Tyr
                85                  90                  95

Tyr Cys Ala Arg Asn Tyr Tyr Gly Ser Thr Tyr Asp Tyr Trp Gly Gln
            100                 105                 110

Gly Thr Leu Val Thr Val Ser
            115

<210> SEQ ID NO 185
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 185

Glu Val Gln Leu Thr Glu Ser Gly Gly Gly Leu Val Gln Pro Gly Gly
 1               5                  10                  15

Ser Leu Arg Leu Ser Cys Arg Ala Ser Gln Ser Thr Phe Ser Asn His
            20                  25                  30

Trp Met Asn Trp Val Arg Gln Ala Pro Gly Lys Gly Leu Glu Trp Ile
        35                  40                  45

Gly Glu Ile Arg Ser Lys Ser Ile Tyr Ser Ala Thr Ser Tyr Ala Glu
    50                  55                  60

Ser Val Lys Gly Arg Phe Ile Ile Ser Arg Asp Gly Asn Gly Asn Asp
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Pro Asp Tyr Trp Gly Gln
            100                 105                 110

Gly Thr Leu Val Thr Val Ser
            115

<210> SEQ ID NO 186
<211> LENGTH: 119
<212> TYPE: PRT
<213> ORGANISM: Artificial Sequence
```

```
<220> FEATURE:
<223> OTHER INFORMATION: Infliximab VH variant

<400> SEQUENCE: 186

Glu Val Gln Leu Thr Glu Ser Gly Gly Gly Leu Val Gln Pro Gly Gly
1               5                   10                  15

Ser Leu Arg Leu Ser Cys Ala Ala Ser Gly Ser Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ile Tyr Ser Ala Thr Ser Tyr Ala Glu
    50                  55                  60

Ser Val Lys Gly Arg Phe Ile Ile Ser Arg Asp Asp Asn Gly Asn Ser
65                  70                  75                  80

Leu Thr Leu Glu Met Asn Ser Leu Lys Thr Glu Asp Thr Ala Glu Tyr
                85                  90                  95

Tyr Cys Ala Arg Asn Tyr Tyr Gly Ser Thr Pro Asp Tyr Trp Gly Gln
            100                 105                 110

Gly Thr Leu Val Thr Val Ser
        115

<210> SEQ ID NO 187
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 187

Glu Val Gln Leu Thr Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Tyr Met Asn Trp Val Arg Gln Ala Pro Gly Lys Gly Leu Glu Trp Ile
        35                  40                  45

Gly Glu Ile Arg Ser Lys Ser Ser Tyr Gly Ala Thr Ser Tyr Ala Glu
    50                  55                  60

Ser Val Lys Gly Arg Phe Ile Ile Ser Arg Asp Gly Asn Gly Thr Asp
65                  70                  75                  80

Leu Tyr Leu Glu Met Asn Ser Leu Lys Thr Glu Asp Thr Ala Glu Tyr
                85                  90                  95

Tyr Cys Ala Gln Asn Tyr Tyr Gly Ser Thr Tyr Asp Tyr Trp Gly Gln
            100                 105                 110

Gly Thr Leu Val Thr Val Ser
        115

<210> SEQ ID NO 188
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 188

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Asn His
            20                  25                  30
```

```
Tyr Met Asn Trp Val Arg Gln Ala Pro Gly Lys Gly Leu Glu Trp Ile
        35                  40                  45

Gly Glu Ile Arg Ser Lys Ser Ile Tyr Gly Ala Thr Ser Tyr Ala Glu
 50                  55                  60

Ser Val Lys Gly Arg Phe Ile Ile Ser Arg Asp Asp Asn Lys Asn Asp
 65                  70                  75                  80

Leu Tyr Leu Glu Met Asn Ser Leu Lys Thr Glu Asp Thr Ala Glu Tyr
                 85                  90                  95

Tyr Cys Ala Gln Asn Tyr Tyr Gly Ser Thr Tyr Asp Tyr Trp Gly Gln
                100                 105                 110

Gly Thr Leu Val Thr Val Ser
        115

<210> SEQ ID NO 189
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 189

Glu Val Gln Leu Thr Glu Ser Gly Gly Gly Leu Val Gln Pro Gly Gly
 1               5                  10                  15

Ser Leu Arg Leu Ser Cys Ala Ala Ser Gln Phe Thr Phe Ser Asn His
             20                  25                  30

Trp Met Asn Trp Val Arg Gln Ala Pro Gly Lys Gly Leu Glu Trp Ile
        35                  40                  45

Gly Glu Ile Arg Ser Lys Ser Ile Tyr Ser Ala Thr His Tyr Ala Glu
 50                  55                  60

Ser Val Lys Gly Arg Phe Ile Ile Ser Arg Asp Asp Asn Gly Thr Ser
 65                  70                  75                  80

Leu Thr Leu Glu Met Asn Ser Leu Lys Thr Glu Asp Thr Ala Glu Tyr
                 85                  90                  95

Tyr Cys Ala Arg Asn Tyr Tyr Gly Ser Thr Pro Asp Tyr Trp Gly Gln
                100                 105                 110

Gly Thr Leu Val Thr Val Ser
        115

<210> SEQ ID NO 190
<211> LENGTH: 119
<212> TYPE: PRT
<213> ORGANISM: Artificial Sequence
<220> FEATURE:
<223> OTHER INFORMATION: Infliximab VH variant

<400> SEQUENCE: 190

Glu Val Gln Leu Val Glu Ser Gly Gly Gly Leu Val Gln Pro Gly Gly
 1               5                  10                  15

Ser Leu Arg Leu Ser Cys Arg Ala Ser Gly Phe Ile Phe Ser Asn His
             20                  25                  30

Trp Met Asn Trp Val Arg Gln Ala Pro Gly Lys Gly Leu Glu Trp Ile
        35                  40                  45

Gly Glu Ile Arg Ser Lys Ser Ile Asn Ser Ala Thr Ser Tyr Ala Glu
 50                  55                  60

Ser Val Lys Gly Arg Phe Ile Ile Ser Arg Asp Gly Asn Lys Thr Asp
 65                  70                  75                  80

Leu Thr Leu Glu Met Asn Ser Leu Lys Thr Glu Asp Thr Ala Glu Tyr
                 85                  90                  95
```

Tyr Cys Ala Arg Asn Tyr Tyr Gly Ser Thr Tyr Asp Tyr Trp Gly Gln
            100                 105                 110
Gly Thr Leu Val Thr Val Ser
        115

<210> SEQ ID NO 191
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 191
gaggtgcagc tggtggagag cggaggagga ctggtgcagc ctggaggaag cctgagactg      60
agctgcgccg ccagcggctt catcttcagc aaccactgga tgaactgggt gagacaggct     120
cctggcaagg gcctggagtg gatcggcgag atccggagca agagcatcaa cagcgccacc     180
cactacgccg agagcgtgaa gggccggttc atcatcagcc gggacgacaa caagaacagc     240
ctgtacctgg agatgaacag cctgaagacc gaggacaccg ccgagtacta ctgcgcccgg     300
aactactacg gcagcaccta cgactactgg ggccagggaa ccctggtgac cgtgagc        357

<210> SEQ ID NO 192
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 192
gaagttcagc tgaccgaatc tggtggtggt ctggttcagc cgggtggttc tctgcgtctg      60
tcttgccgtg cgtctggttt catcttctct aaccactgga tgaactgggt tcgtcaggcg     120
ccgggtaaag gtctggaatg gatcggtgaa atccgttcta atctcttcta ctctgcgacc     180
tcttacgcgg aatctgttaa aggtcgtttc atcatctctc gtgacgacaa caaaaacctct     240 ctgtacctgg aaatgaactc tctgaaaacc gaagacaccg cggaatacta ctgcgcgcag     300
aactactacg gttctaccta cgactactgg ggtcaggggta ccctggttac cgtttct       357

<210> SEQ ID NO 193
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 193
gaagttcagc tgaccgaatc tggtggtggt ctggttcagc cgggtggttc tctgcgtctg      60
tcttgcgcgg cgtctcagtt caccttctct aaccactgga tgaactgggt tcgtcaggcg     120
ccgggtaaag gtctggaatg gatcggtgaa atccgttcta atctatcaa ctctgcgacc     180 cactacgcgg aatctgttaa aggtcgtttc atcatctctc gtgacgacaa caaaaacctct     240 ctgaccctgg aaatgaactc tctgaaaacc gaagacaccg cggaatacta ctgcgcgcgt     300
aactactacg gttctaccta cgactactgg ggtcagggta ccctggttac cgtttct        357

<210> SEQ ID NO 194
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 194

| gaagttcagt tggttgaatc tggtggtggt ctggttcagc cgggtggttc tctgcgtctg | 60 |
| tcttgcgcgg cgtctcagtt caccttctct aaccactaca tgaactgggt tcgtcaggcg | 120 |
| ccgggtaaag gtctggaatg gatcggtgaa atccgttcta atcttctta ctctgcgacc | 180 |
| cactacgcgg aatctgttaa aggtcgtttc atcatctctc gtgacggtaa caaaaccgac | 240 |
| ctgtacctgg aaatgaactc tctgaaaacc gaagacaccg cggaatacta ctgcgcgcgt | 300 |
| aactactacg gttctacccc ggactactgg ggtcaggta ccctggttac cgtttct | 357 |

<210> SEQ ID NO 195
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 195

| gaagttcagc tgaccgaatc tggtggtggt ctggttcagc cgggtggttc tctgcgtctg | 60 |
| tcttgcgcgg cgtctcagtt caccttctct aaccactgga tgaactgggt tcgtcaggcg | 120 |
| ccgggtaaag gtctggaatg gatcggtgaa atccgttcta atcttctaa ctctgcgacc | 180 |
| cactacgcgg aatctgttaa aggtcgtttc atcatctctc gtgacgacaa caaaaccgac | 240 |
| ctgtacctgg aaatgaactc tctgaaaacc gaagacaccg cggaatacta ctgcgcgcag | 300 |
| aactactacg gttctaccta cgactactgg ggtcagggta ccctggttac cgtttct | 357 |

<210> SEQ ID NO 196
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 196

| gaagttcagc tgaccgaatc tggtggtggt ctggttcagc cgggtggttc tctgcgtctg | 60 |
| tcttgccgtg cgtctggttc taccttctct aaccactaca tgaactgggt tcgtcaggcg | 120 |
| ccgggtaaag gtctggaatg gatcggtgaa atccgttcta atctatcaa cggtgcgacc | 180 |
| cactacgcgg aatctgttaa aggtcgtttc atcatctctc gtgacggtaa cggtaacgac | 240 |
| ctgtacctgg aaatgaactc tctgaaaacc gaagacaccg cggaatacta ctgcgcgcag | 300 |
| aactactacg gttctaccta cgactactgg ggtcagggta ccctggttac cgtttct | 357 |

<210> SEQ ID NO 197
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 197

| gaagttcagc tgaccgaatc tggtggtggt ctggttcagc cgggtggttc tctgcgtctg | 60 |
| tcttgccgtg cgtctcagtc tatcttctct aaccactaca tgaactgggt tcgtcaggcg | 120 |
| ccgggtaaag gtctggaatg gatcggtgaa atccgttcta atctatcaa ctctgcgacc | 180 |

```
tcttacgcgg aatctgttaa aggtcgtttc atcatctctc gtgacgacaa cggtaacgac    240
ctgaccctgg aaatgaactc tctgaaaacc gaagacaccg cggaatacta ctgcgcgcag    300
aactactacg gttctaccta cgactactgg ggtcagggta ccctggttac cgtttct       357

<210> SEQ ID NO 198
<211> LENGTH: 357
<212> TYPE: DNA
<213> ORGANISM: Artificial Sequence
<220> FEATURE:
<223> OTHER INFORMATION: Infliximab VH variant

<400>SEQUENCE: 198 gaagttcagc tgaccgaatc tggtggtggt ctggttcagc cgggtggttc tctgcgtctg    60
tcttgccgtg cgtctggttt catcttctct aaccactaca tgaactgggt tcgtcaggcg    120
ccgggtaaag gtctggaatg gatcggtgaa atccgttcta atctatcaa ctctgcgacc     180 tcttacgcgg aatctgttaa aggtcgtttc atcatctctc gtgacgacaa caaaaacgac    240
ctgaccctgg aaatgaactc tctgaaaacc gaagacaccg cggaatacta ctgcgcgcgt    300
aactactacg gttctaccta cgactactgg ggtcagggta ccctggttac cgtttct       357

<210> SEQ ID NO 199
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 199
gaagttcagc tgaccgaatc tggtggtggt ctggttcagc cgggtggttc tctgcgtctg    60
tcttgcgcgg cgtctggttt catcttctct aaccactgga tgaactgggt tcgtcaggcg    120
ccgggtaaag gtctggaatg gatcggtgaa atccgttcta atctatcaa cggtgcgacc     180 tcttacgcgg aatctgttaa aggtcgtttc atcatctctc gtgacgacaa caaaacctct    240
ctgtacctgg aaatgaactc tctgaaaacc gaagacaccg cggaatacta ctgcgcgcag    300
aactactacg gttctaccta cgactactgg ggtcagggta ccctggttac cgtttct       357

<210> SEQ ID NO 200
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 200
gaagttcagc tgaccgaatc tggtggtggt ctggttcagc cgggtggttc tctgcgtctg    60
tcttgccgtg cgtctcagtc tatcttctct aaccactgga tgaactgggt tcgtcaggcg    120
ccgggtaaag gtctggaatg gatcggtgaa atccgttcta atcttctaa ctctgcgacc     180 tcttacgcgg aatctgttaa aggtcgtttc atcatctctc gtgacggtaa caaaaacgac    240
ctgaccctgg aaatgaactc tctgaaaacc gaagacaccg cggaatacta ctgcgcgcag    300
aactactacg gttctacccc ggactactgg ggtcagggta ccctggttac cgtttct       357

<210> SEQ ID NO 201
<211> LENGTH: 357
<212> TYPE: DNA
<213> ORGANISM: Artificial Sequence
<220> FEATURE:
<223> OTHER INFORMATION: Infliximab VH variant
```

<400> SEQUENCE: 201

```
gaagttcagc tgaccgaatc tggtggtggt ctggttcagc cgggtggttc tctgcgtctg    60
tcttgcgcgg cgtctggttc tatcttctct aaccactaca tgaactgggt tcgtcaggcg   120
ccgggtaaag gtctggaatg gatcggtgaa atccgttcta atcttctaa ctctgcgacc    180
cactacgcgg aatctgttaa aggtcgtttc atcatctctc gtgacgacaa caaaaccgac   240
ctgtacctgg aaatgaactc tctgaaaacc gaagacaccg cggaatacta ctgcgcgcgt   300
aattactacg gttctaccta cgactactgg ggtcaggta ccctggttac cgtttct      357
```

<210> SEQ ID NO 202
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 202

```
gaagttcagc tgaccgaatc tggtggtggt ctggttcagc cgggtggttc tctgcgtctg    60
tcttgcgcgg cgtctcagtt caccttctct aaccactgga tgaactgggt tcgtcaggcg   120
ccgggtaaag gtctggaatg gatcggtgaa atccgttcta atctatcta cggtgcgacc    180
cactacgcgg aatctgttaa aggtcgtttc atcatctctc gtgacggtaa cggtaacgac   240
ctgtacctgg aaatgaactc tctgaaaacc gaagacaccg cggaatacta ctgcgcgcgt   300
aactactacg gttctacccc ggactactgg ggtcaggta ccctggttac cgtttct      357
```

<210> SEQ ID NO 203
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 203

```
gaagttcagc tgaccgaatc tggtggtggt ctggttcagc cgggtggttc tctgcgtctg    60
tcttgccgtg cgtctcagtc taccttctct aaccactgga tgaactgggt tcgtcaggcg   120
ccgggtaaag gtctggaatg gatcggtgaa atccgttcta atcttctta ctctgcgacc    180
cactacgcgg aatctgttaa aggtcgtttc atcatctctc gtgacgacaa caaaaacgac   240
ctgtacctgg aaatgaactc tctgaaaacc gaagacaccg cggaatacta ctgcgcgcag   300
aactactacg gttctacccc ggactactgg ggtcaggta ccctggttac cgtttct      357
```

<210> SEQ ID NO 204
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 204

```
gaagttcagc tgaccgaatc tggtggtggt ctggttcagc cgggtggttc tctgcgtctg    60
tcttgcgcgg cgtctcagtc tatcttctct aaccactaca tgaactgggt tcgtcaggcg   120
ccgggtaaag gtctggaatg gatcggtgaa atccgttcta atcttctaa ctctgcgacc    180
cactacgcgg aatctgttaa aggtcgtttc atcatctctc gtgacggtaa cggtaacgac   240
```

```
ctgaccctgg aaatgaactc tctgaaaacc gaagacaccg cggaatacta ctgcgcgcag    300
aactactacg gttctacccc ggactactgg ggtcaggta  ccctggttac cgtttct      357
```

<210> SEQ ID NO 205
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 205

```
gaagttcagc tgaccgaatc tggtggtggt ctggttcagc cgggtggttc tctgcgtctg    60
tcttgccgtg cgtctggttt caccttctct aaccactgga tgaactgggt tcgtcaggcg    120
ccgggtaaag gtctggaatg gatcggtgaa atccgttcta atcttctta  ctctgcgacc    180 cactacgcgg aatctgttaa aggtcgtttc atcatctctc gtgacgacaa caaaacctct    240
ctgtacctgg aaatgaactc tctgaaaacc gaagacaccg cggaatacta ctgcgcgcgt    300
aactactacg gttctacccc ggactactgg ggtcaggta  ccctggttac cgtttct      357
```

<210> SEQ ID NO 206
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 206

```
gaagttcagc tggttgaatc tggtggtggt ctggttcagc cgggtggttc tctgcgtctg    60
tcttgccgtg cgtctcagtt caccttctct aaccactaca tgaactgggt tcgtcaggcg    120
ccgggtaaag gtctggaatg gatcggtgaa atccgttcta atcttctaa  cggtgcgacc    180 tcttacgcgg aatctgttaa aggtcgtttc atcatctctc gtgacggtaa cggtaactct    240
ctgaccctgg aaatgaactc tctgaaaacc gaagacaccg cggaatacta ctgcgcgcgt    300
aactactacg gttctaccta cgactactgg ggtcaggta  ccctggttac cgtttct      357
```

<210> SEQ ID NO 207
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 207

```
gaagttcagc tgaccgaatc tggtggtggt ctggttcagc cgggtggttc tctgcgtctg    60
tcttgccgtg cgtctcagtt caccttctct aaccactaca tgaactgggt tcgtcaggcg    120
ccgggtaaag gtctggaatg gatcggtgaa atccgttcta atcttctaa  ctctgcgacc    180 tcttacgcgg aatctgttaa aggtcgtttc atcatctctc gtgacgacaa caaaacctct    240
ctgaccctgg aaatgaactc tctgaaaacc gaagacaccg cggaatacta ctgcgcgcag    300
aactactacg gttctacccc ggactactgg ggtcaggta  ccctggttac cgtttct      357
```

```
<210> SEQ ID NO 208
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 208
gaagttcagc tggttgaatc tggtggtggt ctggttcagc cgggtggttc tctgcgtctg      60
tcttgccgtg cgtctggttt caccttctct aaccactaca tgaactgggt tcgtcaggcg     120
ccgggtaaag gtctggaatg gatcggtgaa atccgttcta atcttctaa ctctgcgacc      180 tcttacgcgg aatctgttaa aggtcgtttc atcatctctc gtgacgacaa cggtaacgac     240
ctgaccctgg aaatgaactc tctgaaaacc gaagacaccg cggaatacta ctgcgcgcag     300
aactactacg gttctacccc ggactactgg ggtcaggta ccctggttac cgtttct        357

<210> SEQ ID NO 209
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 209
gaagttcagc tgaccgaatc tggtggtggt ctggttcagc cgggtggttc tctgcgtctg      60
tcttgcgcgg cgtctcagtt caccttctct aaccactgga tgaactgggt tcgtcaggcg     120
ccgggtaaag gtctggaatg gatcggtgaa atccgttcta atctatcta cggtgcgacc      180 cactacgcgg aatctgttaa aggtcgtttc atcatctctc gtgacgacaa cggtaacgac     240
ctgtacctgg aaatgaactc tctgaaaacc gaagacaccg cggaatacta ctgcgcgcgt     300
aactactacg gttctaccta cgactactgg ggtcagggta ccctggttac cgttcct       357

<210> SEQ ID NO 210
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 210
gaagttcagc tggttgaatc tggtggtggt ctggttcagc cgggtggttc tctgcgtctg      60
tcttgccgtg cgtctggttc taccttctct aaccactgga tgaactgggt tcgtcaggcg     120
ccgggtaaag gtctggaatg gatcggtgaa atccgttcta atctctaa ctctgcgacc       180 cactacgcgg aatctgttaa aggtcgtttc atcatctctc gtgacgacaa cggtaactct     240
ctgaccctgg aaatgaactc tctgaaaacc gaagacaccg cggaatacta ctgcgcgcag    300
aactactacg gttctaccta cgactactgg ggtcagggta ccctggttac cgttcct       357

<210> SEQ ID NO 211
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 211
gaagttcagc tgaccgaatc tggtggtggt ctggttcagc cgggtggttc tctgcgtctg      60
tcttgcgcgg cgtctggttc tatcttctct aaccactgga tgaactgggt tcgtcaggcg     120
```

```
ccgggtaaag gtctggaatg gatcggtgaa atccgttcta aatctatcta cggtgcgacc    180
cactacgcgg aatctgttaa aggtcgtttc atcatctctc gtgacgacaa cggtaccgac    240
ctgtacctgg aaatgaactc tctgaaaacc gaagacaccg cggaatacta ctgcgcgcgt    300
aactactacg gttctaccta cgactactgg ggtcagggta ccctggttac cgtttct       357
```

<210> SEQ ID NO 212
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 212

```
gaagttcagc tgaccgaatc tggtggtggt ctggttcagc cgggtggttc tctgcgtctg    60
tcttgcgcgg cgtctggttc tatcttctct aaccactgga tgaactgggt tcgtcaggcg    120
ccgggtaaag gtctggaatg gatcggtgaa atccgttcta atctatcaa cggtgcgacc     180 tcttacgcgg aatctgttaa aggtcgtttc atcatctctc gtgacgacaa cggtaactct    240
ctgaccctgg aaatgaactc tctgaaaacc gaagacaccg cggaatacta ctgcgcgcag    300
aactactacg gttctacccc ggactactgg ggtcagggta ccctggttac cgtttct       357
```

<210> SEQ ID NO 213
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 213

```
gaagttcagc tggttgaatc tggtggtggt ctggttcagc cgggtggttc tctgcgtctg    60
tcttgccgtg cgtctcagtt catcttctct aaccactaca tgaactgggt tcgtcaggcg    120
ccgggtaaag gtctggaatg gatcggtgaa atccgttcta atctatcaa ctctgcgacc     180 cactacgcgg aatctgttaa aggtcgttt atcatctctc gtgacggtaa caaaacctct    240
ctgtacctgg aaatgaactc tctgaaaacc gaagacaccg cggaatacta ctgcgcgcag    300
aactactacg gttctacccc ggactactgg ggtcagggta ccctggttac cgtttct       357
```

<210> SEQ ID NO 214
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 214

```
gaagttcagc tggttgaatc tggtggtggt ctggttcagc cgggtggttc tctgcgtctg    60
tcttgccgtg cgtctcagtt caccttctct aaccactaca tgaactgggt tcgtcaggcg    120
ccgggtaaag gtctggaatg gatcggtgaa atccgttcta atctatcta ctctgcgacc     180 cactacgcgg aatctgttaa aggtcgtttc atcatctctc gtgacgacaa caaaaacgac    240
ctgaccctgg aaatgaactc tctgaaaacc gaagacaccg cggaatacta ctgcgcgcgt    300
aactactacg gttctaccta cgactactgg ggtcagggta ccctggttac cgtttct       357
```

<210> SEQ ID NO 215
<211> LENGTH: 357
<212> TYPE: DNA
<213> ORGANISM: Artificial Sequence

```
<220> FEATURE:
<223> OTHER INFORMATION: Infliximab VH variant

<400> SEQUENCE: 215
gaagttcagc tggttgaatc tggtggtggt ctggttcagc cgggtggttc tctgcgtctg      60
tcttgcgcgg cgtctcagtt catcttctct aaccactaca tgaactgggt tcgtcaggcg     120
ccgggtaaag gtctggaatg gatcggtgaa atccgttcta atcttctaa cggtgcgacc      180 cactacgcgg aatctgttaa aggtcgtttc atcatctctc gtgacgacaa caaaaacgac     240
ctgtacctgg aaatgaactc tctgaaaacc gaagacaccg cggaatacta ctgcgcgcag     300
aactactacg gttctacccc ggactactgg ggtcagggta ccctggttac cgtttct        357

<210> SEQ ID NO 216
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 216
gaagttcagt tggtcgaatc tggtggtggt ctggttcagc cgggtggttc tctgcgtctg      60
tcttgcgcgg cgtctggttc taccttctct aaccactgga tgaactgggt tcgtcaggcg     120
ccgggtaaag gtctggaatg gatcggtgaa atccgttcta atcttcttta cggtgcgacc     180
tcttacgcgg aatctgttaa aggtcgtttc atcatctctc gtgacggtaa cggtaactct     240
ctgaccctgg aaatgaactc tctgaaaacc gaagacaccg cggaatacta ctgcgcgcag     300
aactactacg gttctacccc ggactactgg ggtcagggta ccctggttac cgtttct        357

<210> SEQ ID NO 217
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 217
gaagttcagc tgaccgaatc tggtggtggt ctggttcagc cgggtggttc tctgcgtctg      60
tcttgccgtg cgtctcagtc tatcttctct aaccactaca tgaactgggt tcgtcaggcg     120
ccaggtaaag gtctggaatg gatcggtgaa atccgttcta atcttctaa ctctgcgacc      180 tcttacgcgg aatctgttaa aggtcgtttc atcatctctc gtgacgacaa caaaacctct     240
ctgtacctgg aaatgaactc tctgaaaacc gaagacaccg cggaatacta ctgcgcgcgt     300
aactactacg gttctaccta cgactactgg ggtcagggta ccctggttac cgtttct        357

<210> SEQ ID NO 218
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 218
gaagttcagc tggttgaatc tggtggtggt ctggttcagc cgggtggttc tctgcgtctg      60
tcttgccgtg cgtctcagtc taccttctct aaccactgga tgaactgggt tcgtcaggcg     120
ccgggtaaag gtctggaatg gatcggtgaa atccgttcta atctatctta ctctgcgacc     180
tcttacgcgg aatctgttaa aggtcgtttc atcatctctc gtgacggtaa caaaacctct     240
```

```
ctgaccctgg aaatgaactc tctgaaaacc gaagacaccg cggaatacta ctgcgcgcag    300
aactactacg gttctacccc ggactactgg ggtcaggggta ccctggttac cgtttct      357

<210> SEQ ID NO 219
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 219
gaagttcagc tgaccgaatc tggtggtggt ctggttcagc cgggtggttc tctgcgtctg    60
tcttgcgcgg cgtctcagtt catcttctct aaccactaca tgaactgggt cgtcaggcg    120 ccgggtaaag gtctggaatg gatcggtgaa atccgttcta atcttctta cggtgcgacc    180 cactacgcgg aatctgttaa aggtcgtttc atcatctctc gtgacggtaa caaaaccgac    240
ctgaccctgg aaatgaactc tctgaaaacc gaagacaccg cggaatacta ctgcgcgcag    300
aactactacg gttctaccta cgactactgg ggtcagggta ccctggttac cgtttct      357

<210> SEQ ID NO 220
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 220
gaagttcagc tgaccgaatc tggtggtggt ctggttcagc cgggtggttc tctgcgtctg    60
tcttgccgtg cgtctcagtt caccttctct aaccactaca tgaactgggt cgtcaggcg    120 ccgggtaaag gtctggaatg gatcggtgaa atccgttcta atcttctaa cggtgcgacc    180 tcttacgcgg aatctgttaa aggtcgtttc atcatctctc gtgacggtaa cggtaactct   240
ctgaccctgg aaatgaactc tctgaaaacc gaagacaccg cggaatacta ctgcgcgcag    300
aactactacg gttctaccta cgactactgg ggtcagggta ccctggttac cgtttct      357

<210> SEQ ID NO 221
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 221
gaagttcagc tggttgaatc tggtggtggt ctggttcagc cgggtggttc tctgcgtctg    60
tcttgccgtg cgtctggttc tatcttctct aaccactaca tgaattgggt cgtcaggcg    120 ccgggtaaag gtctggaatg gatcggtgaa atccgttcta atcttctaa cggtgcgacc    180 cactacgcgg aatctgttaa aggtcgtttc atcatctctc gtgacgacaa caaaaactct   240
ctgtacctgg aaatgaactc tctgaaaacc gaagacaccg cggaatacta ctgcgcgcgt    300
aactactacg gttctaccta cgactactgg ggtcagggta ccctggttac cgtttct      357

<210> SEQ ID NO 222
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 222
```

```
gaagttcagc tggttgaatc tggtggtggt ctggttcagc cgggtggttc tctgcgtctg    60
tcttgcgcgg cgtctcagtc tatcttctct aaccactgga tgaactgggt tcgtcaggcg   120
ccgggtaaag gtctggaatg gatcggtgaa atccgttcta atctctatca cggtgcgacc   180
tcttacgcgg aatctgttaa aggtcgtttc atcatctctc gtgacggtaa cggtacctct   240
ctgaccctgg aaatgaactc tctgaaaacc gaagacaccg cggaatacta ctgcgcgcag   300
aactactacg gttctaccta cgactactgg ggtcagggta ccctggttac cgtttct     357
```

<210> SEQ ID NO 223
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 223

```
gaagttcagc tgaccgaatc tggtggtggt ctggttcagc cgggtggttc tctgcgtctg    60
tcttgccgtg cgtctcagtc taccttctct aaccactaca tgaactgggt tcgtcaggcg   120
ccgggtaaag gtctggaatg gatcggtgaa atccgttcta atctctatca ctctgcgacc   180
tcttacgcgg aatctgttaa aggtcgtttc atcatctctc gtgacggtaa cggtaacgac   240
ctgaccctgg aaatgaactc tctgaaaacc gaagacaccg cggaatacta ctgcgcgcgt   300
aactactacg gttctaccta cgactactgg ggtcagggta ccctggttac cgtttct     357
```

<210> SEQ ID NO 224
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 224

```
gaagttcagc tggttgaatc tggtggtggt ctggttcagc cgggtggttc tctgcgtctg    60
tcttgcgcgg cgtctcagtt caccttctct aaccactaca tgaactgggt tcgtcaggcg   120
ccgggtaaag gtctggaatg gatcggtgaa atccgttcta atctatcta cggtgcgacc   180 tcttacgcgg aatctgttaa aggtcgtttc atcatctctc gtgacgacaa cggtacctct   240
ctgtacctgg aaatgaactc tctgaaaacc gaagacaccg cggaatacta ctgcgcgcgt   300
aactactacg gttctaccta cgactactgg ggtcagggta ccctggttac cgtttct     357
```

<210> SEQ ID NO 225
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 225

```
gaagttcagc tgaccgaatc tggtggtggt ctggttcagc cgggtggttc tctgcgtttg    60
tcttgccgtg cgtctcagtc taccttctct aaccactaca tgaactgggt tcgtcaggcg   120
ccgggtaaag gtctggaatg gatcggtgaa atccgttcta atcttctaa ctctgcgacc   180 tcttacgcgg aatctgttaa aggtcgtttc atcatctctc gtgacggtaa cggtaacgac   240
ctgtacctgg aaatgaactc tctgaaaacc gaagacaccg cggaatacta ctgcgcgcag   300
aactactacg gttctaccta cgactactgg ggtcagggta ccctggttac cgtttct     357
```

<210> SEQ ID NO 226
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 226

```
gaagttcagc tgaccgaatc tggtggtggt ctggttcagc cgggtggttc tctgcgtctg      60
tcttgccgtg cgtctcagtc taccttctct aaccactgga tgaactgggt tcgtcaggcg     120
ccgggtaaag gtctggaatg gatcggtgaa atccgttcta atcttcttta cggtgcgacc     180
tcttacgcgg aatctgttaa aggtcgtttc atcatctctc gtgacggtaa cggtaactct     240
ctgacccctgg aaatgaactc tctgaaaacc gaagacaccg cggaatacta ctgcgcgcag     300
aactactacg gttctaccta cgactactgg ggtcagggta ccctggttac cgtttct       357
```

<210> SEQ ID NO 227
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 227

```
gaagttcagc tggttgaatc tggtggtggt ctggttcagc cgggtggttc tctgcgtctg      60
tcttgccgtg cgtctcagtc taccttctct aaccactaca tgaactgggt tcgtcaggcg     120
ccgggtaaag gtctggaatg gatcggtgaa atccgttcta atctatcaa ctctgcgacc     180
cactacgcgg aatctgttaa aggtcgtttc atcatctctc gtgacggtaa caaaaacgac     240
ctgacccctgg aaatgaactc tctgaaaacc gaagacaccg cggaatacta ctgcgcgcgt     300
aactactacg gttctaccta cgactactgg ggtcagggta ccctggttac cgtttct       357
```

<210> SEQ ID NO 228
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 228

```
gaagttcagc tggttgaatc tggtggtggt ctggttcagc cgggtggttc tctgcgtctg      60
tcttgcgcgg cgtctggttc taccttctct aaccactaca tgaactgggt tcgtcaggcg     120
ccgggtaaag gtctggaatg gatcggtgaa atccgttcta atctatcaa ctctgcgacc     180
tcttacgcgg aatctgttaa aggtcgtttc atcatctctc gtgacggtaa cggtacctct     240
ctgtacctgg aaatgaactc tctgaaaacc gaagacaccg cggaatacta ctgcgcgcgt     300
aactactacg gttctaccta cgactactgg ggtcagggta ccctggttac cgtttct       357
```

<210> SEQ ID NO 229
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 229

```
gaagttcagc tgaccgaatc tggtggtggt ctggttcagc cgggtggttc tctgcgtctg      60
tcttgccgtg cgtctcagtc taccttctct aaccactaca tgaactgggt tcgtcaggcg     120
```

```
ccgggtaaag gtctggaatg gatcggtgaa atccgttcta atcttctaa cggtgcgacc    180 tcttacgcgg aatctgttaa aggtcgtttc atcatctctc gtgacgacaa cggtaccgac    240
ctgaccctgg aaatgaactc tctgaaaacc gaagacaccg cggaatacta ctgcgcgcgt    300
aactactacg gttctacccc ggactactgg ggtcagggta ccctggttac cgtttct       357
```

<210> SEQ ID NO 230
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 230

```
gaagttcagc tggttgaatc tggtggtggt ctggttcagc cgggtggttc tctgcgtctg    60
tcttgcgcgg cgtctggttt caccttctct aaccactaca tgaactgggt tcgtcaggcg    120
ccgggtaaag gtctggaatg gatcggtgaa atccgttcta atcttctta ctctgcgacc    180 tcttacgcgg aatctgttaa aggtcgtttc atcatctctc gtgacgacaa caaaaactct    240
ctgaccctgg aaatgaactc tctgaaaacc gaagacaccg cggaatacta ctgcgcgcgt    300
aactactacg gttctacccc ggactactgg ggtcagggta ccctggttac cgtttct       357
```

<210> SEQ ID NO 231
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 231

```
gaagttcagc tggttgaatc tggtggtggt ctggttcagc cgggtggttc tctgcgtctg    60
tcttgccgtg cgtctggttc tatcttctct aaccactgga tgaactgggt tcgtcaggcg    120
ccgggtaaag gtctggaatg gatcggtgaa atccgttcta atctatcaa cggtgcgacc    180 tcttacgcgg aatctgttaa aggtcgtttc atcatctctc gtgacgacaa cgtaactct    240 ctgaccctgg aaatgaactc tctgaaaacc gaagacaccg cggaatacta ctgcgcgcag    300
aactactacg gttctacccc ggactactgg ggtcagggta ccctggttac cgtttct       357
```

<210> SEQ ID NO 232
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 232

```
gaagttcagc tgaccgaatc tggtggtggt ctggttcagc cgggtggttc tctgcgtctg    60
tcttgcgcgg cgtctggttt caccttctct aaccactgga tgaactgggt tcgtcaggcg    120
ccgggtaaag gtctggaatg gatcggtgaa atccgttcta atcttctta ctctgcgacc    180 cactacgcgg aatctgttaa aggtcgtttc atcatctctc gtgacgacaa caaaaccgac    240
ctgaccctgg aaatgaactc tctgaaaacc gaagacaccg cggaatacta ctgcgcgcgt    300
aactactacg gttctaccta cgactactgg ggtcagggta ccctggttac cgtttct       357
```

<210> SEQ ID NO 233
<211> LENGTH: 357
<212> TYPE: DNA

<213> ORGANISM: Artificial Sequence
<220> FEATURE:
<223> OTHER INFORMATION: Infliximab VH variant

<400> SEQUENCE: 233

| | | | | | |
|---|---|---|---|---|---|
| gaagttcagc | tggttgaatc | tggtggtggt | ctggttcagc | cgggtggttc | tctgcgtctg | 60 |
| tcttgccgtg | cgtcaggttt | catcttctct | aaccactgga | tgaactgggt | tcgtcaggcg | 120 |
| ccgggtaaag | gtctggaatg | gatcggtgaa | atccgttcta | aatctatcta | ctctgcgacc | 180 |
| cactacgcgg | aatctgttaa | aggtcgtttc | atcatctctc | gtgacggtaa | cggtaacgac | 240 |
| ctgaccctgg | aaatgaactc | tctgaaaacc | gaagacaccg | cggaatacta | ctgcgcgcgt | 300 |
| aactactacg | gttctacccc | ggactactgg | ggtcagggta | ccctggttac | cgtttct | 357 |

<210> SEQ ID NO 234
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 234

| | | | | | |
|---|---|---|---|---|---|
| gaagttcagc | tggttgaatc | tggtggtggt | ctggttcagc | cgggtggttc | tctgcgtctg | 60 |
| tcttgccgtg | cgtctggttc | taccttctct | aaccactaca | tgaactgggt | tcgtcaggcg | 120 |
| ccgggtaaag | gtctggaatg | gatcggtgaa | atccgttcta | aatcttctta | cggtgcgacc | 180 |
| tcttacgcgg | aatctgttaa | aggtcgtttc | atcatctctc | gtgacggtaa | cggtaacgac | 240 |
| ctgtacctgg | aaatgaactc | tctgaaaacc | gaagacaccg | cggaatacta | ctgcgcgcag | 300 |
| aactactacg | gttctacccc | ggactactgg | ggtcagggta | ccctggttac | cgtttct | 357 |

<210> SEQ ID NO 235
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 235

| | | | | | |
|---|---|---|---|---|---|
| gaagttcagc | tggttgaatc | tggtggtggt | ctggttcagc | cgggtggttc | tctgcgtctg | 60 |
| tcttgccgtg | cgtctcagtc | tatcttctct | aaccactgga | tgaactgggt | tcgtcaggcg | 120 |
| ccgggtaaag | gtctggaatg | gatcggtgaa | atccgttcta | aatctatcaa | ctctgcgacc | 180 |
| cactacgcgg | aatctgttaa | aggtcgtttc | atcatctctc | gtgacgacaa | cggtacctct | 240 |
| ctgtacctgg | aaatgaactc | tctgaaaacc | gaagacaccg | cggaatacta | ctgcgcgcgt | 300 |
| aactactacg | gttctacccc | ggactactgg | ggtcagggta | ccctggttac | cgtttct | 357 |

<210> SEQ ID NO 236
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 236

| | | | | | |
|---|---|---|---|---|---|
| gaagttcagc | tgaccgaatc | tggtggtggt | ctggttcagc | cgggtggttc | tctgcgtctg | 60 |
| tcttgccgtg | cgtctcagtt | catcttctct | aaccactaca | tgaactgggt | tcgtcaggcg | 120 |
| ccgggtaaag | gtctggaatg | gatcggtgaa | atccgttcta | aatctatcta | cggtgcgacc | 180 |
| cactacgcgg | aatctgttaa | aggtcgtttc | atcatctctc | gtgacgacaa | caaaaccgac | 240 |

```
ctgtacctgg aaatgaactc tctgaaaacc gaagacaccg cggaatacta ctgcgcgcgt    300
aactactacg gttctaccta cgactactgg ggtcagggta ccctggttac cgtttct      357
```

<210> SEQ ID NO 237
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 237

```
gaagttcagc tgaccgaatc tggtggtggt ctggttcagc cgggtggttc tctgcgtctg    60
tcttgcgcgg cgtctcagtt catcttctct aaccactgga tgaactgggt tcgtcaggcg   120
ccgggtaaag gtctggaatg gatcggtgaa atccgttcta atcttctta cggtgcgacc   180 cactacgcgg aatctgttaa aggtcgtttc atcatctctc gtgacggtaa cggtaactct   240
ctgtacctgg aaatgaactc tctgaaaacc gaagacaccg cggaatacta ctgcgcgcag   300
aactactacg gttctaccta cgactactgg ggtcagggta ccctggttac cgtttct     357
```

<210> SEQ ID NO 238
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 238

```
gaagttcagc tgaccgaatc tggtggtggt ctggttcagc cgggtggttc tctgcgtctg    60
tcttgcgcgg cgtctcagtc tatcttctct aaccactaca tgaactgggt tcgtcaggcg   120
ccgggtaaag gtctggaatg gatcggtgaa atccgttcta atcttctta ctctgcgacc   180 tcttacgcgg aatctgttaa aggtcgtttc atcatctctc gtgacgacaa cggtaacgac   240
ctgacccggg aaatgaactc tctgaaaacc gaagacaccg cggaatacta ctgcgcgcag   300
aactactacg gttctacccc ggactactgg ggtcagggta ccctggttac cgtttct     357
```

<210> SEQ ID NO 239
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 239

```
gaagttcagc tgaccgaatc tggtggtggt ctggttcagc cgggtggttc tctgcgtctg    60
tcttgccgtg cgtctggttt catcttctct aaccactaca tgaactgggt tcgtcaggcg   120
ccgggtaaag gtctggaatg gatcggtgaa atccgttcta atcttctta ctctgcgacc   180 tcttacgcgg aatctgttaa aggtcgtttc atcatctctc gtgacggtaa caaaaacgac   240
ctgacccggg aaatgaactc tctgaaaacc gaagacaccg cggaatacta ctgcgcgcgt   300
aactactacg gttctaccta cgactactgg ggtcagggta ccctggttac cgtttct     357
```

<210> SEQ ID NO 240
<211> LENGTH: 357
<212> TYPE: DNA
<213> ORGANISM: Artificial Sequence
<220> FEATURE:
<223> OTHER INFORMATION: Infliximab VH variant

```
<400> SEQUENCE: 240
gaagttcagc tggttgaatc tggtggtggt ctggttcagc cgggtggttc tctgcgtctg    60
tcttgccgtg cgtctggttc tatcttctct aaccactgga tgaactgggt tcgtcaggcg   120
ccgggtaaag gtctggaatg gatcggtgaa atccgttcta atcttcttc ctctgcgacc   180 cactacgcgg aatctgttaa aggtcgtttc atcatctctc gtgacggtaa cggtaactct   240
ctgaccctgg aaatgaactc tctgaaaacc gaagacaccg cggaatacta ctgcgcgcgt   300
aactactacg gttctaccta cgactactgg ggtcagggta ccctggttac cgtttct      357

<210> SEQ ID NO 241
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 241
gaagttcagc tgaccgaatc tggtggtggt ctggttcagc cgggtggttc tctgcgtctg    60
tcttgccgtg cgtctcagtc taccttctct aaccactgga tgaactgggt tcgtcaggcg   120
ccgggtaaag gtctggaatg gatcggtgaa atccgttcta atcttcttc cggtgcgacc   180 cactacgcgg aatctgttaa aggtcgtttc atcatctctc gtgacgacaa cggtaccgac   240
ctgaccctgg aaatgaactc tctgaaaacc gaagacaccg cggaatacta ctgcgcgcgt   300
aactactacg gttctaccta cgactactgg ggtcagggta ccctggttac cgtttct      357

<210> SEQ ID NO 242
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 242
gaagttcagc tgaccgaatc tggtggtggt ctggttcagc cgggtggttc tctgcgtctg    60
tcttgcgcgg cgtctggttc tatcttctct aaccactaca tgaattgggt tcgtcaggcg   120
ccgggtaaag gtctggaatg gatcggtgaa atccgttcta atctatcta cggtgcgacc   180 tcttacgcgg aatctgttaa aggtcgtttc atcatctctc gtgacggtaa cggtaactct   240
ctgtacctgg aaatgaactc tctgaaaacc gaagacaccg cggaatacta ctgcgcgcag   300
aactactacg gttctacccc cggactactgg ggtcagggta ccctggttac cgtttct     357

<210> SEQ ID NO 243
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 243
gaagttcagc tgaccgaatc tggtggtggt ctggttcagc cgggtggttc tctgcgtctg    60
tcttgccgtg cgtctggttc tatcttctct aaccactaca tgaactgggt tcgtcaggcg   120
ccgggtaaag gtctggaatg gatcggtgaa atccgttcta atcttcttc cggtgcgacc   180 cactacgcgg aatctgttaa aggtcgtttc atcatctctc gtgacggtaa cggtaccgac   240
ctgaccctgg aaatgaactc tctgaaaacc gaagacaccg cggaatacta ctgcgcgcag   300
aactactacg gttctaccta cgactactgg ggtcagggta ccctggttac cgtttct      357
```

<210> SEQ ID NO 244
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 244

```
gaagttcagc tggttgaatc tggtggtggt ctggttcagc cgggtggttc tctgcgtctg      60
tcttgccgtg cgtctcagtc tatcttctct aaccactaca tgaactgggt tcgtcaggcg     120
ccgggtaaag gtctggaatg gatcggtgaa atccgttcta atcttctta cggtgcgacc      180
cactacgcgg aatctgttaa aggtcgtttc atcatctctc gtgacgacaa caaaaactct     240
ctgtacctgg aaatgaactc tctgaaaacc gaagacaccg cggaatacta ctgcgcgcgt     300
aactactacg gttctaccta cgactactgg ggtcaggata ccctggttac cgtttct       357
```

<210> SEQ ID NO 245
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 245

```
gaagttcagc tgaccgaatc tggtggtggt ctggttcagc cgggtggttc tctgcgtctg      60
tcttgcgcgg cgtctggttt catcttctct aaccactgga tgaactgggt tcgtcaggcg     120
ccgggtaaag gtctggaatg gatcggtgaa atccgttcta atcttctta ctctgcgacc      180
cactacgcgg aatctgttaa aggtcgtttc atcatctctc gtgacgacaa cggtacctct     240
ctgtacctgg aaatgaactc tctgaaaacc gaagacaccg cggaatacta ctgcgcgcag     300
aactactacg gttctaccta cgactactgg ggtcagggta ccctggttac cgtttct       357
```

<210> SEQ ID NO 246
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 246

```
gaagttcagc tgaccgaatc tggtggtggt ctggttcagc cgggtggttc tctgcgtctg      60
tcttgcgcgg cgtctcagtt catcttctct aaccactgga tgaactgggt tcgtcaggcg     120
ccgggtaaag gtctggaatg gatcggtgaa atccgttcta atcttctaa ctctgcgacc      180
tcttacgcgg aatctgttaa aggtcgtttc atcatctctc gtgacgacaa cggtaacgac     240
ctgtacctgg aaatgaactc tctgaaaacc gaagacaccg cggaatacta ctgcgcgcag     300
aactactacg gttctaccta cgactactgg ggtcagggta ccctggttac cgtttct       357
```

<210> SEQ ID NO 247
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 247

```
gaagttcagc tggttgaatc tggtggtggt ctggttcagc cgggtggttc tctgcgtctg      60
```

```
tcttgccgtg cgtctcagtc tatcttctct aaccactgga tgaactgggt tcgtcaggcg    120
ccgggtaaag gtctggaatg gatcggtgaa atccgttcta aatctatcaa ctctgcgacc    180
tcttacgcgg aatctgttaa aggtcgtttc atcatctctc gtgacgacaa cggtacctct    240
ctgtacctgg aaatgaactc tctgaaaacc gaagacaccg cggaatacta ctgcgcgcag    300
aactactacg gttctaccta cgactactgg ggtcagggta ccctggttac cgtttct      357

<210> SEQ ID NO 248
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 248
gaagttcagc tgaccgaatc tggtggtggt ctggttcagc cgggtggttc tctgcgtctg     60
tcttgccgtg cgtctcagtc taccttctct aaccactgga tgaactgggt tcgtcaggcg    120
ccgggtaaag gtctggaatg gatcggtgaa atccgttcta aatctatcaa cggtgcgacc    180
tcttacgcgg aatctgttaa aggtcgtttc atcatctctc gtgacgacaa cggtaactct    240
ctgaccctgg aaatgaactc tctgaaaacc gaagacaccg cggaatacta ctgcgcgcag    300
aactactacg gttctaccta cgactactgg ggtcagggta ccctggttac cgtttct      357

<210> SEQ ID NO 249
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 249
gaagttcagc tggttgaatc tggtggtggt ctggttcagc cgggtggttc tctgcgtctg     60
tcttgccgtg cgtctggttt catcttctct aaccactaca tgaactgggt tcgtcaggcg    120
ccgggtaaag gtctggaatg gatcggtgaa atccgttcta aatctatcta cggtgcgacc    180
cactacgcgg aatctgttaa aggtcgtttc atcatctctc gtgacggtaa cggtaacgac    240
ctgtacctgg aaatgaactc tctgaaaacc gaagacaccg cggaatacta ctgcgcgcgt    300
aactactacg gttctaccta cgactactgg ggtcagggta ccctggttac cgtttct      357

<210> SEQ ID NO 250
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 250
gaagttcagc tgaccgaatc tggtggtggt ctggttcagc cgggtggttc tctgcgtctg     60
tcttgcgcgg cgtctcagtc taccttctct aaccactgga tgaactgggt tcgtcaggcg    120
ccgggtaaag gtctggaatg gatcggtgaa atccgttcta aatcttctaa cggtgcgacc    180
tcttacgcgg aatctgttaa aggtcgtttc atcatctctc gtgacggtaa caaaaactct    240
ctgaccctgg aaatgaactc tctgaaaacc gaagacaccg cggaatacta ctgcgcgcgt    300
aactactacg gttctaccta cgactactgg ggtcagggta ccctggttac cgtttct      357

<210> SEQ ID NO 251
<211> LENGTH: 357
```

```
<212> TYPE: DNA
<213> ORGANISM: Artificial Sequence
<220> FEATURE:
<223> OTHER INFORMATION: Infliximab VH variant

<400> SEQUENCE: 251
gaagttcagc tgaccgaatc tggtggtggt ctggttcagc cgggtggttc tctgcgtctg      60
tcttgccgtg cgtctggttt caccttctct aaccactaca tgaactgggt tcgtcaggcg     120
ccgggtaaag gtctggaatg gatcggtgaa atccgttcta atctatcta cggtgcgacc      180 tcttacgcgg aatctgttaa aggtcgtttc atcatctctc gtgacggtaa cggtaccgac     240
ctgaccctgg aaatgaactc tctgaaaacc gaagacaccg cggaatacta ctgcgcgcag     300
aactactacg gttctaccta cgactactgg ggtcaggta ccctggttac cgtttct        357

<210> SEQ ID NO 252
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 252
gaagttcagc tgaccgaatc tggtggtggt ctggttcagc cgggtggttc tctgcgtctg      60
tcttgcgcgg cgtctcagtt caccttctct aaccactgga tgaactgggt tcgtcaggcg     120
ccgggtaaag gtctggaatg gatcggtgaa atccgttcta atctatcta cggtgcgacc      180 cactacgcgg aatctgttaa aggtcgtttc atcatctctc gtgacgacaa caaaaacctct    240 ctgtacctgg aaatgaactc tctgaaaacc gaagacaccg cggaatacta ctgcgcgcgt     300
aactactacg gttctacccc ggactactgg ggtcaggta ccctggttac cgtttct         357

<210> SEQ ID NO 253
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 253
gaagttcagc tggttgaatc tggtggtggt ctggttcagc cgggtggttc tctgcgtctg      60
tcttgccgtg cgtctggttt catcttctct aaccactgga tgaactgggt tcgtcaggcg     120
ccgggtaaag gtctggaatg gatcggtgaa atccgttcta atctatcta cggtgcgacc      180 cactacgcgg aatctgttaa aggtcgtttc atcatctctc gtgacgacaa caaaaactct    240
ctgtacctgg aaatgaactc tctgaaaacc gaagacaccg cggaatacta ctgcgcgcag     300
aactactacg gttctaccta cgactactgg ggtcaggta ccctggttac cgtttct         357

<210> SEQ ID NO 254
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 254
gaagttcagc tgaccgaatc tggtggtggt ctggttcagc cgggtggttc tctgcgtctg      60
tcttgccgtg cgtctggttt caccttctct aaccactaca tgaactgggt tcgtcaggcg     120
ccgggtaaag gtctggaatg gatcggtgaa atccgttcta atctatcta ctctgcgacc      180
```

```
cactacgcgg aatctgttaa aggtcgtttc atcatctctc gtgacgacaa caaaaccgac    240
ctgaccctgg aaatgaactc tctgaaaacc gaagacaccg cggaatacta ctgcgcgcgt    300
aactactacg gttctaccta cgactactgg ggtcagggta ccctggttac cgtttct       357

<210> SEQ ID NO 255
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 255
gaagttcagc tgaccgaatc tggtggtggt ctggttcagc cgggtggttc tctgcgtctg    60
tcttgccgtg cgtctggttt caccttctct aaccactaca tgaactgggt tcgtcaggcg    120
ccgggtaaag gtctggaatg gatcggtgaa atccgttcta atctatcta ctctgcgacc    180 cactacgcgg aatctgttaa aggtcgtttc atcatctctc gtgacggtaa caaaaccgac    240
ctgaccctgg aaatgaactc tctgaaaacc gaagacaccg cggaatacta ctgcgcgcgt    300
aactactacg gttctacccc ggactactgg ggtcagggta ccctggttac cgtttct       357

<210> SEQ ID NO 256
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 256
gaagttcagc tgaccgaatc tggtggtggt ctggttcagc cgggtggttc tctgcgtctg    60
tcttgccgtg cgtctcagtt catcttctct aaccactgga tgaactgggt tcgtcaggcg    120
ccgggtaaag gtctggaatg gatcggtgaa atccgttcta atctatcaa ctctgcgacc    180 cactacgcgg aatctgttaa aggtcgtttc atcatctctc gtgacgacaa caaaaacgac    240
ctgaccctgg aaatgaactc tctgaaaacc gaagacaccg cggaatacta ctgcgcgcgt    300
aactactacg gttctaccta cgactactgg ggtcagggta ccctggttac cgtttct       357

<210> SEQ ID NO 257
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 257
gaagttcagc tggttgaatc tggtggtggt ctggttcagc cgggtggttc tctgcgtctg    60
tcttgccgtg cgtctcagtt caccttctct aaccactgga tgaactgggt tcgtcaggcg    120
ccgggtaaag gtctggaatg gatcggtgaa atccgttcta atcttctaa ctctgcgacg    180 cactacgcgg aatctgttaa aggtcgtttc atcatctctc gtgacggtaa cggtaactct    240
ctgtacctgg aaatgaactc tctgaaaacc gaagacaccg cggaatacta ctgcgcgcgt    300
aactactacg gttctaccta cgactactgg ggtcagggta ccctggttac cgtttct       357

<210> SEQ ID NO 258
<211> LENGTH: 357
<212> TYPE: DNA
<213> ORGANISM: Artificial Sequence
<220> FEATURE:
<223> OTHER INFORMATION: Infliximab VH variant
```

<400> SEQUENCE: 258

```
gaagttcagc tgaccgaatc tggtggtggt ctggttcagc cgggtggttc tctgcgtctg    60
tcttgccgtg cgtctcagtc tatcttctct aaccactgga tgaactgggt tcgtcaggcg   120
ccgggtaaag gtctggaatg gatcggtgaa atccgttcta aatctatcaa cggtgcgacc   180
cactacgcgg aatctgttaa aggtcgtttc atcatctctc gtgacgacaa caaaaacgac   240
ctgtacctgg aaatgaactc tctgaaaacc gaagacaccg cggaatacta ctgcgcgcgt   300
aactactacg gttctaccta cgactactgg ggtcaggtta ccctggttac cgtttct     357
```

<210> SEQ ID NO 259
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 259

```
gaagttcagc tgaccgaatc tggtggtggt ctggttcagc cgggtggttc tctgcgtctg    60
tcttgccgtg cgtctggttc taccttctct aaccactgga tgaactgggt tcgtcaggcg   120
ccgggtaaag gtctggaatg gatcggtgaa atccgttcta atctatcta cggtgcgacc   180
tcttacgcgg aatctgttaa aggtcgtttc atcatctctc gtgacggtaa caaacctct   240
ctgaccctgg aaatgaactc tctgaaaacc gaagacaccg cggaatacta ctgcgcgcgt   300
aactactacg gttctacccc ggactactgg ggtcaggta ccctggttac cgtttct     357
```

<210> SEQ ID NO 260
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 260

```
gaagttcagc tgaccgaatc tggtggtggt ctggttcagc cgggtggttc tctgcgtctg    60
tcttgccgtg cgtctggttc tatcttctct aaccactaca tgaactgggt tcgtcaggcg   120
ccgggtaaag gtctggaatg gatcggtgaa atccgttcta atctatcta ctctgcgacc   180
cactacgcgg aatctgttaa aggtcgtttc atcatctctc gtgacggtaa cggtacctct   240
ctgtacctgg aaatgaactc tttgaaaacc gaagacaccg cggaatacta ctgcgcgcag   300
aactactacg gttctaccta cgactactgg ggtcagggta ccctggttac cgtttct     357
```

<210> SEQ ID NO 261
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 261

```
gaagttcagc tggttgaatc tggtggtggt ctggttcagc cgggtggttc tctgcgtctg    60
tcttgccgtg cgtctggttc tatcttctct aaccactaca tgaactgggt tcgtcaggcg   120
ccgggtaaag gtctggaatg gatcggtgaa atccgttcta atcttctta cggtgcgacc   180
tcttacgcgg aatctgttaa aggtcgtttc atcatctctc gtgacgacaa caaaaacgac   240
ctgaccctgg aaatgaactc tctgaaaacc gaagacaccg cggaatacta ctgcgcgcag   300
```

```
aactactacg gttctacccc ggactactgg ggtcaggta ccctggttac cgtttct        357
```

<210> SEQ ID NO 262
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 262

```
gaagttcagc tgaccgaatc tggtggtggt ctggttcagc cgggtggttc tctgcgtctg    60
tcttgcgcgg cgtctggttc taccttctct aaccactgga tgaactgggt tcgtcaggcg   120
ccgggtaaag gtctggaatg gatcggtgaa atccgttcta atcttctta ctctgcgacc    180
tcttacgcgg aatctgttaa aggtcgtttc atcatctctc gtgacgacaa caaaaactct   240
ctgaccctgg aaatgaactc tctgaaaacc gaagacaccg cggaatacta ctgcgcgcgt   300
aactactacg gttctacccc ggactactgg ggtcagggta ccctggttac cgtttct     357
```

<210> SEQ ID NO 263
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 263

```
gaagttcagc tggttgaatc tggtggtggt ctggttcagc cgggtggttc tctgcgtctg    60
tcttgccgtg cgtctggttt caccttctct aaccactgga tgaactgggt tcgtcaggcg   120
ccgggtaaag gtctggaatg gatcggtgaa atccgttcta atctatcta ctctgcgacc    180
cactacgcgg aatctgttaa aggtcgtttc atcatctctc gtgacgacaa caaaaactct   240
ctgaccctgg aaatgaactc tctgaaaacc gaagacaccg cggaatacta ctgcgcgcgt   300
aactactacg gttctacccc ggactactgg ggtcaggta ccctggttac cgtttct       357
```

<210> SEQ ID NO 264
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 264

```
gaagttcagc tgaccgaatc tggtggtggt ctggttcagc cgggtggttc tctgcgtctg    60
tcttgccgtg cgtctggttt catcttctct aaccactaca tgaactgggt tcgtcaggcg   120
ccgggtaaag gtctggaatg gatcggtgaa atccgttcta atctatcaa cggtgcgacc    180
cactacgcgg aatctgttaa aggtcgtttc atcatctctc gtgacgacaa cggtacctct   240
ctgtacctgg aaatgaactc tctgaaaacc gaagacaccg cggaatacta ctgcgcgcgt   300
aactactacg gttctaccta cgactactgg ggtcagggta ccctggttac cgtttct      357
```

<210> SEQ ID NO 265
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 265

```
gaagttcagc tggttgaatc tggtggtggt ctggttcagc cgggtggttc tctgcgtctg    60
```

-continued

```
tcttgcgcgg cgtctggttc taccttctct aaccactaca tgaactgggt tcgtcaggcg      120
ccgggtaaag gtctggaatg gatcggtgaa atccgttcta atctatctat ctctgcgacc      180
tcttacgcgg aatctgttaa aggtcgtttt atcatctctc gtgacgacaa cggtaactct      240
ctgtacctgg aaatgaactc tctgaaaacc gaagacaccg cggaatacta ctgcgcgcag      300
aattactacg gttctaccta cgactactgg ggtcagggta ccctggttac cgtttct      357
```

<210> SEQ ID NO 266
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 266

```
gaagttcagc tgaccgaatc tggtggtggt ctggttcagc cgggtggttc tctgcgtctg      60
tcttgccgtg cgtctcagtc taccttctct aaccactaca tgaactgggt tcgtcaggcg      120
ccgggtaaag gtctggaatg gatcggtgaa atccgttcta atcttcttac ggtgcgacc       180 tcttacgcgg aatctgttaa aggtcgtttc atcatctctc gtgacgacaa cggtacctct      240
ctgtacctgg aaatgaactc tctgaaaacc gaagacaccg cggaatacta ctgcgcgcag      300
aactactacg gttctacccc ggactactgg ggtcagggta ccctggttac cgtttct       357
```

<210> SEQ ID NO 267
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 267

```
gaagttcagc tggttgaatc tggtggtggt ctggttcagc cgggtggttc tctgcgtcta      60
tcttgcgcgg cgtctcagtc tatcttctct aaccactaca tgaactgggt tcgtcaggcg      120
ccgggtaaag gtctggaatg gatcggtgaa atccgttcta atctatctat cggtgcgacc      180
cactacgcgg aatctgttaa aggtcgtttc atcatctctc gtgacggtaa caaaaacgac      240
ctgaccctgg aaatgaactc tctgaaaacc gaagacaccg cggaatacta ctgcgcgcgt      300
aactactacg gttctacccc ggactactgg ggtcagggta ccctggttac cgtttct       357
```

<210> SEQ ID NO 268
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 268

```
gaagttcagc tggttgaatc tggtggtggt ctggttcagc cgggtggttc tctgcgtctg      60
tcttgccgtg cgtctcagtt catcttctct aaccactaca tgaactgggt tcgtcaggcg      120
ccgggtaaag gtctggaatg gatcggtgaa atccgttcta atccatcaa cggtgcgacc       180 cactacgcgg aatctgttaa aggtcgtttc atcatctctc gtgacggtaa cggtaccgac      240
ctgtacctgg aaatgaactc tctgaaaacc gaagacaccg cggaatacta ctgcgcgcgt      300
aactactacg gttctacccc ggactactgg ggtcagggta ccctggttac cgtttct       357
```

<210> SEQ ID NO 269

<211> LENGTH: 357
<212> TYPE: DNA
<213> ORGANISM: Artificial Sequence
<220> FEATURE:
<223> OTHER INFORMATION: Infliximab VH variant

<400> SEQUENCE: 269

```
gaagttcagc tggttgaatc tggtggtggt ctggttcagc cgggtggttc tctgcgtctg        60
tcttgccgtg cgtctggttc taccttctct aaccactaca tgaactgggt tcgtcaggcg       120
ccgggtaaag gtctggaatg gatcggtgaa atccgttcta atctatcaa ctctgcgacc        180
tcttacgcgg aatctgttaa aggtcgtttc atcatctctc gtgacggtaa cggtaccgac       240
ctgaccctgg aaatgaactc tctgaaaacc gaagacaccg cggaatacta ctgcgcgcag       300
aactactacg gttctaccta cgactactgg ggtcaggyta ccctggttac cgtttct         357
```

<210> SEQ ID NO 270
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 270

```
gaagttcagc tggttgaatc tggtggtggt ctggttcagc cgggtggttc tctgcgtctg        60
tcttgccgtg cgtctcagtc tatcttctct aaccactaca tgaactgggt tcgtcaggcg       120
ccgggtaaag gtctggaatg gatcggtgaa atccgttcta atctatcta ctctgcgacc        180
cactacgcgg aatctgttaa aggtcgtttc atcatctctc gtgacggtaa cggtaacgac       240
ctgaccctgg aaatgaactc tctgaaaacc gaagacaccg cggaatacta ctgcgcgcgt       300
aactactacg gttctacccc ggactactgg ggtcaggyta ccctggttac cgtttct         357
```

<210> SEQ ID NO 271
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 271

```
gaagttcagc tgaccgaatc tggtggtggt ctggttcagc cgggtggttc tctgcgtctg        60
tcttgccgtg cgtctggttt catcttctct aaccactaca tgaactgggt tcgtcaggcg       120
ccgggtaaag gtctggaatg gatcggtgaa atccgttcta atctatcaa cggtgcgacc        180
tcttacgcgg aatctgttaa aggtcgtttc atcatctctc gtgacgacaa cggtaactct       240
ctgtacctgg aaatgaactc tctgaaaacc gaagacaccg cggaatacta ctgcgcgcgt       300
aactactacg gttctacccc ggactactgg ggtcagggta ccctggttac cgtttct         357
```

<210> SEQ ID NO 272
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 272

```
gaagttcagc tggttgaatc tggtggtggt ctggttcagc cgggtggttc tctgcgtctg        60
tcttgcgcgg cgtcacagtc taccttctct aaccactgga tgaactgggt tcgtcaggcg       120
ccgggtaaag gtctggaatg gatcggtgaa atccgttcta atcttcttta ctctgcgacc       180
```

-continued

```
cactacgcgg aatctgttaa aggtcgtttc atcatctctc gtgacggtaa caaaaacgac    240
ctgtacctgg aaatgaactc tctgaaaacc gaagacaccg cggaatacta ctgcgcgcgt    300
aactactacg gttctactta cgactactgg ggtcagggta ccctggttac cgtttct       357

<210> SEQ ID NO 273
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 273
gaagttcagc tgaccgaatc tggtggtggt ctggttcagc cgggtggttc tctgcgtctg    60
tcttgccgtg cgtctggttt catcttctct aaccactgga tgaactgggt tcgtcaggcg    120
ccgggtaaag gtctggaatg gatcggtgaa atccgttcta atcttctaa cggtgcgacc     180 tcttacgcgg aatctgttaa aggtcgtttc atcatctctc gtgacggtaa cggtacctct    240 ctgacccctgg aaatgaactc tctgaaaacc gaagacaccg cggaatacta ctgcgcgcag    300
aactactacg gttctaccta cgactactgg ggtcagggta ccctggttac cgtttct       357

<210> SEQ ID NO 274
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 274
gaagttcagc tgaccgaatc tggtggtggt ctggttcagc cgggtggttc tctgcgtctg    60
tcttgcgcgg cgtctcagtc tatcttctct aaccactaca tgaactgggt tcgtcaggcg    120
ccgggtaaag gtctggaatg gatcggtgaa atccgttcta atctatcta cggtgcgacc     180 cactacgcgg aatctgttaa aggtcgtttc atcatctctc gtgacgacaa cggtaccgac    240 ctgacccctgg aaatgaactc tctgaaaacc gaagacaccg cggaatacta ctgcgcgcag    300
aactactacg gttctacccc ggactactgg ggtcagggta ccctggttac cgtttct       357

<210> SEQ ID NO 275
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 275
gaagttcagc tggttgaatc tggtggtggt ctggttcagc cgggtggttc tctgcgtctg    60
tcttgcgcgg cgtctggttt caccttctct aaccactgga tgaactgggt tcgtcaggcg    120
ccgggtaaag gtctggaatg gatcggtgaa atccgttcta atcttctaa ctctgcgacc     180 cactacgcgg aatctgttaa aggtcgtttc atcatctctc gtgacggtaa caaaaccctct   240 ctgtacctgg aaatgaactc tctgaaaacc gaagacaccg cggaatacta ctgcgcgcgt    300
aactattacg gttctaccta cgactactgg ggtcagggta ccctggttac cgtttct       357

<210> SEQ ID NO 276
<211> LENGTH: 357
<212> TYPE: DNA
<213> ORGANISM: Artificial Sequence
<220> FEATURE:
```

<223> OTHER INFORMATION: Infliximab VH variant

<400> SEQUENCE: 276

```
gaagttcagc tggttgaatc tggtggtggt ctggttcagc cgggtggttc tctgcgtctg      60
tcttgcgcgg cgtctggttt caccttctct aaccactgga tgaactgggt tcgtcaggcg     120
ccgggtaaag gtctggaatg gatcggtgaa atccgttcta atcttctaa ctctgcgacc      180
tcttacgcgg aatctgttaa aggtcgtttc atcatctctc gtgacggtaa caaaaacgac     240
ctgaccctgg aaatgaactc tctgaaaacc gaagacaccg cggaatacta ctgcgcgcgt     300
aactactacg gttctaccta cgactactgg ggtcaggta ccctggttac cgtttct         357
```

<210> SEQ ID NO 277
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 277

```
gaagttcagc tggttgaatc tggtggtggt ctggttcagc cgggtggttc tctgcgtctg      60
tcttgccgtg cgtctcagtt caccttctct aaccactaca tgaactgggt tcgtcaggcg     120
ccgggtaaag gtctggaatg gatcggtgaa atccgttcta atctatcaa cggtgcgacc      180
tcttacgcgg aatctgttaa aggtcgtttc atcatctctc gtgacgacaa cggtaccgac     240
ctgtacctgg aaatgaactc tctgaaaacc gaagacaccg cggaatacta ctgcgcgcgt     300
aactactacg gttctaccta cgactactgg ggtcaggta ccctggttac cgtttct         357
```

<210> SEQ ID NO 278
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 278

```
gaagttcagc tgaccgaatc tggtggtggt ctggttcagc cgggtggttc tctgcgtctg      60
tcttgccgtg cgtctcagtt catcttctct aaccactaca tgaactgggt tcgtcaggcg     120
ccgggtaaag gtctggaatg gatcggtgaa atccgttcta atctatcaa cggtgcgacc      180
cactacgcgg aatctgttaa aggtcgtttc atcatctctc gtgacgacaa cggtaccgac     240
ctgaccctgg aaatgaactc tctgaaaacc gaagacaccg cggaatacta ctgcgcgcgt     300
aactactacg gttctaccc ggactactgg ggtcaggta ccctggttac cgtttct          357
```

<210> SEQ ID NO 279
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 279

```
gaagttcagc tgaccgaatc tggtggtggt ctggttcagc cgggtggttc tctgcgtctg      60
tcttgcgcgg cgtctcagtc tatcttctct aaccactaca tgaactgggt tcgtcaggcg     120
ccgggtaaag gtctggaatg gatcggtgaa atccgttcta atctatcaa ctctgcgacc      180
cactacgcgg aatctgttaa aggtcgtttc atcatctctc gtgacggtaa caaaaacgac     240
ctgtacctgg aaatgaactc tctgaaaacc gaagacaccg cggaatacta ctgcgcgcgt     300
```

```
aactactacg gttctacccc ggactactgg ggtcaggta  ccctggttac cgtttct      357
```

<210> SEQ ID NO 280
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 280

```
gaagttcagc tggttgaatc tggtggtggt ctggttcagc cgggtggttc tctgcgtctg      60
tcttgcgcgg cgtctggttc tatcttctct aaccactgga tgaactgggt tcgtcaggcg     120
ccgggtaaag gtctggaatg gatcggtgaa atccgttcta atcttctaa ctctgcgacc      180
cactacgcgg aatctgttaa aggtcgtttc atcatctctc gtgacggtaa caaaaacgac     240
ctgaccctgg aaatgaactc tctgaaaacc gaagacaccg cggaatacta ctgcgcgcgt     300
aactactacg gttctaccta cgactactgg ggtcagggta cctggttac cgtttct       357
```

<210> SEQ ID NO 281
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 281

```
gaagttcagc tgaccgaatc tggtggtggt ctggtacagc cgggtggttc tctgcgtctg      60
tcttgtcgtg cgtctggttt caccttctct aaccactaca tgaactgggt tcgtcaggcg     120
ccgggtaaag gtctggaatg gatcggtgaa atccgttcta atcttcttta cggtgcgacc     180
cactacgcgg aatctgttaa aggtcgtttc atcatctctc gtgacgacaa cggtaccgac     240
ctgtacctgg aaatgaactc tctgaaaacc gaagacaccg cggaatacta ctgcgcgcag     300
aactactacg gttctacccc ggactactgg ggtcagggta cctggttac cgtttct       357
```

<210> SEQ ID NO 282
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 282

```
gaagttcagc tggttgaatc tggtggtggt ctggttcagc cgggtggttc tctgcgtcta      60
tcttgccgtg cgtctggttc tatcttctct aaccactgga tgaactgggt tcgtcaggcg     120
ccgggtaaag gtctggaatg gatcggtgaa atccgttcta atctatcaa cggtgcgacc      180
cactacgcgg aatctgttaa aggtcgtttc atcatctctc gtgacgacaa cggtacctct     240
ctgtacctgg aaatgaactc tctgaaaacc gaagacaccg cggaatacta ctgcgcgcgt     300
aactactacg gttctaccta cgactactgg ggtcagggta cctggttac cgtttct       357
```

<210> SEQ ID NO 283
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 283

```
gaagttcagc tgaccgaatc tggtggtggt ctggttcagc cgggtggttc tctgcgtctg    60
tcttgccgtg cgtctggttc taccttctct aaccactaca tgaactgggt tcgtcaggcg   120
ccgggtaaag gtctggaatg gatcggtgaa atccgttcta atcttctaa ctctgcgacc    180 tcttacgcgg aatctgttaa aggtcgtttc atcatctctc gtgacgacaa caaaacctct   240
ctgtacctgg aaatgaactc tctgaaaacc gaagacaccg cggaatacta ctgcgcgcgt   300
aattactacg gttctaccta cgactactgg ggtcagggta ccctggttac cgtttct      357
```

<210> SEQ ID NO 284
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 284

```
gaagttcagc tggttgaatc tggtggtggt ctggttcagc cgggtggttc tctgcgtctg    60
tcttgccgtg cgtctcagtc tatcttctct aaccactaca tgaactgggt tcgtcaggcg   120
ccgggtaaag gtctggaatg gatcggtgaa atccgttcta atctatcaa ctctgcgacc    180 cactacgcgg aatctgttaa aggtcgtttc atcatctctc gtgacgacaa cggtaactct   240
ctgacCctgg aaatgaactc tctaaaaacc gaagacaccg cggaatacta ctgcgcgcag   300
aactactacg gttctaccta cgactactgg ggtcagggta ccctggttac cgtttct      357
```

<210> SEQ ID NO 285
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 285

```
gaagttcagc tgaccgaatc tggtggtggt ctggttcagc cgggtggttc tctgcgtctg    60
tcttgccgtg cgtctggttc taccttctct aaccactgga tgaactgggt tcgtcaggcg   120
ccgggtaaag gtctggaatg gatcggtgaa atccgttcta atcttctaa cggtgcgacc    180 tcttacgcgg aatctgttaa aggtcgtttc atcatctctc gtgacgacaa cggtaccgac   240
ctgtacctgg aaatgaactc tctgaaaacc gaagacaccg cggaatacta ctgcgcgcag   300
aactactacg gttctaccta cgactactgg ggtcagggta ccctggttac cgtttct      357
```

<210> SEQ ID NO 286
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 286

```
gaagttcagc tgaccgaatc tggtggtggt ctggttcagc cgggtggttc tctgcgtctg    60
tcttgccgtg cgtctggttt caccttctct aaccactgga tgaactgggt tcgtcaggcg   120
ccgggtaaag gtctggaatg gatcggtgaa atccgttcta atcttctaa cggtgcgacc    180 cactacgcgg aatctgttaa aggtcgtttc atcatctctc gtgacggtaa caaaaccgac   240
ctgtacctgg aaatgaactc tctgaaaacc gaagacaccg cggaatacta ctgcgcgcgt   300
aactactacg gttctaccCc ggactactgg ggtcagggta ccctggttac cgtttct      357
```

<210> SEQ ID NO 287
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 287

```
gaagttcagc tggttgaatc tggtggtggt ctggttcagc cgggtggttc tctgcgtctg      60
tcttgcgcgg cgtctggttc tatcttctct aaccactaca tgaactgggt tcgtcaggcg     120
ccgggtaaag gtctggaatg gatcggtgaa atccgttcta atcttctaa cggtgcgacc      180
cactacgcgg aatctgttaa aggtcgtttc atcatctctc gtgacgacaa caaaaactct     240
ctgtacctgg aaatgaactc tctgaaaacc gaagacaccg cggaatacta ctgcgcgcag     300
aactactacg gttctaccta cgactactgg ggtcaggta ccctggttac cgtttct        357
```

<210> SEQ ID NO 288
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 288

```
gaagttcagc tgaccgaatc tggtggtggt ctggttcagc cgggtggttc tctgcgtctg      60
tcttgccgtg cgtctcagtt catcttctct aaccactaca tgaactgggt tcgtcaggcg     120
ccgggtaaag gtctggaatg gatcggtgaa atccgttcta atctatcaa cggtgcgacc      180
cactacgcgg aatctgttaa aggtcgtttc atcatctctc gtgacgacaa caaaaccgac    240
ctgtacctgg aaatgaactc tctgaaaacc gaagacaccg cggaatacta ctgcgcgcgt     300
aactactacg gttctaccta cgactactgg ggtcagggta ccctggttac cgtttct       357
```

<210> SEQ ID NO 289
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 289

```
gaagttcagc tggttgaatc tggtggtggt ctggttcagc cgggtggttc tctgcgtctg      60
tcttgccgtg cgtctggttt caccttctct aaccactaca tgaactgggt tcgtcaggcg     120
ccgggtaaag gtctggaatg gatcggtgaa atccgttcta atcttctaa ctctgcgacc      180
tcttacgcgg aatctgttaa aggtcgtttc atcatctctc gtgacgacaa cggtaactct    240
ctgtacctgg aaatgaactc tctgaaaacc gaagacaccg cggaatacta ctgcgcgcag     300
aactactacg gttctacccc ggactactgg ggtcagggta ccctggttac cgtttct       357
```

<210> SEQ ID NO 290
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 290

```
gaagttcagc tggttgaatc tggtggtggt ctggttcagc cgggtggttc tctgcgtctg      60
tcttgccgtg cgtctggttt catcttctct aaccactgga tgaactgggt tcgtcaggcg     120
```

```
ccgggtaaag gtctggaatg gatcggtgaa atccgttcta aatctatcaa cggtgcgacc    180
cactacgcgg aatctgttaa aggtcgtttc atcatctctc gtgacgacaa caaaacctct    240
ctgtacctgg aaatgaactc tctgaaaacc gaagacaccg cggaatacta ctgcgcgcgt    300
aactactacg gttctaccta cgactactgg ggtcagggta ccctggttac cgtttct       357
```

```
<210> SEQ ID NO 291
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 291
gaagttcagc tgaccgaatc tggtggtggt ctggttcagc cgggtggttc tctgcgtctg    60
tcttgcgcgg cgtctcagtc taccttctct aaccactgga tgaactgggt tcgtcaggcg    120
ccgggtaaag gtctggaatg gatcggtgaa atccgttcta aatctatcaa cggtgcgacc    180
tcttacgcgg aatctgttaa aggtcgtttc atcatctctc gtgacgacaa cggtaactct    240
ctgaccctgg aaatgaactc tctgaaaacc gaagacaccg cggaatacta ctgcgcgcgt    300
aactactacg gttctacccc ggactactgg ggtcagggta ccctggttac cgtttct       357
```

```
<210> SEQ ID NO 292
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 292
gaagttcagc tgaccgaatc tggtggtggt ctggttcagc cgggtggttc tctgcgtctg    60
tcttgccgtg cgtctcagtt catcttctct aaccactaca tgaactgggt tcgtcaggcg    120
ccgggtaaag gtctggaatg gatcggtgaa atccgttcta aatctatcaa ctctgcgacc    180
cactacgcgg aatctgttaa aggtcgtttc atcatctctc gtgacgacaa caaaaacgac    240
ctgtacctgg aaatgaactc tctgaaaacc gaagacaccg cggaatacta ctgcgcgcag    300
aactactacg gttctacccc ggactactgg ggtcagggta ccctggttac cgtttct       357
```

```
<210> SEQ ID NO 293
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 293
gaagttcagc tgaccgaatc tggtggtggt ctggttcagc cgggtggttc tctgcgtctg    60
tcttgcgcgg cgtctggttt catcttctct aaccactaca tgaactgggt tcgtcaggcg    120
ccgggtaaag gtctggaatg gatcggtgaa atccgttcta aatcttctaa cggtgcgacc    180
tcttacgcgg aatctgttaa aggtcgtttc atcatctctc gtgacgacaa cggtaactct    240
ctgaccctgg aaatgaactc tctgaaaacc gaagacaccg cggaatacta ctgcgcgcag    300
aactactacg gttctacccc ggactactgg ggtcagggta ccctggttac cgtttct       357
```

```
<210> SEQ ID NO 294
<211> LENGTH: 357
<212> TYPE: DNA
<213> ORGANISM: Artificial Sequence
```

<220> FEATURE:
<223> OTHER INFORMATION: Infliximab VH variant

<400> SEQUENCE: 294

```
gaagttcagc tggttgaatc tggtggtggt ctggttcagc cgggtggttc tctgcgtctg      60
tcttgcgcgg cgtctcagtt catcttctct aaccactgga tgaactgggt tcgtcaggcg     120
ccgggtaaag gtctggaatg gatcggtgaa atccgttcta atcttctaa cggtgcgacc      180
tcttacgcgg aatctgttaa aggtcgtttc atcatctctc gtgacggtaa caaaaccgac     240
ctgaccctgg aaatgaactc tctgaaaacc gaagacaccg cggaatacta ctgcgcgcag     300
aactactacg gttctaccta cgactactgg ggtcaggta ccctggttac cgtttct        357
```

<210> SEQ ID NO 295
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 295

```
gaagttcagc tgaccgaatc tggtggtggt ctggttcagc cgggtggttc tctgcgtctg      60
tcttgccgtg cgtctcagtc taccttctct aaccactaca tgaactgggt tcgtcaggcg     120
ccgggtaaag gtctggaatg gatcggtgaa atccgttcta atctatcaa ctctgcgacc      180
cactacgcgg aatctgttaa aggtcgtttc atcatctctc gtgacggtaa caaaaccgac     240
ctgaccctgg aaatgaactc tctgaaaacc gaagacaccg cggaatacta ctgcgcgcgt     300
aactactacg gttctacccc ggactactgg ggtcagggta ccctggttac cgtttct       357
```

<210> SEQ ID NO 296
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 296

```
gaagttcagc tgaccgaatc tggtggtggt ctggttcagc cgggtggttc tctgcgtctg      60
tcttgcgcgg cgtctcagtt caccttctct aaccactaca tgaactgggt tcgtcaggcg     120
ccgggtaaag gtctggaatg gatcggtgaa atccgttcta atctatcta ctctgcgacc      180
tcttacgcgg aatctgttaa aggtcgtttc atcatctctc gtgacggtaa caaaaactct    240
ctgaccctgg aaatgaactc tctgaaaacc gaagacaccg cggaatacta ctgcgcgcag     300
aactactatg gttctaccta cgactactgg ggtcagggta ccctggttac cgtttct       357
```

<210> SEQ ID NO 297
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 297

```
gaagttcagc tggttgaatc tggtggtggt ctggttcagc cgggtggttc tctgcgtctg      60
tcttgccgtg cgtctggttc tatcttctct aaccactgga tgaactgggt tcgtcaggcg     120
ccgggtaaag gtctggaatg gatcggtgaa atccgttcta atcttctaa ctctgcgacc      180
cactacgcgg aatctgttaa aggtcgtttc atcatctctc gtgacgacaa caaaaacgac    240
```

-continued

```
ctgaccctgg aaatgaactc tctgaaaacc gaagacaccg cggaatacta ctgcgcgcgt    300
aactactacg gttctaccta cgactactgg ggtcaggcta ccctggttac cgtttct       357

<210> SEQ ID NO 298
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 298
gaagttcagc tggttgaatc tggtggtggt ctggttcagc cgggtggttc tctgcgtctg     60
tcttgcgcgg cgtctggttc tatcttctct aaccactgga tgaactgggt tcgtcaggcg   120
ccgggtaaag gtctggaatg gatcggtgaa atccgttcta atctatcaa ctctgcgacc    180 tcttacgcgg aatctgttaa aggtcgtttc atcatctctc gtgacgacaa caaaaccgac   240
ctgtacctgg aaatgaactc tctgaaaacc gaagacaccg cggaatacta ctgcgcgcag   300
aactactacg gttctacccc ggactactgg ggtcagggta ccctggttac cgtttct       357

<210> SEQ ID NO 299
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 299
gaagttcagc tgaccgaatc tggtggtggt ctggttcagc cgggtggttc tctgcgtctg     60
tcttgccgtg cgtctggttt catcttctct aaccactaca tgaactgggt tcgtcaggcg   120
ccgggtaaag gtctggaatg gatcggtgaa atccgttcta atctatcaa ctctgcgacc    180 cactacgcgg aatctgttaa aggtcgtttc atcatctctc gtgacgacaa cggtaactct   240
ctgtacctgg aaatgaactc tctgaaaacc gaagacaccg cggaatacta ctgcgcgcgt   300
aactactacg gttctacccc ggactactgg ggtcagggta ccctggttac cgtttct       357

<210> SEQ ID NO 300
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 300
gaagttcagc tggttgaatc tggtggtggt ctggttcagc cgggtggttc tctgcgtctg     60
tcttgtcgtg cgtctggttt caccttctct aaccactgga tgaactgggt tcgtcaggcg   120
ccgggtaaag gtctggaatg gatcggtgaa atccgttcta atctatcta ctctgcgacc    180 cactacgcgg aatctgttaa aggtcgtttc atcatctctc gtgacgacaa caaaaccgac   240
ctgtacctgg aaatgaactc tctgaaaacc gaagacaccg cggaatacta ctgcgcgcgt   300
aactactacg gttctacccc ggactactgg ggtcagggta ccctggttac cgtttct       357

<210> SEQ ID NO 301
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 301
```

```
gaagttcagc tggttgaatc tggtggtggt ctggttcagc cgggtggttc tctgcgtctg    60
tcttgccgtg cgtctcagtt catcttctct aaccactaca tgaactgggt tcgtcaggcg   120
ccgggtaaag gtctggaatg gatcggtgaa atccgttcta atctatctat cggtgcgacc   180
cactacgcgg aatctgttaa aggtcgtttc atcatctctc gtgacggtaa cggtaccgac   240
ctgtacctgg aaatgaactc tctgaaaacc gaagacaccg cggaatacta ctgcgcgcgt   300
aactactacg gttctaccta cgactactgg ggtcagggta ccctggttac cgtttct      357
```

<210> SEQ ID NO 302
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 302

```
gaagttcagc tgaccgaatc tggtggtggt ctggttcagc cgggtggttc tctgcgtctg    60
tcttgccgtg cgtctcagtc taccttctct aaccactaca tgaactgggt tcgtcaggcg   120
ccgggtaaag gtctggaatg gatcggtgaa atccgttcta atcttctaa ctctgcgacc    180 tcttacgcgg aatctgttaa aggtcgtttc atcatctctc gtgacggtaa caaaaactct   240
ctgtacctgg aaatgaactc tctgaaaacc gaagacaccg cggaatacta ctgcgcgcag   300
aactactacg gttctacccc ggactactgg ggtcagggta ccctggttac cgtttct      357
```

<210> SEQ ID NO 303
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 303

```
gaagttcagc tggttgaatc tggtggtggt ctggttcagc cgggtggttc tctgcgtctg    60
tcttgccgtg cgtctggttc tatcttctct aaccactaca tgaactgggt tcgtcaggcg   120
ccgggtaaag gtctggaatg gatcggtgaa atccgttcta atctatcaa ctctgcgacc    180 cactacgcgg aatctgttaa aggtcgtttc atcatctctc gtgacggtaa cggtacctct   240
ctgtacctgg aaatgaactc tctgaaaacc gaagacaccg cggaatacta ctgcgcgcag   300
aactactacg gttctaccta cgactactgg ggtcagggta ccctggttac cgtttct      357
```

<210> SEQ ID NO 304
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 304

```
gaagttcagc tgaccgaatc tggtggtggt ctggttcagc cgggtggttc tctgcgtctg    60
tcttgcgcgg cgtctcagtc taccttctct aaccactgga tgaactgggt tcgtcaggcg   120
ccgggtaaag gtctggaatg gatcggtgaa atccgttcta atctatcaa cggtgcgacc    180 cactacgcgg aatctgttaa aggtcgtttc atcatctctc gtgacgacaa cggtaacgac   240
ctgaccctgg aaatgaactc tctgaaaacc gaagacaccg cggaatacta ctgcgcgcag   300
aactactacg gttctacccc ggactactgg ggtcagggta ccctggttac cgtttct      357
```

<210> SEQ ID NO 305
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 305

```
gaagttcagc tgaccgaatc tggtggtggt ctggttcagc cgggtggttc tctgcgtctg      60
tcttgcgcgg cgtctcagtt caccttctct aaccactgga tgaactgggt tcgtcaggcg     120
ccgggtaaag gtctggaatg gatcggtgaa atccgttcta atcttctaa ctctgcgacc      180
cactacgcgg aatctgttaa aggtcgtttc atcatctctc gtgacggtaa caaaacctct     240
ctgaccctgg aaatgaactc tctgaaaacc gaagacaccg cggaatacta ctgcgcgcgt     300
aactactacg gttctacccc ggactactgg ggtcaggta ccctggttac cgtttct        357
```

<210> SEQ ID NO 306
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 306

```
gaagttcagc tggttgaatc tggtggtggt ctggttcagc cgggtggttc tctgcgtctg      60
tcttgcgcgg cgtctcagtt caccttctct aaccactgga tgaactgggt tcgtcaggcg     120
ccgggtaaag gtctggaatg gatcggtgaa atccgttcta atctatcaa ctctgcgacc      180
tcttacgcgg aatctgttaa aggtcgtttc atcatctctc gtgacgacaa caaaaactct    240
ctgtacctgg aaatgaactc tctgaaaacc gaagacaccg cggaatacta ctgcgcgcgt     300
aactactacg gttctactcc ggactactgg ggtcagggta ccctggttac cgtttct       357
```

<210> SEQ ID NO 307
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 307

```
gaagttcagc tgaccgaatc tggtggtggt ctggttcagc cgggtggttc tctgcgtctg      60
tcttgccgtg cgtctcagtc tatcttctct aaccactgga tgaactgggt tcgtcaggcg     120
ccgggtaaag gtctggaatg gatcggtgaa atccgttcta atctatcta tggtgcgacc     180
tcttacgcgg aatctgttaa aggtcgtttc atcatctctc gtgacggtaa caaaaccgac    240
ctgtacctgg aaatgaactc tctgaaaacc gaagacaccg cggaatacta ctgcgcgcag     300
aactactacg gttctacccc ggactactgg ggtcagggta ccctggttac cgtttct       357
```

<210> SEQ ID NO 308
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 308

```
gaagttcagc tgaccgaatc tggtggtggt ctggttcagc cgggtggttc tctgcgtctg      60
tcttgccgtg cgtctcagtc taccttctct aaccactgga tgaactgggt tcgtcaggcg     120
```

```
ccgggtaaag gtctggaatg gatcggtgaa atccgttcta atcttctta ctctgcgacc    180 cactacgcgg aatctgttaa aggtcgtttc atcatctctc gtgacggtaa cggtaactct    240
ctgtacctgg aaatgaactc tctgaaaacc gaagacaccg cggaatacta ctgcgcgcag    300
aactactacg gttctacccc ggactactgg ggtcagggta ccctggttac cgtttct       357
```

<210> SEQ ID NO 309
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 309

```
gaagttcagc tggttgaatc tggtggtggt ctggttcagc cgggtggttc tctgcgtctg    60
tcttgcgcgg cgtctcagtt caccttctct aaccactaca tgaactgggt tcgtcaggcg    120
ccgggtaaag gtctggaatg gatcggtgaa atccgttcta atctatcaa ctctgcgacc    180 cactacgcgg aatctgttaa aggtcgtttc atcatctctc gtgacgacaa cggtaacgac    240
ctgtacctgg aaatgaactc tctgaaaacc gaagacaccg cggaatacta ctgcgcgcag    300
aactactacg gttctaccta cgactactgg ggtcagggta ccctggttac cgtttct      357
```

<210> SEQ ID NO 310
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 310

```
gaagttcagc tgaccgaatc tggtggtggt ctggttcagc cgggtggttc tctgcgtctg    60
tcttgccgtg cgtctcagtt catcttctct aaccactaca tgaactgggt tcgtcaggcg    120
ccgggtaaag gtctggaatg gatcggtgaa atccgttcta atctatcaa ctctgcgacc    180 tcttacgcgg aatctgttaa aggtcgtttc atcatctctc gtgacggtaa cggtaacgac    240
ctgaccctgg aaatgaactc tctgaaaacc gaagacaccg cggaatacta ctgcgcgcgt    300
aactactacg gttctaccta cgactactgg ggtcagggta ccctggttac cgtttct      357
```

<210> SEQ ID NO 311
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 311

```
gaagttcagc tgaccgaatc tggtggtggt ctggttcagc cgggtggttc tctgcgtctg    60
tcttgccgtg cgtctcagtt caccttctct aaccactaca tgaactgggt tcgtcaggcg    120
ccaggtaaag gtctggaatg gatcggtgaa atccgttcta atcttctta cggtgcgacc    180 tcttacgcgg aatctgttaa aggtcgtttc atcatctctc gtgacgacaa cggtaacgac    240
ctgtacctgg aaatgaactc tctgaaaacc gaagacaccg cggaatacta ctgcgcgcgt    300
aactactacg gttctaccta cgactactgg ggtcagggta ccctggttac cgtttct      357
```

<210> SEQ ID NO 312
<211> LENGTH: 357
<212> TYPE: DNA

<213> ORGANISM: Artificial Sequence
<220> FEATURE:
<223> OTHER INFORMATION: Infliximab VH variant

<400> SEQUENCE: 312

```
gaagttcagc tggttgaatc tggtggtggt ctggttcagc cgggtggttc tctgcgtctg    60
tcttgcgcgg cgtctcagtc taccttctct aaccactaca tgaactgggt tcgtcaggcg   120
ccgggtaaag gtctggaatg gatcggtgaa atccgttcta atctctctaa cagtgcgacc   180
cactacgcgg aatctgttaa aggtcgtttc atcatctctc gtgacggtaa caaaaacgac   240
ctgtacctgg aaatgaactc tctgaaaacc gaagacaccg cggaatacta ctgcgcgcgt   300
aactactacg gttctacccc ggactactgg ggtcagggta ccctggttac cgtttct      357
```

<210> SEQ ID NO 313
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 313

```
gaagttcagc tgaccgaatc tggtggtggt ctggttcagc cgggtggttc tctgcgtctg    60
tcttgcgcgg cgtctcagtt caccttctct aaccactaca tgaactgggt tcgtcaggcg   120
ccgggtaaag gtctggaatg gatcggtgaa atccgttcta atctatcaa cggtgcgacc    180
tcttacgcgg aatctgttaa aggtcgtttc atcatctctc gtgacgacaa cggtacctct   240
ctgaccctgg aaatgaactc tctgaaaacc gaagacaccg cggaatacta ctgcgcgcgt   300
aactactacg gttctacccc ggactactgg ggtcagggta ccctggttac cgtttct      357
```

<210> SEQ ID NO 314
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 314

```
gaagttcagc tggttgaatc tggtggtggt ctggttcagc cgggtggttc tctgcgtctg    60
tcttgccgtg cgtctggttc taccttctct aaccactaca tgaactgggt tcgtcaggcg   120
ccgggtaaag gtctggaatg gatcggtgaa atccgttcta atctatccta ctctgcgacc   180
cactacgcgg aatctgttaa aggtcgtttc atcatctctc gtgacggtaa caaaaactct   240
ctgtacctgg aaatgaactc tctgaaaacc gaagacaccg cggaatacta ctgcgcgcag   300
aactactacg gttctaccta cgactactgg ggtcagggta ccctggttac cgtttct      357
```

<210> SEQ ID NO 315
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 315

```
gaagttcagt tgaccgaatc tggtggtggt ctggttcagc cgggtggttc tctgcgtctg    60
tcttgcgcgg cgtctcagtt catcttctct aaccactgga tgaactgggt tcgtcaggcg   120
ccgggtaaag gtctggaatg gatcggtgaa atccgttcta atcttctta cggtgcgacc    180
tcttacgcgg aatctgttaa aggtcgtttc atcatctctc gtgacgacaa cggtaactct   240
```

```
ctgaccctgg aaatgaactc tctgaaaacc gaagacaccg cggaatacta ctgcgcgcgt    300
aactactacg gttctacccc ggactactgg ggtcaggata ccctggttac cgtttct      357
```

<210> SEQ ID NO 316
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 316

```
gaagttcagc tggttgaatc tggtggtggt ctggttcagc cgggtggttc tctgcgtctg    60
tcttgccgtg cgtctcagtc taccttctct aaccactgga tgaactgggt tcgtcaggcg   120
ccgggtaaag gtctggaatg gatcggtgaa atccgttcta atctatcaa ctctgcgacc    180 tcttacgcgg aatctgttaa aggtcgtttc atcatctctc gtgacgacaa cggtaacgac   240
ctgtacctgg aaatgaactc tttgaaaacc gaagacaccg cggaatacta ctgcgcgcgt   300
aactactacg gttctaccta cgactactgg ggtcaggata ccctggttac cgtttct      357
```

<210> SEQ ID NO 317
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 317

```
gaagttcagc tggttgaatc tggtggtggt ctggttcagc cgggtggttc tctacgtctg    60
tcttgcgcgg cgtctcagtc taccttctct aaccactgga tgaactgggt tcgtcaggcg   120
ccgggtaaag gtctggaatg gatcggtgaa atccgttcta atcttctta cggtgcgacc    180 cactacgcgg aatctgttaa aggtcgtttc atcatctctc gtgacggtaa cggtacctct   240
ctgaccctgg aaatgaactc tctgaaaacc gaagacaccg cggaatacta ctgcgcgcgt   300
aactactacg gttctaccta cgactactgg ggtcaggata ccctggttac cgtttct      357
```

<210> SEQ ID NO 318
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 318

```
gaagttcagc tggttgaatc tggtggtggt ctggttcagc cgggtggttc tctgcgtctg    60
tcttgccgtg cgtctggttt catcttctct aaccactaca tgaactgggt tcgtcaggcg   120
ccgggtaaag gtctggaatg gatcggtgaa atccgttcta atctatcta ctctgcgacc    180 cactacgcgg aatctgttaa aggtcgtttc atcatctctc gtgacgacaa cggtaactct   240
ctgtacctgg aaatgaactc tctgaaaacc gaagacaccg cggaatacta ctgcgcgcag   300
aactactacg gttctaccta cgactactgg ggtcaggata ccctggttac cgtttct      357
```

<210> SEQ ID NO 319
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 319

```
gaagttcagc tgaccgaatc tggtggtggt ctggttcagc cgggtggttc tctgcgtctg    60
tcttgcgcgg cgtctcagtt caccttctct aaccactaca tgaactgggt tcgtcaggcg   120
ccgggtaaag gtctggaatg gatcggtgaa atccgttcta atcttctaa ctctgcgacc    180
tcttacgcgg aatctgttaa aggtcgtttc atcatctctc gtgacggtaa cggtacctct   240
ctgacccgg aaatgaactc tctgaaaacc gaagacaccg cggaatacta ctgcgcgcag    300
aactactacg gttctaccta cgactactgg ggtcaggta ccctggttac cgtttct      357
```

<210> SEQ ID NO 320
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 320

```
gaagttcagc tggttgaatc tggtggtggt ctggttcagc cgggtggttc tctgcgtctg    60
tcttgcgcgg cgtctcagtc tatcttctct aaccactaca tgaactgggt tcgtcaggcg   120
ccgggtaaag gtctggaatg gatcggtgaa atccgttcta atctatcta cggtgcgacc    180
tcttacgcgg aatctgttaa aggtcgtttc atcatctctc gtgacgacaa caaaaactct   240
ctgacccgg aaatgaactc tctgaaaacc gaagacaccg cggaatacta ctgcgcgcgt    300
aactactacg gttctacccc ggactactgg ggtcaggta ccctggttac cgtttct      357
```

<210> SEQ ID NO 321
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 321

```
gaagttcagc tggttgaatc tggtggtggt ctggttcagc cgggtggttc tctgcgtctg    60
tcttgcgcgg cgtctcagtc taccttctct aaccactaca tgaactgggt tcgtcaggcg   120
ccgggtaaag gtctggaatg gatcggtgaa atccgttcta atcttctta cggtgcgacc    180
cactacgcgg aatctgttaa aggtcgtttc atcatctctc gtgacgacaa caaaaacgac   240
ctgtacctgg aaatgaactc tctgaaaacc gaagacaccg cggaatacta ctgcgcgcgt    300
aactactacg gttctacccc ggactactgg ggtcaggta ccctggttac cgtttct      357
```

<210> SEQ ID NO 322
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 322

```
gaagttcagc tgaccgaatc tggtggtggt ctggttcagc cgggtggttc tctgcgtctg    60
tcttgcgcgg cgtctggttc tatcttctct aaccactgga tgaactgggt tcgtcaggcg   120
ccgggtaaag gtctggaatg gatcggtgaa atccgttcta atctatcaa cggtgcgacc    180
cactacgcgg aatctgttaa aggtcgtttc atcatctctc gtgacggtaa cggtacctct   240
ctgtacctgg aaatgaactc tctgaaaacc gaagacaccg cggaatacta ctgcgcgcgt    300
aactactacg gttctacccc ggactactgg ggtcaggta ccctggttac cgtttct      357
```

<210> SEQ ID NO 323
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 323

```
gaagttcagc tggttgaatc tggtggtggt ctggttcagc cgggtggttc tctgcgtctg      60
tcttgcgcgg cgtctcagtc tatcttctct aaccactgga tgaactgggt tcgtcaggcg     120
ccgggtaaag gtctggaatg gatcggtgaa atccgttcta atcttctaa ctctgcgacc      180
tcttacgcgg aatctgttaa aggtcgtttc atcatctctc gtgacggtaa caaaaccgac     240
ctgtacctgg aaatgaactc tctgaaaacc gaagacaccg cggaatacta ctgcgcgcag     300
aactactacg gttctaccta cgactactgg ggtcaggggta ccctggttac cgtttct      357
```

<210> SEQ ID NO 324
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 324

```
gaagttcagc tgaccgaatc tggtggtggt ctggttcagc cgggtggttc tctgcgtctg      60
tcttgcgcgg cgtctcagtc tatcttctct aaccactgga tgaactgggt tcgtcaggcg     120
ccgggtaaag gtctggaatg gatcggtgaa atccgttcta atctatcta ctctgcgacc      180
cactacgcgg aatctgttaa aggtcgtttc atcatctctc gtgacgacaa cggtacctct     240
ctgtacctag aaatgaactc tctgaaaacc gaagacaccg cggaatacta ctgcgcgcag     300
aactactacg gttctacccc ggactactgg ggtcagggta ccctggttac cgtttct      357
```

<210> SEQ ID NO 325
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 325

```
gaagttcagc tggttgaatc tggtggtggt ctggttcagc cgggtggttc tctgcgtctg      60
tcttgcgcgg cgtctggttc taccttctct aaccactaca tgaactgggt tcgtcaggcg     120
ccgggtaaag gtctggaatg gatcggtgaa atccgttcta atcttctta ctctgcgacc      180
tcttacgcgg aatctgttaa aggtcgtttc atcatctctc gtgacggtaa cggtaccgac     240
ctgaccctgg aaatgaactc tctgaaaacc gaagacaccg cggaatacta ctgcgcgcag     300
aactactacg gttctaccta cgactactgg ggtcagggta ccctggttac cgtttct      357
```

<210> SEQ ID NO 326
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 326

```
gaagttcagc tgaccgaatc tggtggtggt ctggttcagc cgggtggttc tctgcgtctg      60
```

```
tcttgccgtg cgtctggttt catcttctct aaccactaca tgaactgggt tcgtcaggcg    120
ccgggtaaag gtctggaatg gatcggtgaa atccgttcta atcttctaa ctctgcgacc    180 tcttacgcgg aatctgttaa aggtcgtttc atcatctctc gtgacggtaa caaaaacgac    240
ctgtacctgg aaatgaactc tctgaaaacc gaagacaccg cggaatacta ctgcgcgcgt    300
aactactacg gttctacccc ggactactgg ggtcagggta ccctggttac cgtttct      357

<210> SEQ ID NO 327
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 327
gaagttcagc tgaccgaatc tggtggtggt ctggttcagc cgggtggttc tctgcgtctg    60
tcttgccgtg cgtctcagtc tatcttctct aaccactaca tgaactgggt tcgtcaggcg    120
ccgggtaaag gtctggaatg gatcggtgaa atccgttcta atcttctta cggtgcgacc    180 tcttacgcgg aatctgttaa aggtcgtttc atcatctctc gtgacgacaa caaaaactct    240
ctgaccctgg aaatgaactc tctgaaaacc gaagacaccg cggaatacta ctgcgcgcag    300
aactactacg gttctacccc ggactactgg ggtcagggta ccctggttac cgtttct      357

<210> SEQ ID NO 328
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 328
gaagttcagc tgaccgaatc tggtggtggt ctggttcagc cgggtggttc tctgcgtctg    60
tcttgcgcgg cgtctggttc taccttctct aaccactaca tgaactgggt tcgtcaggcg    120
ccgggtaaag gtctggaatg gatcggtgaa atccgttcta atcttctaa ctctgcgacc    180 cactacgcgg aatctgttaa aggtcgtttc atcatctctc gtgacgacaa cggtacctct    240
ctgtacctgg aaatgaactc tctgaaaacc gaagacaccg cggaatacta ctgcgcgcgt    300
aactactacg gttctaccta cgactactgg ggtcagggta ccctggttac cgtttct      357

<210> SEQ ID NO 329
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 329
gaagttcagc tggttgaatc tggtggtggt ctggttcagc cgggtggttc tctgcgtctg    60
tcttgcgcgg cgtctggttc taccttctct aaccactgga tgaactgggt tcgtcaggcg    120
ccgggtaaag gtctggaatg gatcggtgaa atccgttcta atctatcta cggtgcgacc    180 tcttacgcgg aatctgttaa aggtcgtttc atcatctctc gtgacggtaa caaaaactct    240
ctgtacctgg aaatgaactc tctgaaaacc gaagacaccg cggaatacta ctgcgcgcgt    300
aactactacg gttctaccta cgactactgg ggtcagggta ccctggttac cgtttct      357

<210> SEQ ID NO 330
<211> LENGTH: 357
```

<212> TYPE: DNA
<213> ORGANISM: Artificial Sequence
<220> FEATURE:
<223> OTHER INFORMATION: Infliximab VH variant

<400> SEQUENCE: 330

| | | | | | |
|---|---|---|---|---|---|
| gaagttcagc | tggttgaatc | tggtggtggt | ctggttcagc | cgggtggttc | tctgcgtctg | 60 |
| tcttgccgtg | cgtctcagtt | caccttctct | aaccactaca | tgaactgggt | tcgtcaggcg | 120 |
| ccgggtaaag | gtctggaatg | gatcggtgaa | atccgttcta | atctatcta | ctctgcgacc | 180 |
| tcttacgcgg | aatctgttaa | aggtcgtttc | atcatctctc | gtgacgacaa | cggtacctct | 240 |
| ctgaccctgg | aaatgaactc | tctgaaaacc | gaagacaccg | cggaatacta | ctgcgcgcgt | 300 |
| aactactacg | gttctaccta | cgactactgg | ggtcagggta | ccctggttac | cgtttct | 357 |

<210> SEQ ID NO 331
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 331

| | | | | | |
|---|---|---|---|---|---|
| gaagttcagc | tggttgaatc | tggtggtggt | ctggttcagc | cgggtggttc | tctgcgtctg | 60 |
| tcttgcgcgg | cgtctcagtc | tatcttctct | aaccactgga | tgaactgggt | tcgtcaggcg | 120 |
| ccgggtaaag | gtctggaatg | gatcggtgaa | atccgttcta | atctatcaa | ctctgcgacc | 180 |
| tcttacgcgg | aatctgttaa | aggtcgtttc | atcatctctc | gtgacggtaa | cggtaacgac | 240 |
| ctgtacctgg | aaatgaactc | tctgaaaacc | gaagacaccg | cggaatacta | ctgcgcgcag | 300 |
| aactactacg | gttctaccta | cgactactgg | ggtcagggta | ccctggttac | cgtttct | 357 |

<210> SEQ ID NO 332
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 332

| | | | | | |
|---|---|---|---|---|---|
| gaagttcagc | tggttgaatc | tggtggtggt | ctggttcagc | cgggtggttc | tctgcgtctg | 60 |
| tcttgccgtg | cgtctggttc | tatcttctct | aaccactaca | tgaactgggt | tcgtcaggcg | 120 |
| ccgggtaaag | gtctggaatg | gatcggtgaa | atccgttcta | atcttctaa | ctctgcgacc | 180 |
| tcttacgcgg | aatctgttaa | aggtcgtttc | atcatctctc | gtgacggtaa | caaaaacgac | 240 |
| ctgtacctgg | aaatgaactc | tctgaaaacc | gaagacaccg | cggaatacta | ctgcgcgcag | 300 |
| aactactacg | gttctaccta | cgactactgg | ggtcagggta | ccctggttac | cgtttct | 357 |

<210> SEQ ID NO 333
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 333

| | | | | | |
|---|---|---|---|---|---|
| gaagttcagc | tgaccgaatc | tggtggtggt | ctggttcagc | cgggtggttc | tctgcgtctg | 60 |
| tcttgccgtg | cgtctcagtc | taccttctct | aaccactaca | tgaactgggt | tcgtcaggcg | 120 |
| ccgggtaaag | gtctggaatg | gatcggtgaa | atccgttcta | atcttctaa | cggtgcgacc | 180 |

```
tcttacgcgg aatctgttaa aggtcgtttc atcatctctc gtgacgacaa cggtaacgac    240
ctgtacctgg aaatgaactc tctgaaaacc gaagacaccg cggaatacta ctgcgcgcag    300
aactactacg gttctaccta cgactactgg ggtcagggta ccctggttac cgtttct       357
```

<210> SEQ ID NO 334
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 334

```
gaagttcagc tggttgaatc tggtggtggt ctggttcagc cgggtggttc tctgcgtctg    60
tcttgcgcgg cgtctggttt catcttctct aaccactgga tgaactgggt tcgtcaggcg    120
ccgggtaaag gtctggaatg gatcggtgaa atccgttcta atctatcaa cggtgcgacc     180 cactacgcgg aatctgttaa aggtcgtttc atcatctctc gtgacggtaa caaaaacgac    240
ctgaccctgg aaatgaactc tctgaaaacc gaagacaccg cggaatacta ctgcgcgcgt    300
aactactacg gttctacccc ggactactgg ggtcagggta ccctggttac cgtttct       357
```

<210> SEQ ID NO 335
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 335

```
gaagttcagc tggttgaatc tggtggtggt ctggttcagc cgggtggttc tctgcgtctg    60
tcttgcgcgg cgtctcagtc tatcttctct aaccactgga tgaactgggt tcgtcaggcg    120
ccgggtaaag gtctggaatg gatcggtgaa atccgttcta atctatcaa ctctgcgacc     180 cactacgcgg aatctgttaa aggtcgtttc atcatctctc gtgacggtaa cggtaccgac    240
ctgaccctgg aaatgaactc tctgaaaacc gaagacaccg cggaatacta ctgcgcgcgt    300
aactactacg gttctacccc ggactactgg ggtcagggta ccctggttac cgtttct       357
```

<210> SEQ ID NO 336
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 336

```
gaagttcagc tggttgaatc tggtggtggt ctggttcagc cgggtggttc tctgcgtctg    60
tcttgccgtg cgtctcagtt catcttctct aaccactaca tgaactgggt tcgtcaggcg    120
ccgggtaaag gtctggaatg gatcggtgaa atccgttcta atctatcta cggtgcgacc     180 tcttacgcgg aatctgttaa aggtcgtttc atcatctctc gtgacggtaa cggtaacgac    240
ctgtacctgg aaatgaactc tctgaaaacc gaagacaccg cggaatacta ctgcgcgcag    300
aactactacg gttctaccta cgactactgg ggtcagggta ccctggttac cgtttct       357
```

<210> SEQ ID NO 337
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 337

| gaagttcagc tgaccgaatc tggtggtggt ctggttcagc cgggtggttc tctgcgtctg | 60 |
| tcttgccgtg cgtctcagtt catcttctct aaccactaca tgaactgggt tcgtcaggcg | 120 |
| ccgggtaaag gtctggaatg gatcggtgaa atccgttcta atcttctta ctctgcgacc | 180 |
| cactacgcgg aatctgttaa aggtcgtttc atcatctctc gtgacgacaa cggtaactct | 240 |
| ctgtacctgg aaatgaactc tctgaaaacc gaagacaccg cggaatacta ctgcgcgcag | 300 |
| aactactacg gttctaccta cgactactgg ggtcaggta ccctggttac cgtttct | 357 |

<210> SEQ ID NO 338
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 338

| gaagttcagc tggttgaatc tggtggtggt ctggttcagc cgggtggttc tctgcgtctg | 60 |
| tcttgcgcgg cgtctcagtt caccttctct aaccactaca tgaactgggt tcgtcaggcg | 120 |
| ccgggtaaag gtctggaatg gatcggtgaa atccgttcta atctatcaa cggtgcgacc | 180 |
| tcttacgcgg aatctgttaa aggtcgtttc atcatctctc gtgacgacaa cggtaccgac | 240 |
| ctgtacctgg aaatgaactc tctgaaaacc gaagacaccg cggaatacta ctgcgcgcgt | 300 |
| aactactacg gttctaccta cgactactgg ggtcaggta ccctggttac cgtttct | 357 |

<210> SEQ ID NO 339
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 339

| gaagttcagc tggttgaatc tggtggtggt ctggttcagc cgggtggttc tctgcgtctg | 60 |
| tcttgcgcgg cgtctcagtt catcttctct aaccactaca tgaactgggt tcgtcaggcg | 120 |
| ccgggtaaag gtctggaatg gatcggtgaa atccgttcta atctatcta cggtgcgacc | 180 |
| cactacgcgg aatctgttaa aggtcgtttc atcatctctc gtgacggtaa cggtaactct | 240 |
| ctgaccctgg aaatgaactc tctgaaaacc gaagacaccg cggaatacta ctgcgcgcgt | 300 |
| aactactacg gttctacccc ggactactgg ggtcaggta ccctggttac cgtttct | 357 |

<210> SEQ ID NO 340
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 340

| gaagttcagc tggttgaatc tggtggtggt ctggttcagc cgggtggttc tctgcgtctg | 60 |
| tcttgcgcgg cgtctcagtt caccttctct aaccactaca tgaactgggt tcgtcaggcg | 120 |
| ccgggtaaag gtctggaatg gatcggtgaa atccgttcta atctatcaa cggtgcgacc | 180 |
| cactacgcgg aatctgttaa aggtcgtttc atcatctctc gtgacgacaa cggtaccctct | 240 |
| ctgaccctgg aaatgaactc tctgaaaacc gaagacaccg cggaatacta ctgcgcgcag | 300 |

```
<210> SEQ ID NO 341
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 341
gaagttcagc tggttgaatc tggtggtggt ctggttcagc cgggtggttc tctgcgtctg      60
tcttgccgtg cgtctcagtt caccttctct aaccactaca tgaactgggt tcgtcaggcg     120
ccgggtaaag gtctggaatg gatcggtgaa atccgttcta atcttctaa cggtgcgacc      180
tcttacgcgg aatctgttaa aggtcgtttc atcatctctc gtgacggtaa cggtaacgac     240
ctgaccctgg aaatgaactc tctgaaaacc gaagacaccg cggaatacta ctgcgcgcgt     300
aactactacg gttctaccta cgactactgg ggtcagggta ccctggttac cgtttct        357

<210> SEQ ID NO 342
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 342
gaagttcagc tgaccgaatc tggtggtggt ctggttcagc cgggtggttc tctgcgtctg      60
tcttgccgtg cgtctcagtc taccttctct aaccactaca tgaactgggt tcgtcaggcg     120
ccgggtaaag gtctggaatg gatcggtgaa atccgttcta atcttctaa cggtgcgacc      180
tcttacgcgg aatctgttaa aggtcgtttc atcatctctc gtgacgacaa cggtaactct     240
ctgaccctgg aaatgaactc tctgaaaacc gaagacaccg cggaatacta ctgcgcgcag     300
aactactacg gttctaccta cgactactgg ggtcagggta ccctggttac cgtttct        357

<210> SEQ ID NO 343
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 343
gaagttcagc tgaccgaatc tggtggtggt ctggttcagc cgggtggttc tctgcgtctg      60
tcttgcgcgg cgtctcagtc taccttctct aaccactgga tgaactgggt tcgtcaggcg     120
ccgggtaaag gtctggaatg gatcggtgaa atccgttcta atcttctta ctctgcgacc      180
tcttacgcgg aatctgttaa aggtcgtttc atcatctctc gtgacgacaa caaaaactct     240
ctgtacctgg aaatgaactc tctgaaaacc gaagacaccg cggaatacta ctgcgcgcgt     300
aactactacg gttctaccta cgactactgg ggtcagggta ccctggttac cgtttct        357

<210> SEQ ID NO 344
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 344
gaagttcagc tgaccgaatc tggtggtggt ctggttcagc cgggtggttc tctgcgtctg      60
```

```
tcttgcgcgg cgtctcagtc taccttctct aaccactgga tgaactgggt tcgtcaggcg    120
ccgggtaaag gtctggaatg gatcggtgaa atccgttcta atctatcaa ctctgcgacc    180 tcttacgcgg aatctgttaa aggtcgtttc atcatctctc gtgacgacaa caaaaacgac    240
ctgaccctgg aaatgaactc tctgaaaacc gaagacaccg cggaatacta ctgcgcgcgt    300
aactactacg gttctaccta cgactactgg ggtcaggta ccctggttac tgtttct       357

<210> SEQ ID NO 345
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 345
gaagttcagc tgaccgaatc tggtggtggt ctggttcagc cgggtggttc tctgcgtctg     60
tcttgccgtg cgtctggttc tatcttctct aaccactgga tgaactgggt tcgtcaggcg    120
ccgggtaaag gtctggaatg gatcggtgaa atccgttcta atctatcta ctctgcgacc    180 tcttacgcgg aatctgttaa aggtcgtttc atcatctctc gtgacgacaa cggtacctct    240
ctgaccctgg aaatgaactc tctgaaaacc gaagacaccg cggaatacta ctgcgcgcag    300
aactactacg gttctacccc ggactactgg ggtcaggta ccctggttac cgttct         357

<210> SEQ ID NO 346
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 346
gaagttcagc tggttgaatc tggtggtggt ctggttcagc cgggtggttc tctgcgtctg     60
tcttgccgtg cgtctcagtt catcttctct aaccactgga tgaactgggt tcgtcaggcg    120
ccgggtaaag gtctggaatg gatcggtgaa atccgttcta atctatcta cggtgcgacc    180 cactacgcgg aatctgttaa aggtcgtttc atcatctctc gtgacgacaa caaaaacgac    240
ctgtacctgg aaatgaactc tctgaaaacc gaagacaccg cggaatacta ctgcgcgcgt    300
aactactacg gttctacccc ggactactgg ggtcaggta ccctggttac cgttct         357

<210> SEQ ID NO 347
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 347
gaagttcagc tggttgaatc tggtggtggt ctggttcagc cgggtggttc tctgcgtctg     60
tcttgcgcgg cgtctggttt catcttctct aaccactgga tgaactgggt tcgtcaggcg    120
ccgggtaaag gtctggaatg gatcggtgaa atccgttcta atctatcta ctctgcgacc    180 tcttacgcgg aatctgttaa aggtcgtttc atcatctctc gtgacggtaa cggtacctct    240
ctgaccctgg aaatgaactc tctgaaaacc gaagacaccg cggaatacta ctgcgcgcgt    300
aactactacg gttctaccta cgactactgg ggtcaggta ccctggttac cgttct         357

<210> SEQ ID NO 348
```

<211> LENGTH: 357
<212> TYPE: DNA
<213> ORGANISM: Artificial Sequence
<220> FEATURE:
<223> OTHER INFORMATION: Infliximab VH variant

<400> SEQUENCE: 348

| | | | | | |
|---|---|---|---|---|---|
| gaagttcagc | tggttgaatc | tggtggtggt | ctggttcagc | cgggtggttc | tctgcgtctg | 60 |
| tcttgccgtg | cgtctcagtt | catcttctct | aaccactaca | tgaactgggt | tcgtcaggcg | 120 |
| ccgggaaaag | gtctggaatg | gatcggtgaa | atccgttcta | atcttcttac | ctctgcgacc | 180 |
| tcttacgcgg | aatctgttaa | aggtcgtttc | atcatctctc | gtgacggtaa | caaaaacgac | 240 |
| ctgtacctgg | aaatgaattc | tctgaaaacc | gaagacaccg | cggaatacta | ctgcgcgcag | 300 |
| aactactacg | gttctaccta | cgactactgg | ggtcagggta | ccctggttac | cgtttct | 357 |

<210> SEQ ID NO 349
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 349

| | | | | | |
|---|---|---|---|---|---|
| gaagttcagc | tgaccgaatc | tggtggtggt | ctggttcagc | cgggtggttc | tctgcgtctg | 60 |
| tcttgccgtg | cgtctggttt | catcttctct | aaccactgga | tgaactgggt | tcgtcaggcg | 120 |
| ccgggtaaag | gtctggaatg | gatcggtgaa | atccgttcta | atctatctac | tctgcgacc | 180 |
| cactacgcgg | aatctgttaa | aggtcgtttc | atcatctctc | gtgacgacaa | cggtaacgac | 240 |
| ctgtacctgg | aaatgaactc | tttgaaaacc | gaagacaccg | cggaatacta | ctgcgcgcag | 300 |
| aactactacg | gttctacccc | cggactactgg | ggtcaggta | ccctggttac | cgtttct | 357 |

<210> SEQ ID NO 350
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 350

| | | | | | |
|---|---|---|---|---|---|
| gaagttcagc | tggttgaatc | tggtggtggt | ctggttcagc | cgggtggttc | tctgcgtctg | 60 |
| tcttgcgcgg | cgtctcagtt | catcttctct | aaccactaca | tgaactgggt | tcgtcaggcg | 120 |
| ccgggtaaag | gtctggaatg | gatcggtgaa | atccgttcta | atcttcttac | ctctgcgacc | 180 |
| cactacgcgg | aatctgttaa | aggtcgtttc | atcatctctc | gtgacggtaa | caaaaacgac | 240 |
| ctgaccctgg | aaatgaactc | tctgaaaacc | gaagacaccg | cggaatacta | ctgcgcgcgt | 300 |
| aactactacg | gttctaccta | cgactactgg | ggtcagggta | ccctggttac | cgtttct | 357 |

<210> SEQ ID NO 351
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 351

| | | | | | |
|---|---|---|---|---|---|
| gaagttcagc | tggttgaatc | tggtggtggt | ctggttcagc | cgggtggttc | tctgcgtctg | 60 |
| tcttgcgcgg | cgtctcagtt | catcttctct | aaccactgga | tgaactgggt | tcgtcaggcg | 120 |
| ccgggtaaag | gtctggaatg | gatcggtgaa | atccgttcta | atctatctac | tctgcgacc | 180 |

```
cactacgcgg aatctgttaa aggtcgtttc atcatctctc gtgacgacaa caaaaccgac    240
ctgaccctgg aaatgaactc tctgaaaacc gaagacaccg cggaatacta ctgcgcgcag    300
aactattacg gttctacccc ggactactgg ggtcagggta ccctggttac cgtttct       357

<210> SEQ ID NO 352
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 352
gaagttcagc tgaccgaatc tggtggtggt ctggttcagc cgggtggttc tctgcgtctg     60
tcttgcgcgg cgtctggttc tatcttctct aaccactaca tgaactgggt tcgtcaggcg    120
ccgggtaaag gtctggaatg gatcggtgaa atccgttcta atctatctta ctctgcgacc    180
cactacgcgg aatctgttaa aggtcgtttc atcatctctc gtgacggtaa cggtaccgac    240
ctgtacctgg aaatgaactc tctgaaaacc gaagacaccg cggaatacta ctgcgcgcgt    300
aactactacg gttctaccta cgactactgg ggtcagggta ccctggttac cgtttct       357

<210> SEQ ID NO 353
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 353
gaagttcagc tggttgaatc tggtggtggt ctggttcagc cgggtggttc tctgcgtctg     60
tcttgcgcgg cgtctcagtt caccttctct aaccactaca tgaactgggt tcgtcaggcg    120
ccgggtaaag gtctggaatg gatcggtgaa atccgttcta atcttcttac ggtgcgacc     180 cactacgcgg aatctgttaa aggtcgtttc atcatctctc gtgacggtaa caaaaccgac    240
ctgtacctgg aaatgaactc tctgaaaacc gaagacaccg cggaatacta ctgcgcgcag    300
aactactacg gttctaccta cgactactgg ggtcagggta ccctggttac cgtttct       357

<210> SEQ ID NO 354
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 354
gaagttcagc tggttgaatc tggtggtggt ctggttcagc cgggtggttc tctgcgtctg     60
tcttgcgcgg cgtctcagtt catcttctct aaccactaca tgaactgggt tcgtcaggcg    120
ccgggtaaag gtctggaatg gatcggtgaa atccgttcta atctatcaac tctgcgacc     180 tcttacgcgg aatctgttaa aggtcgtttc atcatctctc gtgacggtaa caaaaccgac    240
ctgtacctgg aaatgaactc tctgaaaacc gaagacaccg cggaatacta ctgcgcgcgt    300
aactactacg gttctaccta cgactactgg ggtcagggta ccctggttac cgtttct       357

<210> SEQ ID NO 355
<211> LENGTH: 357
<212> TYPE: DNA
<213> ORGANISM: Artificial Sequence
<220> FEATURE:
```

<223> OTHER INFORMATION: Infliximab VH variant

<400> SEQUENCE: 355

```
gaagttcagc tggttgaatc tggtggtggt ctggttcagc cgggtggttc tctgcgtctg    60
tcttgcgcgg cgtctcagtt caccttctct aaccactgga tgaactgggt tcgtcaggcg   120
ccgggtaaag gtctggaatg gatcggtgaa atccgttcta atcttcttac ggtgcgacc    180
cactacgcgg aatctgttaa aggtcgtttc atcatctctc gtgacgacaa caaaaccgac   240
ctgaccctgg aaatgaactc tctgaaaacc gaagacaccg cggaatacta ctgcgcgcgt   300
aactactacg gttctaccta cgactactgg ggtcaggggta ccctggttac cgtttct      357
```

<210> SEQ ID NO 356
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 356

```
gaagttcagc tgaccgaatc tggtggtggt ctggttcagc cgggtggttc tctgcgtctg    60
tcttgcgcgg cgtctcagtc taccttctct aaccactgga tgaactgggt tcgtcaggcg   120
ccgggtaaag gtctggaatg gatcggtgaa atccgttcta atctatcaa cggtgcgacc    180
tcttacgcgg aatctgttaa aggtcgtttc atcatctctc gtgacggtaa caaaacctct   240
ctgtacctgg aaatgaactc tctgaaaacc gaagacaccg cggaatacta ctgcgcgcgt   300
aactactacg gttctacccc ggactactgg ggtcagggta ccctggttac cgtttct      357
```

<210> SEQ ID NO 357
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 357

```
gaagttcagc tgaccgaatc tggtggtggt ctggttcagc cgggtggttc tctgcgtctg    60
tcttgcgcgg cgtctggttt catcttctct aaccactaca tgaactgggt tcgtcaggcg   120
ccgggtaaag gtctggaatg gatcggtgaa atccgttcta atctatcaa cggtgcgacc    180
tcttacgcgg aatctgttaa aggtcgtttc atcatctctc gtgacgacaa cggtaacgac   240
ctgaccctgg aaatgaactc tctgaaaacc gaagacaccg cggaatacta ctgcgcgcag   300
aactactacg gttctacccc ggactactgg ggtcagggta ccctggttac cgtttct      357
```

<210> SEQ ID NO 358
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 358

```
gaagttcagc tggttgaatc tggtggtggt ctggttcagc cgggtggttc tctgcgtctg    60
tcttgcgcgg cgtctggttc taccttctct aaccactgga tgaactgggt tcgtcaggcg   120
ccgggtaaag gtctggaatg gatcggtgaa atccgttcta atctatcaa ctctgcgacc    180
cactacgcgg aatctgttaa aggtcgtttc atcatctctc gtgacgacaa cggtacctct   240
ctgtacctgg aaatgaactc tctgaaaacc gaagacaccg cggaatacta ctgcgcgcag   300
```
aactactacg gttctaccta cgactactgg ggtcaggta ccctggttac cgtttct    357

<210> SEQ ID NO 359
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 359
gaagttcagc tggttgaatc tggtggtggt ctggttcagc cgggtggttc tctgcgtctg    60
tcttgcgcgg cgtctcagtc taccttctct aaccactaca tgaactgggt tcgtcaggcg    120
ccgggtaaag gtctggaatg gatcggtgaa atccgttcta atctatcta ctctgcgacc    180
tcttacgcgg aatctgttaa aggtcgtttc atcatctctc gtgacgacaa cggtaactct    240
ctgtacctgg aaatgaactc tctgaaaacc gaagacaccg cggaatacta ctgcgcgcag    300
aactactacg gttctacccc ggactactgg ggtcaggta ccctggttac cgtttct    357

<210> SEQ ID NO 360
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 360
gaagttcagc tgaccgaatc tggtggtggt ctggttcagc cgggtggttc tctgcgtctg    60
tcttgcgcgg cgtctggttt caccttctct aaccactgga tgaactgggt tcgtcaggcg    120
ccgggtaaag gtctggaatg gatcggtgaa atccgttcta atctatcta cggtgcgacc    180
cactacgcgg aatctgttaa aggtcgtttc atcatctctc gtgacggtaa caaaaacgac    240
ctgaccctgg aaatgaactc tctgaaaacc gaagacaccg cggaatacta ctgcgcgcag    300
aactactacg gttctacccc ggactactgg ggtcaggta ccctggttac cgtttct    357

<210> SEQ ID NO 361
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 361
gaagttcagc tgaccgaatc tggtggtggt ctggttcagc cgggtggttc actgcgtctg    60
tcttgccgtg cgtctcagtc taccttctct aaccactaca tgaactgggt tcgtcaggcg    120
ccgggtaaag gtctggaatg gatcggtgaa atccgttcta atcttctaa ctctgcgacc    180
tcttacgcgg aatctgttaa aggtcgtttc atcatctctc gtgacggtaa caaaaccgac    240
ctgaccctgg aaatgaactc tctgaaaacc gaagacaccg cggaatacta ctgcgcgcgt    300
aactactacg gttctacccc ggactactgg ggtcaggta ccctggttac cgtttct    357

<210> SEQ ID NO 362
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 362

```
gaagttcagc tggttgaatc tggtggtggt ctggttcagc cgggtggttc tctgcgtctg      60
tcttgccgtg cgtctggttc taccttctct aaccactaca tgaactgggt tcgtcaggcg     120
ccgggtaaag gtctggaatg gatcggtgaa atccgttcta atcttctta ctctgcgacc      180 tcttacgcgg aatctgttaa aggtcgtttc atcatctctc gtgacgacaa caaaaccgac     240
ctgaccctgg aaatgaactc tctgaaaacc gaagacaccg cggaatacta ctgcgcgcag     300
aactactacg gttctacccc ggactactgg ggtcagggta ccctggttac cgtttct       357
```

<210> SEQ ID NO 363
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 363

```
gaagttcagc tggttgaatc tggtggtggt ctggttcagc cgggtggttc tctgcgtctg      60
tcttgccgtg cgtctggttt catcttctct aaccactgga tgaactgggt tcgtcaggcg     120
ccgggtaaag gtctggaatg gatcggtgaa atccgttcta atctatcaa cggtgcgacc      180 cactacgcgg aatctgttaa aggtcgtttc atcatctctc gtgacgacaa caaaacctct     240
ctgaccctgg aaatgaactc tctgaaaacc gaagacaccg cggaatacta ctgcgcgcag     300
aactactacg gttctaccta cgactactgg ggtcagggta ccctggttac cgtttct       357
```

<210> SEQ ID NO 364
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 364

```
gaagttcagc tgaccgaatc tggtggtggt ctggttcagc cgggtggttc tctgcgtctg      60
tcttgccgtg cgtctcagtc taccttctct aaccactgga tgaactgggt tcgtcaggcg     120
ccgggtaaag gtctggaatg gatcggtgaa atccgttcta atctatcta ctctgcgacc      180 cactacgcgg aatctgttaa aggtcgtttc atcatctctc gtgacggtaa cggtaacgac     240
ctgtacctgg aaatgaactc tctgaaaacc gaagacaccg cggaatacta ctgcgcgcag     300
aactactatg gttctacccc ggactactgg ggtcagggta ccctggttac cgtttct       357
```

<210> SEQ ID NO 365
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 365

```
gaagttcagc tgaccgaatc tggtggtggt ctggttcagc cgggtggttc tctgcgtctg      60
tcttgcgcgg cgtctcagtc taccttctct aaccactaca tgaactgggt tcgtcaggcg     120
ccgggtaaag gtctggaatg gatcggtgaa atccgttcta atcttctaa cggtgcgacc      180 tcttacgcgg aatctgttaa aggtcgtttc atcatctctc gtgacgacaa caaaaacgac    240
ctgaccctgg aaatgaactc tctgaaaacc gaagacaccg cggaatacta ctgcgcgcag     300
aactactacg gttctaccta cgactactgg ggtcagggta ccctggttac ggtttct       357
```

<210> SEQ ID NO 366
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 366

```
gaagttcagc tggttgaatc tggtggtggt ctggttcagc cgggtggttc tctgcgtctg      60
tcttgcgcgg cgtctggttt caccttctct aaccactaca tgaactgggt tcgtcaggcg     120
ccgggtaaag gtctggaatg gatcggtgaa atccgttcta atctatctta ctctgcgacc     180
cactacgcgg aatctgttaa aggtcgtttc atcatctctc gtgacggtaa cggtaactct     240
ctgaccctgg aaatgaactc tctgaaaacc gaagacaccg cggaatacta ctgcgcgcgt     300
aactactacg gttctacccc ggactactgg ggtcaggtta ccctggttac cgtttct       357
```

<210> SEQ ID NO 367
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 367

```
gaagttcagc tgaccgaatc tggtggtggt ctggttcagc cgggtggttc tctgcgtctg      60
tcttgcgcgg cgtctcagtt caccttctct aaccactgga tgaactgggt tcgtcaggcg     120
ccgggtaaag gtctggaatg gatcggtgaa atccgttcta atctttctaa cggtgcgacc     180
cactacgcgg aatctgttaa aggtcgtttc atcatctctc gtgacgacaa cggtacctct     240
ctgaccctgg aaatgaactc tctgaaaacc gaagacaccg cggaatacta ctgcgcgcgt     300
aactactacg gttctacccc ggactactgg ggtcagggta ccctggttac cgtttct       357
```

<210> SEQ ID NO 368
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 368

```
gaagttcagc tggttgaatc tggtggtggt ctggttcagc cgggtggttc tctgcgtctg      60
tcttgccgtg cgtctggttt catcttctct aaccactaca tgaactgggt tcgtcaggcg     120
ccgggtaaag gtctggaatg gatcggtgaa atccgttcta atcttctaa ctctgcgacc     180
cactacgcgg aatctgttaa aggtcgtttc atcatctctc gtgacgacaa caaaacctct     240
ctgaccctgg aaatgaactc tctgaaaacc gaagacaccg cggaatacta ctgcgcgcag     300
aactactacg gttctacccc ggactactgg ggtcagggta ccctggttac cgtttct       357
```

<210> SEQ ID NO 369
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 369

```
gaagttcagc tggttgaatc tggtggtggt ctggttcagc cgggtggttc tctgcgtctg      60
tcttgcgcgg cgtctggttt caccttctct aaccactgga tgaactgggt tcgtcaggcg     120
```

```
ccgggtaaag gtctggaatg gatcggtgaa atccgttcta atcttctta ctctgcgacc      180 cactacgcgg aatctgttaa aggtcgtttc atcatctctc gtgacgacaa caaaaactct    240
ctgaccctgg aaatgaactc tctgaaaacc gaagacaccg cggaatacta ctgcgcgcag    300
aactactacg gttctacccc ggactactgg ggtcaggta ccctggttac cgtttct       357
```

<210> SEQ ID NO 370
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 370

```
gaagttcagc tgaccgaatc tggtggtggt ctggttcagc cgggtggttc tctgcgtctg     60
tcttgcgcgg cgtctggttt caccttctct aaccactaca tgaactgggt tcgtcaggcg    120
ccgggtaaag gtctggaatg gatcggtgaa atccgttcta atctatcta ctctgcgacc     180 cactacgcgg aatctgttaa aggtcgtttc atcatctctc gtgacggtaa cggtaccgac    240
ctgtacctgg aaatgaactc tctgaaaacc gaagacaccg cggaatacta ctgcgcgcag    300
aactactacg gttctacccc ggactactgg ggtcagggta ccctggttac cgtttct      357
```

<210> SEQ ID NO 371
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 371

```
gaagttcagc tgaccgaatc tggtggtggt ctggttcagc cgggtggttc tctgcgtctg     60
tcttgcgcgg cgtctcagtc taccttctct aaccactaca tgaactgggt tcgtcaggcg    120
ccgggtaaag gtctggaatg gatcggtgaa atccgttcta atcttctta cggtgcgacc    180 tcttacgcgg aatctgttaa aggtcgtttc atcatctctc gtgacggtaa cggtaccctct   240 ctgtacttgg aaatgaactc tctgaaaacc gaagacaccg cggaatacta ctgcgcgcgt   300
aactactacg gttctaccta cgactactgg ggtcagggta ccctggttac cgtttct      357
```

<210> SEQ ID NO 372
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 372

```
gaagttcagc tggttgaatc tggcggtggt ctggttcagc cgggtggttc tctgcgtctg     60
tcttgcgcgg cgtctcagtt catcttctct aaccactaca tgaactgggt tcgtcaggcg    120
ccgggtaaag gtctggaatg gatcggtgaa atccgttcta atctatcaa ctctgcgacc    180 cactacgcgg aatctgttaa aggtcgtttc atcatctctc gtgacggtaa cggtaccgac    240
ctgtacctgg aaatgaactc tctgaaaacc gaagacaccg cggaatacta ctgcgcgcgt    300
aactactacg gttctaccta cgactactgg ggtcagggta ccctggttac cgtttct      357
```

<210> SEQ ID NO 373
<211> LENGTH: 357
<212> TYPE: DNA
<213> ORGANISM: Artificial Sequence

```
<220> FEATURE:
<223> OTHER INFORMATION: Infliximab VH variant

<400> SEQUENCE: 373
gaagttcagc tgaccgaatc tggtggtggt ctggttcagc cgggtggttc tctgcgtctg     60
tcttgccgtg cgtctcagtc taccttctct aaccactgga tgaactgggt tcgtcaggcg    120
ccgggtaaag gtctggaatg gatcggtgaa atccgttcta atctatctat ctctgcgacc    180
tcttacgcgg aatctgttaa aggtcgtttc atcatctctc gtgacggtaa cggtaacgac    240
ctgtacctgg aaatgaactc tctgaaaacc gaagacaccg cggaatacta ctgcgcgcag    300
aactactacg gttctacccc ggactactgg ggtcagggta ccctggttac cgtttct       357

<210> SEQ ID NO 374
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 374
gaagttcagc tgaccgaatc tggtggtggt ctggttcagc cgggtggttc tctgcgtctg     60
tcttgcgcgg cgtctggttc taccttctct aaccactaca tgaactgggt tcgtcaggcg    120
ccgggtaaag gtctggaatg gatcggtgaa atccgttcta atctatctat ctctgcgacc    180
tcttacgcgg aatctgttaa aggtcgtttc atcatctctc gtgacgacaa cggtaactct    240
ctgaccctgg aaatgaactc tctgaaaacc gaagacaccg cggaatacta ctgcgcgcgt    300
aactactacg gttctacccc ggactactgg ggtcagggta ccctggttac cgtttct       357

<210> SEQ ID NO 375
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 375
gaagttcagc tgaccgaatc tggtggtggt ctggttcagc cgggtggttc tctgcgtctg     60
tcttgcgcgg cgtctggttt caccttctct aaccactaca tgaactgggt tcgtcaggcg    120
ccgggtaaag gtctggaatg gatcggtgaa atccgttcta atcttcttac ggtgcgacc     180 tcttacgcgg aatctgttaa aggtcgtttc atcatctctc gtgacggtaa cggtaccgac    240
ctgtacctgg aaatgaactc tctgaaaacc gaagacaccg cggaatacta ctgcgcgcag    300
aactactacg gttctaccta cgactactgg ggtcagggta ccctggttac cgtttct       357

<210> SEQ ID NO 376
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 376
gaagttcagc tggttgaatc tggtggtggt ctggttcagc cgggtggttc tctgcgtctg     60
tcttgcgcgg cgtctggttt catcttctct aaccactaca tgaactgggt tcgtcaggcg    120
ccgggtaaag gtctggaatg gatcggtgaa atccgttcta atctatctac ggtgcgacc     180 tcttacgcgg aatctgttaa aggtcgtttc atcatctctc gtgacgacaa caaaaacgac    240
```

```
ctgtacctgg aaatgaactc tctgaaaacc gaagacaccg cggaatacta ctgcgcgcag    300
aactactacg gttctaccta cgactactgg ggtcaggta ccctggttac cgtttct       357
```

<210> SEQ ID NO 377
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 377

```
gaagttcagc tgaccgaatc tggtggtggt ctggttcagc cgggtggttc tctgcgtctg    60
tcttgcgcgg cgtctcagtt caccttctct aaccactgga tgaactgggt cgtcaggcg    120 ccgggtaaag gtctggaatg gatcggtgaa atccgttcta atctatcta ctctgcgacc    180 cactacgcgg aatctgttaa aggtcgtttc atcatctctc gtgacgacaa cggtacctct    240
ctgaccctgg aaatgaactc tctgaaaacc gaagacaccg cggaatacta ctgcgcgcgt    300
aactactacg gttctacccc ggactactgg ggtcagggta ccctggttac cgtttct       357
```

<210> SEQ ID NO 378
<211> LENGTH: 357
<212> TYPE: DNA
<213> ORGANISM: Artificial Sequence
<220> FEATURE:
<223> OTHER INFORMATION: Infliximab VH variant

<400> SEQUENCE: 378

```
gaagttcagc tggttgaatc tggtggtggt ctggttcagc cgggtggttc tctgcgtctg    60
tcttgccgtg cgtctggttt catcttctct aaccactgga tgaactgggt cgtcaggcg    120 ccgggtaaag gtctggaatg gatcggtgaa atccgttcta atctatcaa ttctgcgacc    180 tcttacgcgg aatctgttaa aggtcgtttc atcatctctc gtgacggtaa caaaaccgac    240
ctgaccctgg aaatgaactc tctgaaaacc gaagacaccg cggaatacta ctgcgcgcgt    300
aactactacg gttctaccta cgactactgg ggtcaggta ccctggttac cgtttct       357
```

<210> SEQ ID NO 379
<211> LENGTH: 107
<212> TYPE: PRT
<213> ORGANISM: Mus musculus

<400> SEQUENCE: 379

```
Asp Ile Leu Leu Thr Gln Ser Pro Ala Ile Leu Ser Val Ser Pro Gly
  1               5                  10                  15

Glu Arg Val Ser Phe Ser Cys Arg Ala Ser Gln Phe Val Gly Ser Ser
             20                  25                  30

Ile His Trp Tyr Gln Gln Arg Thr Asn Gly Ser Pro Arg Leu Leu Ile
         35                  40                  45

Lys Tyr Ala Ser Glu Ser Met Ser Gly Ile Pro Ser Arg Phe Ser Gly
     50                  55                  60

Ser Gly Ser Gly Thr Asp Phe Thr Leu Ser Ile Asn Thr Val Glu Ser
 65                  70                  75                  80

Glu Asp Ile Ala Asp Tyr Tyr Cys Gln Gln Ser His Ser Trp Pro Phe
                 85                  90                  95

Thr Phe Gly Ser Gly Thr Asn Leu Glu Val Lys
                100                 105
```

<210> SEQ ID NO 380

```
<211> LENGTH: 107
<212> TYPE: PRT
<213> ORGANISM: Artificial Sequence
<220> FEATURE:
<223> OTHER INFORMATION: Infliximab VL variant

<400> SEQUENCE: 380

Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Phe Val Gly Ser Ser
             20                  25                  30

Ile His Trp Tyr Gln Gln Lys Pro Asp Gln Ser Pro Lys Leu Leu Ile
         35                  40                  45

Lys Tyr Ala Ser Glu Ser Met Ser Gly Val Pro Ser Arg Phe Ser Gly
 50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gln Gln Ser His Ser Trp Pro Phe
                 85                  90                  95

Thr Phe Gly Pro Gly Thr Lys Val Asp Ile Lys
            100                 105

<210> SEQ ID NO 381
<211> LENGTH: 321
<212> TYPE: DNA
<213> ORGANISM: Artificial Sequence
<220> FEATURE:
<223> OTHER INFORMATION: Infliximab VL variant

<400> SEQUENCE: 381
gaaatcgttc tgacccagtc tccggacttc cagtctgtta ccccgaaaga aaaagttacc    60
atcacctgcc gtgcgtctca gttcgttggt tcttctatcc actggtacca gcagaaaccg   120
gaccagtctc cgaaactgct gatcaaatac gcgtctgaat ctatgtctgg tgttccgtct   180
cgtttctctg gttctggttc tggtaccgac ttcaccttca ccatctcttc tctggaagcg   240
gaagacgcgg cgacctacta ctgccagcag tctcactctt ggccgttcac cttcggtccg   300
ggtaccaaag ttgacatcaa a                                             321

<210> SEQ ID NO 382
<211> LENGTH: 112
<212> TYPE: PRT
<213> ORGANISM: Homo sapiens

<400> SEQUENCE: 382

Ser Ala Ser Thr Lys Gly Pro Ser Val Phe Pro Leu Ala Pro Ser Ser
 1               5                  10                  15

Lys Ser Thr Ser Gly Gly Thr Ala Ala Leu Gly Cys Leu Val Lys Asp
             20                  25                  30

Tyr Phe Pro Glu Pro Val Thr Val Ser Trp Asn Ser Gly Ala Leu Thr
         35                  40                  45

Ser Gly Val His Thr Phe Pro Ala Val Leu Gln Ser Ser Gly Leu Tyr
 50                  55                  60

Ser Leu Ser Ser Val Val Thr Val Pro Ser Ser Ser Leu Gly Thr Gln
 65                  70                  75                  80

Thr Tyr Ile Cys Asn Val Asn His Lys Pro Ser Asn Thr Lys Val Asp
                 85                  90                  95

Lys Lys Ala Glu Pro Lys Ser Cys Asp Lys Thr His Thr Cys Pro Pro
            100                 105                 110
```

```
<210> SEQ ID NO 383
<211> LENGTH: 107
<212> TYPE: PRT
<213> ORGANISM: Homo sapiens

<400> SEQUENCE: 383

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

ANTI-TNFα ANTIBODIES

CROSS-REFERENCE TO RELATED APPLICATIONS

This application claims the benefit of U.S. Provisional Application Ser. No. 60/705,427, filed 4 Aug. 2005, the entire contents of which is incorporated herein by reference.

FIELD OF THE INVENTION

The present invention relates to anti-TNFα antibodies and their use as therapeutics.

BACKGROUND OF THE INVENTION

Efficacy of a therapeutic protein can be limited by an unwanted immune reaction to the therapeutic protein. For monoclonal antibodies, a number of techniques have been developed in attempts to reduce the human anti-murine antibody (HAMA) response. In general, these approaches aim to reduce the mouse genetic information in the final antibody construct while increasing the human genetic information. Examples of such approaches are chimeric, humanized and fully human monoclonal antibodies (mAbs).

Chimeric antibodies contain regions derived from different animal species, such as a murine immunoglobulin (Ig) variable region and a human Ig constant region. Infliximab (sold under the brand name REMICADE®) is a chimeric IgG1κ monoclonal antibody that specifically binds human tumor necrosis factor-α (TNFα). Infliximab has human constant regions and murine variable regions. The heavy chain variable region ($V_H$) of infliximab has 119 amino acids; the light chain variable region ($V_L$) has 107 amino acids. See, U.S. Pat. Nos. 6,277,969, 6,284,471, 6,790,444, and 6,835,823, all of which are incorporated herein by reference.

TNFα can be produced by a wide variety of cells, but activated macrophages constitute the most abundant source of this factor (Vassalli, Ann. Rev. Immunol. 10: 411-452 (1992)). TNFα is a soluble homotrimer of 17 kD protein subunits (Smith, et al., J. Biol. Chem. 262: 6951-6954 (1987)). A membrane-bound 26 kD precursor form of TNFα also exists (Kriegler, et al., Cell 53: 45-53 (1988)).

TNFα causes pro-inflammatory actions which result in tissue injury, such as inducing procoagulant activity on vascular endothelial cells increasing the adherence of neutrophils and lymphocytes, and stimulating the release of platelet activating factor from macrophages, neutrophils and vascular endothelial cells (Pober, et al., J. Immunol. 136: 1680-1687 (1986); Pober, et al., J. Immunol. 138: 3319-3324 (1987); Camussi, et al., J. Exp. Med. 166: 1390-1404 (1987)).

The numerous biological effects of TNFα and the closely related cytokine, TNFβ (also known as lymphotoxin), are mediated by two TNF transmembrane receptors, the p55 and p75 receptors (Hohmann, et al., J. Biol. Chem. 264: 14927-14934 (1989); Engelmann, et al., J. Biol. Chem. 265: 1531-1536 (1990)). Extracellular domains of TNF receptors derived by proteolytic cleavage inhibit TNF functions (Kohno, et al., Proc. Natl. Acad. Sci. U.S.A. 87: 8331-8335 (1990)). TNFα is associated with infections, immune disorders, neoplastic pathologies, autoimmune pathologies and graft-versus host pathologies (Cerami, et al., Immunol. Today 9: 28-31 (1988); Oliff, et al., Cell 50: 555-563 (1987); Piguet, et al., J. Exp. Med. 166: 1280-1289 (1987)). Dysregulation and, in particular, overproduction of TNFα has been implicated in a variety of human diseases including sepsis, cerebral malaria, and autoimmune diseases such as multiple sclerosis, rheumatoid arthritis (RA), systemic lupus erythematosus, and Crohn's disease, as well as cancer (reviewed in Zhang and Tracey, The Cytokine Handbook, Thomson A W (ed). pp 517-548 (1998)). TNFα can mediate cachexia in cancer, infectious pathology, and other catabolic states (reviewed in Tracey, et al., Ann. N.Y. Acad. Sci. 587: 325-331 (1990)).

Neutralizing anti-TNFα antibodies that inhibit TNFα activities are useful in treating and/or diagnosing TNFα-mediated diseases. Infliximab has been approved in the United States for treatment of ankylosing spondylitis, Crohn's disease, psoriatic arthritis and rheumatoid arthritis. It can also effectively treat other disorders or symptoms of various immune and autoimmune pathologies as well as inflammatory diseases, such as systemic lupus erythematosus, thyroidosis, graft versus host disease, scleroderma, diabetes mellitus, Grave's disease, sarcoidosis, chronic inflammatory bowel disease, ulcerative colitis, disseminated intravascular coagulation, atherosclerosis and Kawasaki's pathology. See, U.S. Pat. Nos. 5,656,272, 5,698,195, and 5,919,452, all of which are incorporated herein by reference.

It has been reported that antibodies to infliximab have been observed in some treated patients (Targan et al., N. Engl. J. Med. 337: 1029-1035 (1997); Maini et al., Arthritis Rheum. 41: 1552-1563 (1998)). Accordingly, in order to potentially diminish the incidence of anti-infliximab antibodies in treated patients, it is desirable to reduce the amount of murine amino sequences present in the molecule.

BRIEF DESCRIPTION OF THE DRWINGS

FIG. 1 shows the alignment of $V_H$ regions of the TNFα antibody C7 (SEQ ID NO: 3) and infliximab (SEQ ID NO: 1). Identical amino acids are denoted by a "-." Conservative amino acid changes are shown in bold.

FIG. 2 shows the alignment of $V_L$ regions of C7 (SEQ ID NO: 380) and infliximab (SEQ ID NO: 379). Identical amino acids are denoted by a "-." Conservative amino acid changes are shown in bold.

SUMMARY OF THE INVENTION

Figure 3:
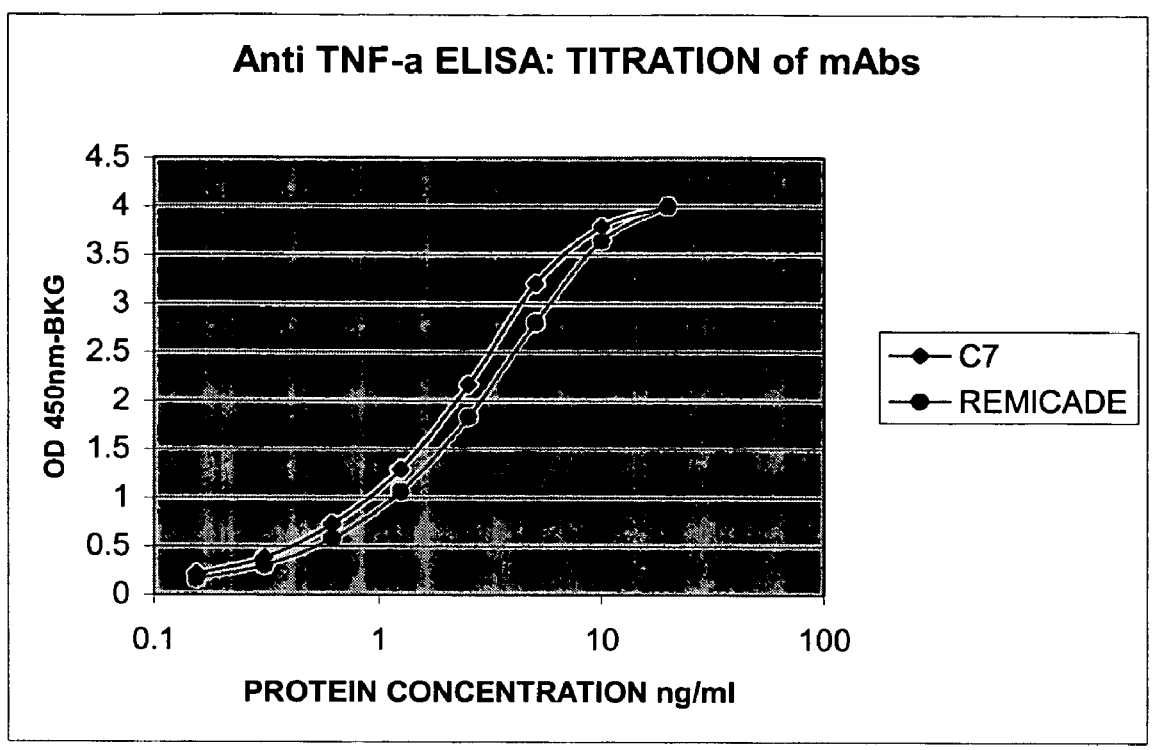
FIG. 3 shows the ELISA titration curves for C7 and infliximab.

One aspect of the invention is a polypeptide comprising a polypeptide having the sequence shown in SEQ ID NO: 2.

Another aspect of the invention is a polypeptide comprising a polypeptide having the sequence shown in SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189 or 190.

Another aspect of the invention is a polynucleotide comprising a polynucleotide having the sequence shown in SEQ ID NOs: 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377 or 378 or a complementary sequence.

Another aspect of the invention is a polynucleotide comprising a polynucleotide encoding the amino acid sequence shown in SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189 or 190.

DETAILED DESCRIPTION OF THE INVENTION

All publications, including but not limited to patents and patent applications, cited in this specification are herein incorporated by reference as though fully set forth. Single letter amino acid codes are used herein as understood by those skilled in the art.

The term "immunoglobulin" as used herein refers to a protein consisting of one or more polypeptides substantially encoded by immunoglobulin genes. The term "antibody" as used herein refers to a protein of the immunoglobulin family that is capable of interacting or otherwise associating with an antigen, as well as biologically active fragments, regions or derivatives thereof, provided by any known technique, such as, but not limited to enzymatic cleavage (e.g., by papain or pepsin digestion), peptide synthesis or recombinant techniques. Examples of biologically active fragments regions of antibodies include, but are not limited to, Fab, Fab', F(ab')$_2$ and Fv. These fragments lack the Fc fragment of an intact antibody, clear more rapidly from the circulation, and can have less non-specific tissue binding than an intact antibody. The term "derivatives" includes modified antibodies that functionally resemble immunoglobulin molecules. An exemplary modification can be the addition of a cytotoxic protein such as a bacterial toxin.

The term "antigen" as used herein refers to a substance that is capable of interacting with the antibody and in the context of the present invention is meant to be TNFα. The TNFα may be soluble TNFα or membrane associated TNFα. The term "TNFα antibodies" as used herein includes antibodies capable of binding portions of TNF and inhibiting the binding of TNFα to TNF receptors.

The present invention provides TNFα antibodies that bind to TNFα and have fewer murine-derived amino acid residues than infliximab. The invention also provides nucleic acids encoding the TNFα antibodies, vectors containing these nucleic acids, host cells, compositions and methods of making and using the TNFα antibodies.

TNFα Antibody Polypeptides and Compositions

The present invention generally relates to a TNFα antibody comprising a polypeptide having the sequence shown in Formula I (SEQ ID NO: 2):

(I)
EVQLX$_5$ESGGG LVQPGGSLRL SCX$_{23}$ASX$_{26}$X$_{27}$X$_{28}$FS
NHX$_{33}$MNWVRQA

PGKGLEWIGE IRSKSX$_{56}$X$_{57}$X$_{58}$AT X$_{61}$YAESVKGRF
IISRDX$_{76}$NX$_{78}$X$_{79}$X$_{80}$

LX$_{82}$LEMNSLKT EDTAEYYCAX$_{100}$ NYYGSTX$_{107}$DYW
GQGTLVTVS wherein,
$X_5$ is V or T; $X_{23}$ is A or R; $X_{26}$ is G or Q; $X_{27}$ is F or S; $X_{28}$ is I or T; $X_{33}$ is W or Y; $X_{56}$ is I or S; $X_{57}$ is N or Y; $X_{58}$ is S or G; $X_{61}$ is H or S; $X_{76}$ is D or G; $X_{78}$ is K or G; $X_{79}$ is N or T; $X_{80}$ is S or D; $X_{82}$ is Y or T; $X_{100}$ is R or Q; and $X_{107}$ is Y or P.

More particularly, the present invention relates to antibodies against TNFα that are less likely to generate anti-infliximab antibodies in humans.

The variable regions of the TNFα antibodies have significant identities with human immunoglobulin sequences or human immunoglobulin germline sequences in the framework regions. Human immunoglobulin sequences can be found in databases such as that of NCBI (http://ncbi.nlm.nih.gov/). Human immunoglobulin germline sequences can be found at, for example, http://vbase.mrc-cpe.cam.ac.uk/. Exemplary heavy chain variable region amino acid sequences are shown in SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189 or 190. An exemplary light chain variable region sequence is shown in SEQ ID NO: 380.

The heavy chain constant region can be derived from any of the known classes or isotypes of human heavy chains, including IgA, IgD, IgE, IgG, IgM and subtypes thereof, such as G1, G2, G3 and G4. Since the heavy chain isotype is responsible for the various effector functions of an antibody, the choice of the heavy chain constant region will be guided by the desired effector functions, such as complement fixation, or antibody-dependent cellular cytotoxicity (ADCC). An exemplary heavy chain constant region amino acid sequence is shown in SEQ ID NO: 382. The light chain constant region can be derived from either human light chain isotype kappa or lambda. An exemplary light chain constant region amino acid sequence is shown in SEQ ID NO: 383.

The TNFα antibodies of the present invention can bind TNFα with a wide range of affinities. Exemplary TNFα antibodies bind TNFα with affinity similar to or higher than that of infliximab. The affinity of TNFα antibodies for TNFα can be determined experimentally using any suitable method, e.g., methods using Biacore or KinExA instrumentation, ELISA and competitive binding assays.

The TNFα antibodies of the present invention are capable of blocking or reducing interactions between TNFα and TNF receptors. These TNFα antibodies neutralize TNFα activity in a range of in vitro assays, such as cell cytotoxicity, mitogenesis, cytokine induction and induction of adhesion molecules.

The TNFα antibodies of the present invention are useful for treating disorders or symptoms of various immune and autoimmune pathologies as well as inflammatory diseases. TNF related pathologies and diseases include, but are not limited to, the following:

(A) acute and chronic immune and autoimmune pathologies, such as systemic lupus erythematosus, rheumatoid arthritis, thyroidosis, graft versus host disease, scleroderma, diabetes mellitus, Graves' disease, and the like;

(B) infections, including, but not limited to, sepsis syndrome, cachexia, circulatory collapse and shock resulting from acute or chronic bacterial infection, acute and chronic parasitic and/or bacterial, viral or fungal infectious diseases, such as AIDS (including sequelae such as cachexia, autoimmune disorders, AIDS dementia complex and infections);

(C) inflammatory diseases, such as chronic inflammatory pathologies and vascular inflammatory pathologies, including chronic inflammatory pathologies such as sarcoidosis, chronic inflammatory bowel disease, ulcerative colitis, and Crohn's pathology and vascular inflammatory pathologies, such as, but not limited to, disseminated intravascular coagulation, atherosclerosis, and Kawasaki's pathology;

(D) neurodegenerative diseases, including, but are not limited to, demyelinating diseases, such as multiple sclerosis and acute transverse myelitis; extrapyramidal and cerebellar disorders'such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo palsy; Cerebellar and Spinocerebellar Disorders, such as astructural lesions of the cerebellum; spinocerebellar degenerations (spinal ataxia, Friedreich's ataxia, cerebellar cortical degenerations, multiple systems degenerations (Mencel, Dejerine-Thomas, Shi-Drager, and Machado-Joseph); and systemic disorders (Refsum's disease, abetalipoprotemia, ataxia, telangiectasia, and mitochondrial multi.system disorder); demyelinating core disorders, such as multiple sclerosis, acute transverse myelitis; disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; subacute sclerosing panencephalitis, Hallerrorden-Spatz disease; and Dementia pugilistica, or any subset thereof;

(E) malignant pathologies involving TNF-secreting tumors or other malignancies involving TNF, such as, but not limited to leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or Mycosis fungoides)); and (F) alcohol-induced hepatitis.

Accordingly, another aspect of the present invention is pharmaceutical compositions comprising at least one TNFα antibody and a pharmaceutically acceptable carrier or diluent known in the art. The carrier or diluent can be a solution, suspension, emulsion, colloid or powder.

A TNFα antibody of the invention is formulated as a pharmaceutical composition in a therapeutically or prophylactically effective amount. The term "effective amount" generally refers to the quantities of antibody necessary for effective therapy, i.e., the partial or complete alleviation of the symptom or disorder for which treatment was sought. Included within the definition of effective therapy are prophylactic treatments intended to reduce the likelihood of onset of the above-described symptoms or disorders.

The composition can optionally comprise at least one further compound, protein or composition useful for treating a TNF-related pathology or disease. For example, combination with anti-rheumatic drugs, anti-inflammatory agents, anti-neoplastic agents, radiotherapeutics, immunosuppressives, and cytotoxic drugs to treat various diseases and conditions are contemplated. In this regard, anti-rheumatic drugs can be at least one of auranofin, azathioprine, chloroquine, D-penicillamine, gold sodium thiomalate hydroxychloroquine, Myocrisin and sulfasalzine methotrexate. Anti-inflammatory agents can be at least one of pentasa, mesalazine, asacol, codeine phosphate, benorylate, fenbufen, naprosyn, diclofenac, etodolac and indomethacin, aspirin and ibuprofen.

Nucleic Acids, Vectors and Cell Lines

Another aspect of the present invention is isolated nucleic acid molecules comprising, complementary to or having significant identity with a polynucleotide encoding at least one TNFα antibody. Other aspects of the present invention include recombinant vectors comprising at least one isolated TNFα antibody encoding nucleic acid molecule and cell lines and organisms that are capable of expressing proteins from the nucleic acid molecules. The nucleic acids, expression vectors and cell lines may generally be used to produce the TNFα antibodies of the invention.

In one embodiment, the nucleic acid compositions of the invention comprise polynucleotides encoding polypeptides having amino acid sequences shown in SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189 or 190. Exemplary nucleic acid sequences comprise polynucleotides shown in SEQ ID NOs: 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377 or 378.

Typically, the nucleic acids of the present invention are used in expression vectors for the preparation of the TNFα antibody polypeptides of the invention. Vectors within the scope of the invention provide necessary elements for eukaryotic expression, including viral promoter driven vectors, such as CMV promoter driven vectors, e.g., pcDNA3.1, pCEP4 and their derivatives, Baculovirus expression vectors, Drosophila expression vectors and expression vectors that are driven by mammalian gene promoters, such as human immunoglobulin gene promoters. Other examples include prokaryotic expression vectors, such as T7 promoter driven vectors, e.g., pET41, lactose promoter driven vectors and arabinose gene promoter driven vectors.

The present invention also relates to cell lines expressing TNFα antibodies. The host cells can be prokaryotic or eukaryotic cells. Exemplary eukaryotic cells are mammalian cells, such as but not limited to, COS-1, COS-7, HEK293, BHK21, CHO, BSC-1, HepG2, 653, SP2/0, NS0, 293, HeLa, myeloma, lymphoma cells, or any derivative thereof. Most preferably, the host cells are HEK293, NS0, SP2/0 or CHO cells. The cell lines of the present invention may stably express at least one TNFα antibody. The cell lines may be generated by stable or transient transfection procedures that are well known in the art.

The present invention further provides methods for expressing at least one TNFα antibody comprising culturing the cell lines under conditions wherein the TNFα antibody is expressed in detectable or recoverable amounts. The present invention also provides methods for generating at least one TNFα antibody comprising translating the TNFα antibody encoding nucleic acids under conditions in vitro or in situ, such that the TNFα antibody is expressed in detectable or recoverable amounts. The present invention also encompasses TNFα antibody produced by the above methods.

A TNFα antibody can be recovered and purified by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylatpatite chromatography and lectin chromatography. High performance liquid chroatography (HPLC) can also be employed for purification.

Methods of Use

The TNFα antibodies are useful as, inter alia, research reagents and therapeutic agents. In one aspect, the present invention relates to a method of decreasing or inhibiting the interactions between TNFα and TNF receptors comprising providing at least one TNFα antibody to a mammal in need thereof. The TNFα antibodies neutralize the biological activities of TNFα and therefore function as antagonists of TNFα. The term "antagonist" is used in the broadest sense and includes a molecule that is capable of, directly or indirectly, partially or fully counteracting, reducing or inhibiting one or more biological activities of TNFα.

The present invention further provides methods for reducing the symptoms of, or treating at least one TNF-related condition or disease comprising administering a therapeutically effective amount of at least one TNFα antibody pharmaceutical composition to a patient in need thereof. As described above, such composition comprises an effective amount of at least one TNFα antibody and a pharmaceutically acceptable carrier or diluent. The effective amount for a given therapy, whether curative or preventative, will generally depend upon many different factors, including means of administration, target site and other medicants administered. Thus, treatment doses will need to be titrated to optimize safety and efficacy.

The conditions and diseases suitable for treatment using the methods of the present invention include but are not limited to, various immune disorders, autoimmune pathologies and inflammatory diseases as listed in detail above. These methods can optionally further comprise co-administration or combination therapies with any standard therapy used to treat the diseases.

The mode of administration can be any suitable route to deliver the pharmaceutically effective amount of TNFα antibody of the present invention to a host. For example, the TNFα antibody can be delivered via parenteral administration, such as subcutaneous, intramuscular, intradermal, intravenous or intranasal administration, or any other means known in the art.

The present invention is further described with reference to the following examples. These examples are merely to illustrate aspects of the present invention and are not intended as limitations of this invention.

EXAMPLE 1

Generation of TNFα Antibodies

Fab libraries were designed based on a combination of infliximab sequence and structure-based criteria. The design goal was molecules with TNFα binding activity at least equal to that of infliximab with high similarity to human immunoglobulin sequences. For example, one criterion of selection for library members was sequence identity or similarity in framework and complementarity determining regions (CDRs) for both heavy and light chains with homologous human counterparts. The human immunoglobulin database at NCBI (ncbi.nlm.nih.gov) and the human germline immunoglobulin database (vbase.mrc-cpe.cam.ac.uk) were employed. Based on these criteria, $V_H$ polypeptides were designed with substitutions at one or a combination of 17 sites. These $V_H$ combinations were combined with one substituted $V_L$ polypeptide having an amino acid sequence shown in SEQ ID NO: 380 (encoding nucleic acid sequence shown in SEQ ID NO: 381). Synthetic Fab DNA libraries were generated according to the method described in U.S. Pat. No. 6,521,427.

The Fab libraries were cloned into pTrcHis2A (Cat. No. V365-20, Invitrogen, Carlsbad, Calif.). Proteins were expressed in E. coli and solid-phase ELISA was used to assess Fab binding to human TNFα. Briefly, 96-well plates were coated overnight at 4° C. with 1 μg/ml of rHuTNF-alpha (Biosource, Camarillo, Calif.) in Carbonate-bicarbonate buffer, pH9.4. After washing in PBS with 0.05% (w/v) Tween-20, the wells were blocked with 1% (w/v) BSA in PBS for 1 hour at room temperature. After washing, plates were incubated with transformed E. coli cell lysate diluted in the assay buffer (1% BSA and 0.05% Tween-20 in 10 mM PBS) for 2 hours at room temperature. Various concentrations of infliximab (0.5, 1 and 2 ng/ml) were used as positive anti-Human Kappa Light Chain Biotin/anti-penta-His Biotin control. Plates were washed and incubated with ImmunoPure Goat Anti-Human Kappa Chain, Biotin Conjugated (Cat. No. 31780, Pierce Biotechnology, Rockford, Ill.) and Penta-His Biotin Conjugate (Cat. No. 34440, QIAGEN, Valencia, Calif.) diluted 1:2000 in the assay buffer for 1 hour at room temperature. Following another washing step, plates were probed for 1 hour at room temperature with 100 μL/well of Streptavidin POD (Cat. No. 1089153, Roche Applied Science, Indianapolis, Ind.) diluted 1:4000 in the assay buffer. Plates were further washed and then incubated with 3,3',5,5'-tetramentylbenzidine (TMB, Cat. No. 34028, Pierce Biotechnology) for 30 minutes. Substrate development was stopped by addition of 100 µL/well TMB Stop Solution (Cat. No. 50-85-05, KPL, Gaithersburg, Md.) and the absorbance was measured at 450 nm via an automated plate spectrophotometer.

188 clones with optical density values of at least twice the background value were further characterized. The $V_H$ amino acid sequences of these clones are shown in SEQ ID NOs: 3 to 190 respectively. The $V_L$ amino acid sequence is shown in SEQ ID NO: 380. Briefly, protein concentration was determined and a titration curve in TNFα ELISA was generated for each clone. A serial dilution curve was generated by eight points titration in duplicate, starting at 50 ng/ml. Clones were ranked according to their EC50. The variable regions of selected Fab clones were subcloned into a mammalian construct with infliximab constant region.

EXAMPLE 2

Sequence Analysis of a TNFα Antibody

The framework portion of the $V_H$ region of one of the novel TNFα antibodies selected as described in Example 1 (C7) (SEQ ID NO: 3) is identical to human germline sequence (VH3 3-72 and JH4). As shown in FIG. 1, when compared to infliximab, 61 out of the 83 amino acids in the framework regions are identical. Of the 23 positions that are different, 14 of them (shown in bold) are conservative amino acid changes.

Similarly, the framework portion of C7 $V_L$ region is identical to human germline sequence (Vk1 A10 and Jk3). As shown in FIG. 2, when compared to infliximab, 63 out of the 80 amino acids in the framework regions are identical. Of the 17 positions that are different, 13 of them (shown in bold) are conservative amino acid changes.

EXAMPLE 3

Binding of Antibody C7 to TNFα

The full-length antibodies were used in a solid-phase ELISA binding assay as described in Example 1 to confirm the TNFα binding. FIG. 3 shows that the ELISA titration curve for C7 is comparable to that of infliximab.

C7 was also used in a Biacore assay to compare the binding constants of C7 and infliximab to TNFα. The results (not shown) indicated that the binding affinity of C7 to TNFα ($K_D$=70 pM) is more than 2-fold higher than that of infliximab ($K_D$=170 pM).

The present invention now being fully described, it will be apparent to one of ordinary skill in the art that many changes and modifications can be made thereto without departing from the spirit or scope of the appended claims.

The invention claimed is:

1. A polypeptide comprising a polypeptide having the sequence shown in SEQ ID NO: 2.

2. A polypeptide comprising a polypeptide having the sequence shown in SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189 or 190.

3. A polynucleotide comprising a polynucleotide encoding the polypeptide of claim 2.

4. A cell line expressing the polypeptide of claim 3.

5. The cell line of claim 4 wherein the cell line is HEK293, NSO, SP2/0 or CHO cell line.

6. A pharmaceutical composition comprising of at least one polypeptide of claim 3 and a pharmaceutically acceptable carrier or diluent.

7. A polynucleotide comprising a polynucleotide having the sequence shown in SEQ ID NOs: 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377 or 378 or a fully complementary sequence of any of the foregoing sequences.

8. A vector comprising the polynucleotide of claims 3, 2, or 7.

9. A cell line comprising the vector of claim 8.

10. The cell line of claim 9 wherein the cell line is HEK293, NSO, SP2/0 or CHO cell line.

* * * * *